United States Patent [19]

Schwartz

[11] Patent Number: 5,720,928
[45] Date of Patent: Feb. 24, 1998

[54] IMAGE PROCESSING AND ANALYSIS OF INDIVIDUAL NUCLEIC ACID MOLECULES

[75] Inventor: David C. Schwartz, New York, N.Y.

[73] Assignee: New York University, New York, N.Y.

[21] Appl. No.: 415,710

[22] Filed: Apr. 3, 1995

Related U.S. Application Data

[63] Continuation-in-part of Ser. No. 162,379, Dec. 7, 1993, Pat. No. 5,599,664, and Ser. No. 128,996, Sep. 30, 1993, which is a continuation-in-part of Ser. No. 879,551, May 4, 1992, Pat. No. 5,405,519, Ser. No. 333,531, Apr. 5, 1989, abandoned, and Ser. No. 244,897, Sep. 15, 1988, abandoned, said Ser. No. 162,379, is a continuation of Ser. No. 333,531, said Ser. No. 879,551, is a continuation of Ser. No. 244,897.

[51] Int. Cl.$^6$ .................... B01J 19/08; G01N 21/00; G01N 31/22; B01L 3/00
[52] U.S. Cl. ................. 422/186; 422/55; 422/58; 422/99; 422/129; 435/6
[58] Field of Search .................. 435/6; 536/23.1; 422/55, 58, 99, 129, 186

[56] References Cited

U.S. PATENT DOCUMENTS

| | | |
|---|---|---|
| 4,473,452 | 9/1984 | Cantor et al. . |
| 4,695,548 | 9/1987 | Cantor et al. . |
| 4,737,251 | 4/1988 | Carle et al. . |
| 4,767,700 | 8/1988 | Wallace . |
| 4,870,004 | 9/1989 | Conroy et al. . |
| 5,059,294 | 10/1991 | Lizardi . |
| 5,079,169 | 1/1992 | Chu et al. . |
| 5,314,829 | 5/1994 | Coles ..................... 436/165 |
| 5,380,833 | 1/1995 | Urdea . |

FOREIGN PATENT DOCUMENTS

| | | |
|---|---|---|
| 2605472 | 4/1988 | European Pat. Off. . |
| 84/02001 | 5/1984 | WIPO . |
| 87/01955 | 9/1987 | WIPO . |

OTHER PUBLICATIONS

Chattoraj et al, "DNA Condenation with Polyamines", J. Mol. Biol. 121, (1978), pp. 327–337.

Ohi et al, "Mapping of Mitochondrial 4S RNA Genes ... by Electron Microscopy", J. Mol. Biol. 212, (1978), pp. 299–310.

Manuelidis et al, Biol. Abstr. 76(4); Ref. No. 27153; p. 2940.

Bensimon, A. et al., 1994, "Alignment and Sensitive Detection of DNA by a Moving Interface" Science 265: 2096.

Perkins, T.T. et al., 1994, "Direct Observation of Tube–like Motion of a Single Polymer chain", 264: 819–822.

Cohen et al., 1993, "A first–generation physical map of the human genome", Nature 366: 698–701.

Guo et al., 1993, "Sizing of Large DNA Molecules by Hook Formation in a Loose Matrix", J. Biomol. Structure and Dynamics 11: 1–10.

Hansma, H.G. et al., 1993, "Atomic force microscopy of DNA in aqueous solutions", Nucleic Acids Research 21: 505–512.

Karrasch, S. et al., 1993, "Covalent Binding of Biological Samples to Solid Supports for Scanning Probe Microscopy in Buffer Solution" Biophysical J. 65: 2437–2446.

Koob et al., 1992, "RecA–AC: single–site cleavage of plasmids and chromosomes at any predetermined restriction site" Nucleic Acids Res. 20:5831.

Zenhausern et al., 1992, "Imaging of DNA by Scanning Force Microscopy", J. Struct. Biol. 108: 69–73.

Lyubchenko et al., 1992, "Atomic Force Microscopy Imaging of Double Stranded DNA and RNA", J. Biomol. Struct. and Dyn. 10: 589–606.

Bustamante et al., 1992, "Circular DNA Molecules Imaged in Air by Scanning Force Microscopy", Biochemistry 31: 22–26.

van denEngh, et al., 1992, "Estimating Genomic Distance from DNA Sequence Location in Cell Nuclei by a Random Walk Model", Science 257: 1410.

Allison et al., 1992, "Immobilization of DNA for scanning probe microscopy", Proc. Natl. Acad. Sci. USA 89: 10129–10133.

Heng et al., 1992, "High–resolution mapping of mammalian genes by in situ hybridization to free chromatin", Proc. Natl. Acad. Sci. USA 89: 9509.

(List continued on next page.)

Primary Examiner—W. Gary Jones
Assistant Examiner—Amy Atzel
Attorney, Agent, or Firm—Pennie & Edmonds LLP

[57] ABSTRACT

A method for observing and determining the size of individual molecules and for determining the weight distribution of a sample containing molecules of varying size, which involves placing a deformable or nondeformable molecule in a medium, subjecting the molecule to an external force, thereby causing conformational and/or positional changes, and then measuring these changes. Preferred ways to measure conformational and positional changes include: (1) determining the rate at which a deformable molecule returns to a relaxed state after termination of the external force, (2) determining the rate at which a molecule becomes oriented in a new direction when the direction of the perturbing force is changed, (3) determining the rate at which a molecule rotates, (4) measuring the length of a molecule, particularly when it is at least partially stretched, or (5) measuring at least one diameter of a spherical or ellipsoidal molecule. Measurements of relaxation, reorientation, and rotation rates, as well as length and diameter can be made using a light microscope connected to an image processor. Molecule relaxation, reorientation and rotation also can be determined using a microscope combined with a spectroscopic device. The invention is particularly useful for measuring polymer molecules, such as nucleic acids, and can be used to determine the size and map location of restriction digests. Breakage of large polymer molecules mounted on a microscope slide is prevented by condensing the molecules before mounting and unfolding the molecules after they have been placed in a matrix.

3 Claims, 52 Drawing Sheets

OTHER PUBLICATIONS

Maier et al., 1992, "Complete coverage of the Schizosaccharomyces pombe genome in yeast artificial chromosomes", *Nat. Genet.* 1:273.

Guo et al., 1992, "Sizing single DNA molecules", *Nature* 359:783–784.

Chumakov et al., 1992, "Continuum of overlapping clones spanning the entire human chromosome 21q", *Nature* 359: 380.

Link, 1991, "Physical Map of the *Saccharomyces cerevisiae* Genome at 110–Kilobase Resolution", *Genetics* 127: 681.

Ferrin et al., 1991, "Selective Cleavage of Human DNA: RecA–Assisted Restriction Endonuclease (RARE) Cleavage", *Science* 254: 1494.

Campbell et al., 1991, "Generation of a nested series of interstitial deletions in yeast artificial chromosomes carrying human DNA", *Proc. Natl. Acad. Sci. USA* 88: 5744.

Cavalli–Sforza, 1990, "Opinion: How Can One Study Individual Variation for 3 Billion Nucleotides of the Human Genome", *Am. J. Hum. Genet.* 46: 649.

Koob et al., 1990, "Cleaving Yeast and *Escherichia coli* Genomes at a single site", *Science* 250: 271–273.

Lichter et al., 1990, "High–Resolution Mapping of Human Chromosome 11 by in Situ Hybridization with Cosmid Clones" *Science* 247: 64.

Stallings et al., 1990, "Physical mapping of human chromosomes by repetetive sequence fingerprinting", *Proc. Natl. Acad. Sci. USA* 87: 6218–6222.

Glazer et al., 1990, "A stable double–stranded DNA–ethidium homodimer complex: Application to picogram fluorescence detection of DNa in agarose gels", *Proc. Natl. Acad. Sci. USA* 87: 3851.

Schwartz et al., 1989, "ED: pulsed electrophoresis instrument", *Nature* 342:575–576.

Lawrence et al., 1988, "Sensitive, High–Resolution Chromatin and Chromosome Mapping In Situ: Presence and Orientation of Two Closely Integrated Copies of EBV in a Lymphoma Line", *Cell* 52:51.

Barlow et al., 1987, "Genetics by gel electrophoresis: the impact of pulsed field gel elctrophoresis on mammalian genetics", *Trends in Genetics* 3: 167–177.

Burke et al., 1987, "Cloning of Large Segments of Exogenous DNA into Yeast by Means of Artificial Chromosome Vectors", *Science* 236: 806.

Church and Gilbert, 1984, "Genomic sequencing", *Proc. Natl. Acad. Sci. USA* 81:1991.

Luckham and Klein, 1984, "Forces between Mica Surfaces Bearing Adsorbed Polyelectrolyte, Poly–L–lysine, in Aqueous Media", *Chem. Soc. Faraday Trans. 1*, 80: 865–878.

Schwartz and Cantor, 1984, "Separation of Yeast Chromosome–Sized DNAs by Pulsed Field Gradient Gel Electrophoresis", *Cell* 37: 67.

Murray and Szostak, 1983, "Construction of Artificial Chromosome in Yeast", *Nature* 305: 189–193.

Manuelidis et al., 1982, "High–resolution Mapping of Satellite DNA using Biotin–labeled DNA Probes", *J. Cell. Biol.* 95: 619.

Matsumoto, et al., 1981, "Light Microscopic Structure of DNA in Solution Studied by the 4',6–Diamidino–2–phenylindole Staining Method", *J. Mol. Biol.* 132: 501–516.

Gosule and Schellman, 1978, "DNA Condensation with Polyamines", *J. Mol. Biol.* 121: 311–326.

Porath and Axen, 1976, "Immobilization of Enzymes to Agar, Agarose, and Sephadex Supports", *Methods Enzymol.* 44: 19.

Smith and Birnstiel, 1976, "A simple method for DNA restriction site mapping", *Nucleic Acids Res.* 3: 2387–2399.

Massa et al., 1973, "Flow Properties of High–Molecular–Weight DNA Solutions: Viscosity, Recoil, and :Longest Retardation Time", *Biopolymers* 12:.

Schwartz et al., 1989, "Conformational Dynamics of Individual DNA Molecules During Gel Electrophoresis", *Nature* 338:520.

Rampino and Chrambach, 1991, "Conformational correlatives of DNA band compression and bidirectional migration during field inversion gel electrophoresis, detected by quantitative video epifluoresence microscopy", *Biopolymers* 31: 1297–1307.

Romling et al., 1989, "A physical genome map of *Pseudomonas aeruginosa*", *EMBO J.* 8(13): 4081–4089.

Smith et al., 1989, "Observation of Individual DNA Molecules Undergoing Gel Electrophoresis", *Science* 242: 203.

Kucherlapati et al., 1988, Genetic Recombination pp. 92–106.

Zubay, 1988, *Biochemistry* (Macmillan Publishing Company, New York) pp. 918–919.

Woolf et al., 1988, "Mapping genomic organization by field inversion and two dimensional gel electrophoresis", *Nucleic Acids Research* 16(9):3863.

Carle et al., 1986, "Electrophoretic Separations of Large DNA Molecules by Periodic Inversion of the Electric Field", *Science* 232: 65–68.

Poddar and Maniloff, 1986, "Chromosome analysis by two–dimensional fingerprinting", Gene 49: 93–102.

Stellwagen, N.C., 1985, "Orientation of DNA molecules in agarose gels by pulsed electric fields", J. Biomol. Str. and Dyn. 3(2): 299.

Yanagida et al., 1983, "Dynamic behaviors of DNA Molecules in solution . . ." Cold Spring Harbor Symp. Quant. Biol. 47: 177.

Dev et al., 1982, "Techniques for chromosome analysis", *Techniques in Somatic Cell Genetics*, edited by Shay, pp. 493–503.

Manuelidis et al., 1992, "High–resolution mapping of satellite DNA using biotin–labeled DNA probes", *Biol. Abstr.* 76(4), Ref. No. 27153, p. 2940.

Chattoraj et al., 1978, "DNA Coordination with polyamines", *J. Mol. Biol.* 121: 327.

Ohi et al., 1978, "Mapping of Mitochondria 4S RNA genes in *Xenopus laevis* by electron microscopy", *J. Mol. Biol.* 121: 299.

Gurrieri et al., 1990, "Imaging of kinked configurations of DNA molecules undergoing orthogonal field alternating gel electrophoresis by fluorescence microscopy", *Biochemistry* 29: 3396–3401.

Bendich and Smith, 1990, "Moving pictures and pulsed–field gel electrophoresis show linear DNA molecules form chloroplasts and mitochondria" *Current Genetics* 17: 421–425.

Smith and Bendich, 1990, "Electrophoretic charge density and persistance length of DNA as measured by fluorescence microscopy", *Biopolymers* 29(8–9): 1167.

Sturm and Weill, 1989, "Direct observation of DNA chain orientation and relaxation by electric birefringence: Implications for the mechanism of separation during pulsed–field gel electrophoresis", *Physical Rev. Letters* 62(13): 1484.

Stellwagen, 1988, "Effect of pulsed and reversing electric fields on the orientation of linear and supercoiled DNA molecules in Agarose Gels", *Biochemistry* 27:6417.

Schwartz, et al., "Conformational Dynamics of Individual DNA Molecules During Gel Electrophoesis", Nature, Apr. 6, 1989, pp. 520–522.

Poddar et al, "Chromosome analysis by two–dimensional fingerprinting", Gene, 49 (1986), pp. 93–102.

Woolf et al, "Mapping genomic organization by field inversion and two dimensional gel electrophoresis", Nucleic Acid Research, vol. 16, No. 9 (1988), pp. 3863–3875.

Roemling et al, "A physical genome map of *Pseudomonas aeruginosa*", The EMBO Journal, vol. 8, No. 13 (1989), pp. 4081–4089.

Yanagida et al, "Dynamic Behaviors of DNA Molecules in Solution . . . ", Cold Sprg. Hrbr. Symp. Quant. Biol. 47, pp. 177–187, 1983.

Zubay, Biochemistry, 1988, pp. 918–919.

Kucherlapati et al, Genetic Recombination, 1988, pp. 92–106.

Smith et al, "Observation of Individual DNA Molecules Undergoing Gel Electrophoresis", Science 242, Jan. 13, 1989 pp. 203–206.

Carle et al, "Electrophoretic Separations of Lage DNA molecules . . . ", Science, Apr. 4, 1986, pp. 65–68.

Dev. et al, "Techniques for Chromosome Analysis", Techniques in SOmatic Cell Genetics, edited by Shay, 1982, pp. 493–503.

Rampino, "The Physics of Gel Electrophoresis".

Stellwagon, "Effect of Pulsed and Reversing Electric Fields . . . " Biochem. 27, 1988, pp. 6417–6424.

Manuelidis et al, Biol. Abstr. 76(4), Ref. No. 27153, p. 2940.

Gerlach et al. (1984) Cytometry 5:562–571.

K. R. Khrapko et al., "A Method For DNA Sequencing By Hybridization With Oligonucleotide Matrix," J. DNA Sequencing and Mapping, 1991, vol. 1, pp. 375–388.

R. C. Williams, "Use Of Polylysine For Adsorption Of Nucleic Acids And Enzymes To Electron Microscope Specimen Films," Proc. Natl. Acad. Sci. USA, vol. 74, No. 6, pp.2311–2315, Jun. 1977.

F. Fish et al., "A sensitive Solid Phase Microradioimmunoassay For Anti–Double Stranded DNA Antibodies," Arthritis and Rheumatism, vol. 24, No. 3 (Mar. 1981).

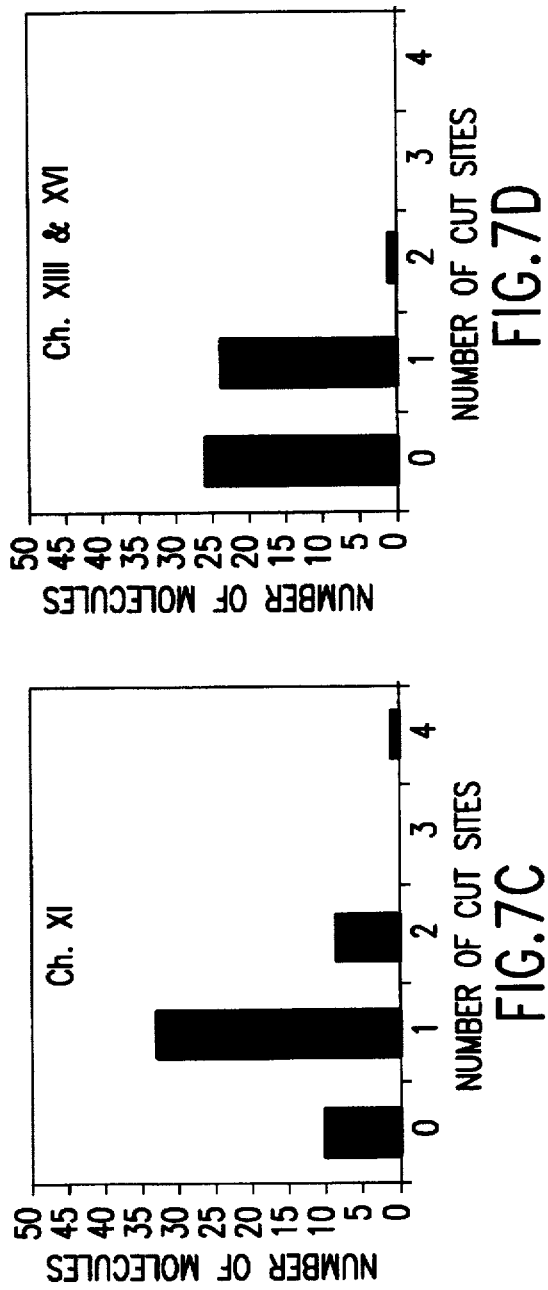
FIG. 7A  FIG. 7B  FIG. 7C  FIG. 7D

CUT SITE

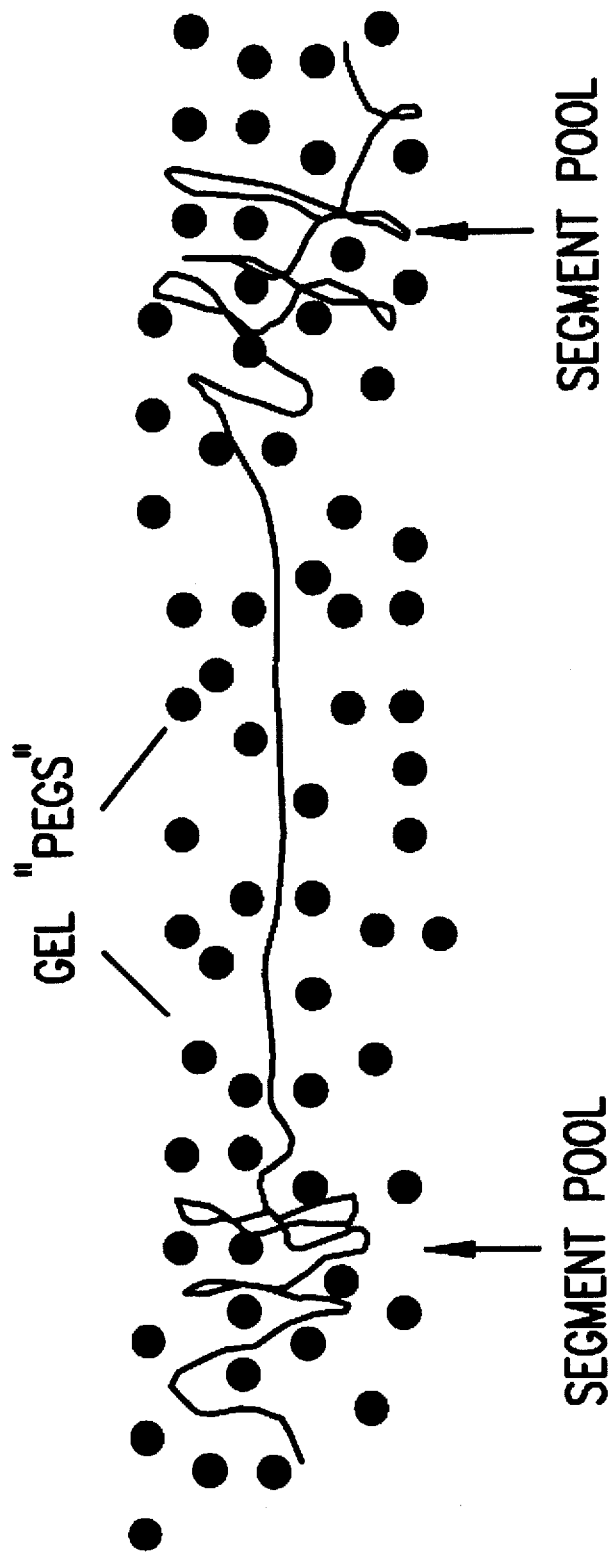

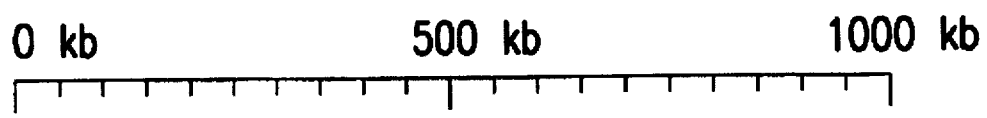
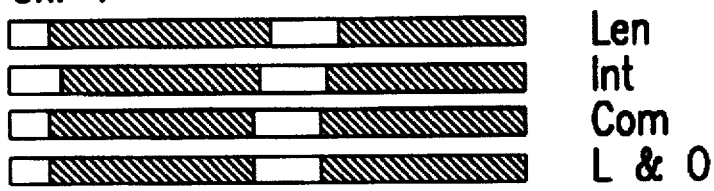
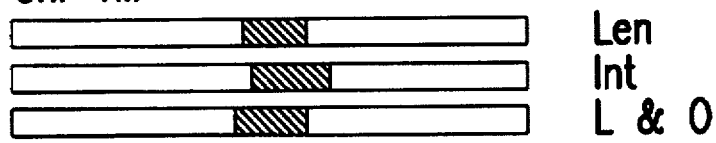
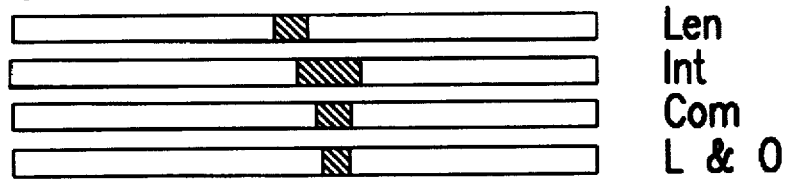
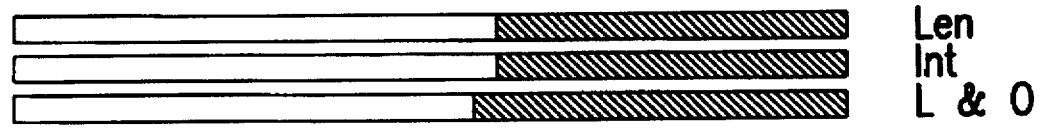
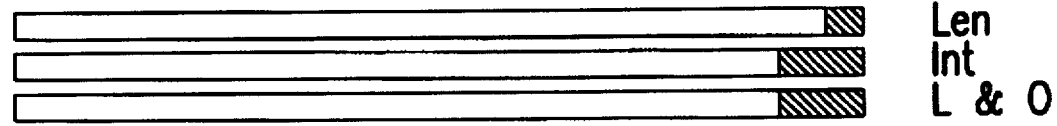
FIG. 12

IMAGE PROCESSING AND ANALYSIS OF INDIVIDUAL NUCLEIC ACID MOLECULES

This application is a continuation-in-part of application Ser. No. 08/162,379, filed Dec. 7, 1993, now U.S. Pat. No. 5,599,664, which in turn is a continuation of application Ser. No. 07/333,531, filed Apr. 5, 1989, (abandoned). This application is also a continuation-in-part of application Ser. No. 08/128,996, filed Sep. 30, 1993, which is a continuation-in-part of: (a) application Ser. No. 07/879,551, filed May 4, 1992, now U.S. Pat. No. 5,405,519, which in turn, is a continuation of application Ser. No. 07/244,897, filed Sep. 15, 1988, (abandoned); and (b) a continuation-in-part of application Ser. No. 07/333,531, filed Apr. 5, 1989, (abandoned), and application Ser. No. 07/244,897, filed Sep. 15, 1988, (abandoned). The entire contents of each of the foregoing applications is incorporated by reference herein in its entirety.

This invention was made with U.S. Government support under Contract No. HG 00225 awarded by the National Institutes of Health of the U.S. Department of Health and Human Services and the U.S. Government has certain rights in the invention.

1. FIELD OF THE INVENTION

This invention relates to methods and compositions for manipulating and characterizing individual polymer molecules, especially nucleic acid molecules, according to, for example, size and/or nucleotide sequence.

2. BACKGROUND OF THE INVENTION

The analysis of nucleic acid molecules at the genome level is an extremely complex endeavor which requires accurate, rapid characterization of large numbers of often very large nucleic acid molecules via high throughput DNA mapping and sequencing. The construction of physical maps, and ultimately of nucleotide sequences, for eukaryotic chromosomes currently remains laborious and difficult. This is due, in part, to the fact that current procedures for mapping and sequencing DNA were originally designed to analyze nucleic acid at the gene, rather than at the genome, level (Chumakov, I. et al., 1992, Nature 359:380; Maier, E. et al., 1992, Nat. Genet. 1:273).

Traditionally, the separation and molecular weight distribution of nucleic acid molecules has been accomplished, most commonly, via gel electrophoresis (see, for example, Freifelder, 1976, Physical Biochemistry, W. H. Freeman), which involves moving a population of molecules through an appropriate medium, such that the molecules are separated according to size. Such electrophoretic methods offer an acceptable level of size resolution, but, especially for purposes of high throughput mapping, suffer from a number of setbacks.

For example, such techniques require the preparation of DNA in bulk amounts. First, with respect to genome mapping, such preparative procedures may require sources such as genomic DNA or DNA from yeast artificial chromosomes (YACs; Burke, D. T. et al., 1987, Science 236:806; Barlow, et al., 1987, Trends in Genetics 3:167–177; Campbell et al., 1991, Proc. Natl. Acad. Sci. U.S.A. 88:5744). Obtaining quantities of DNA from these sources which is sufficient for detailed analyses, such as restriction mapping, is time consuming and often impractical. Second, because populations of molecules of like size migrate through the medium at the same rate, it is impossible to separate individual molecules from within a sample of particles by utilizing such a technique. Additionally, while it is possible to resolve a wide size range of DNA molecule populations gel electrophoresis techniques, optimal techniques can often require the use of several different gel matrix compositions and/or alternative electrophoresis procedures, depending upon the sizes of the molecules of interest. For example, the separation of large molecules of DNA may require such techniques as pulse field electrophoresis (see, e.g., U.S. Pat. No. 4,473,452). Further, standard gel electrophoresis techniques involve the separation of populations of molecules according to size, making it impossible to separate individual molecules within a polydisperse mixture. In summary, therefore, the accurate, rapid, practical, high throughput separation of individual DNA molecules, especially those of highly disparate sizes, which would often be required for genomic mapping purposes, is impossible via gel electrophoresis.

Techniques have been reported for the visualization of be single nucleic acid molecules and complexes. Such techniques include such fluorescence microscopy-based techniques as fluorescence in situ hybridization (FISH; Manuelidis, L. et al., 1982, J. Cell. Biol. 95:619; Lawrence, C. A. et al., 1988, Cell 52:51; Lichter, P. et al., 1990, Science 247:64; Heng, H. H. Q. et al., 1992, Proc. Natl. Acad. Sci. U.S.A. 89:9509; van den Engh, G. et al., 1992, Science 257:1410) and those reported by, for example, Yanagida (Yanagida, M. et al., 1983, Cold Spring Harbor Symp. Quantit. Biol. 47:177; Matsumoto, S. et al., 1981, J. Mol. Biol. 132:501–516); tethering techniques, whereby one or both ends of a nucleic acid molecule are anchored to a surface (U.S. Pat. Nos. 5,079,169; 5,380,833; Perkins, T. T. et al., 1994, Science 264:819; Bensimon, A. et al., 1994, Science 265:2096); and scanning probe microscopy-based visualization techniques, including scanning tunneling microscopy and atomic force microscopy techniques (see, e.g., Karrasch, S. et al., 1993, Biophysical J. 65:2437–2446; Hansma, H. G. et al., 1993, Nucleic Acids Research 21:505–512; Bustamante, C. et al., 1992, Biochemistry 31:22–26; Lyubchenko, Y. L. et al., 1992, J. Biomol. Struct. and Dyn. 10:589–606; Allison, D. P. et al., 1992, Proc. Natl. Acad. Sci. U.S.A. 89:10129–10133; Zenhausern, F. et al., 1992, J. Struct. Biol. 108:69–73).

While single molecule techniques offer the potential advantage of an ordering capability which gel electrophoresis lacks, none of the current single molecule techniques can be used, on a practical level, as, for example, high resolution genomic mapping tools. The molecules described by Yanagida (Yanagida, M. et al., 1983, Cold Spring Harbor Symp. Quantit. Biol. 47:177; Matsumoto, S. et al., 1981, J. Mol. Biol. 132:501–516), for example, were visualized, primarily free in solution, in a manner which would make any practical mapping impossible. Further, while the FISH technique offers the advantage of using only a limited number of immobilized fragments, usually chromosomes, it is not possible to achieve the sizing resolution available with gel electrophoresis.

Single molecule tethering techniques, as listed above, generally involve individual nucleic acid molecules which have, first, been immobilized onto a surface via one or both of their ends, and, second, have been manipulated such that the molecules are stretched out. These techniques, however, are not suited to genome analysis. First, the steps involved are time consuming and can only be accomplished with a small number of molecules per procedure. Further, in general, the tethered molecules cannot be stored and used again.

A combination of the sizing capability of gel electrophoresis and the ordering capability of certain single molecule techniques such as, for example, FISH, would, therefore, be extremely useful for genomic analyses such as genomic mapping. Such analyses would be further aided by the ability to manipulate the single molecules being analyzed. Additionally, an ability to reuse the nucleic acid samples of interest would increase the efficiency and throughput capability of the analysis. Currently, however, there exists no single technology which embodies, in a practical manner, each of these elements.

Citation of documents herein is not intended as an admission that any of the documents cited herein is pertinent prior art, or an admission that the cited documents are considered material to the patentability of the claims of the present application. All statements as to the date or representations as to the contents of these documents are based on the information available to the applicant and does not constitute any admission as to the correctness of the dates or contents of these documents.

3. SUMMARY OF THE INVENTION

The present invention relates to methods and compositions for characterizing and manipulating individual nucleic acid molecules, including mammalian chromosome-sized individual nucleic acid molecules. The methods and compositions described herein can be utilized for the accurate, rapid, high throughput analysis of nucleic acid molecules at the genome level, and may, for example, include the construction of high resolution physical maps, referred to herein as "optical mapping", and the detection of specific nucleotide sequences within a genome, referred to herein as "optical sequencing."

Specifically, methods are described whereby single nucleic acid molecules, including mammalian chromosome-sized DNA molecules, are elongated and fixed in a rapid, controlled and reproducible manner which allows for the nucleic acid molecules to retain their biological function and, further, makes rapid analysis of the molecules possible. In one embodiment of such a procedure, the molecules are elongated in a flow of a molten or unpolymerized gel composition. The elongated molecules become fixed as the gel composition becomes hardened or polymerized. In such an embodiment, the gel composition is preferably an agarose gel composition. The elongated molecules became fixed as the agarose.

In a second embodiment, the single nucleic acid molecules are elongated and fixed in a controllable manner directly onto a solid, planar surface. This solid, planar surface contains a positive charge density which has been controllably modified such that the single nucleic acid molecules will exhibit an optimal balance between the critical parameters of nucleic acid elongation state, degree of relaxation stability and biological activity. Further, methods, compositions and assays are described by which such an optimal balance can precisely and reproducibly be achieved.

In a third embodiment, the single nucleic acid molecules are elongated via flow-based techniques. In such an embodiment, a single nucleic acid molecule is elongated, manipulated (via, for example, a regio-specific restriction digestion), and/or analyzed in a laminar flow elongation device. The present invention further relates to and describes such a laminar flow elongation device.

The elongated, individual nucleic acid molecules can then be utilized in a variety of ways which have applications for the analysis of nucleic acid at the genome level. For example, such nucleic acid molecules may be used to generate ordered, high resolution single nucleic acid molecule restriction maps. This method is referred to herein as "optical mapping" or "optical restriction mapping". Additionally, methods are presented whereby specific nucleotide sequences present within the elongated nucleic acid molecules can be identified. Such methods are referred to herein as "optical sequencing". The optical mapping and optical sequencing techniques can be used independently or in combination on the same individual nucleic acid molecules.

Still further, the elongated nucleic acid molecules of the invention can be manipulated using any standard procedure. For example, the single nucleic acid molecules may be manipulated by any enzymes which act upon nucleic acid molecules, and which may include, but are not limited to, restriction endonucleases, exonucleases, polymerases, ligases or helicases.

Additionally, methods are also presented for the imaging and sizing of the elongated single nucleic acid molecules. These imaging techniques may, for example, include the use of fluorochromes, microscopy and/or image processing computer software and hardware. Such sizing methods include both static and dynamic measuring techniques.

Still further, high throughput methods for utilizing such single nucleic acid molecules in genome analysis are presented. In one embodiment of such high throughput methods, rapid optical mapping approaches are described for the creation of high-resolution restriction maps. In such an embodiment, single nucleic acid molecules are elongated, fixed and gridded to high density onto a solid surface. These molecules can then be digested with appropriate restriction enzymes for the map construction. In an alternative embodiment, the single nucleic acid molecules can be elongated, fixed and gridded at high density onto a solid surface and utilized in a variety of optical sequencing-based diagnostic methods. In addition to speed, such diagnostic grids can be reused. Further, the high throughput and methods can be utilized to rapidly generate information derived from procedures which combine optical mapping and optical sequencing methods.

The present invention is based on the development of techniques, including high throughput techniques, which reproducibly and rapidly generate populations of individual, elongated nucleic acid molecules that not only retain biological function but are accessible to manipulation and make possible rapid genome analysis.

4. BRIEF DESCRIPTION OF THE FIGURES

FIG. 1. Schematic drawing of an electrophoretic microscopy chamber which is specifically adapted to fluorescence microscopy studies.

FIG. 2. Partly schematic and partly block diagram showing an interconnection of exemplary chamber electrodes in an electrophoresis chamber which may be used in the present invention.

FIGS. 3A–3B. Schematic illustration of the instrumentation used in the microscopic study of DNA molecules in a medium according to this invention, and a more detailed diagram showing the instrumentation for measuring birefringence.

FIGS. 4A–4I. Depicted herein are the DNA molecular conformational and positional changes when G bacteriophage molecules are subject to two sequential electric fields in different directions.

FIGS. 5A–5J. Depicted herein are the DNA molecular conformational and positional changes during relaxation of G bacteriophage DNA molecules after electrophoresis for 600 seconds, as revealed by the fluorescence microscopy experiments described in Example 4.

FIG. 6. Optical mapping. DNA molecules and restriction enzyme are dissolved in molten agarose without magnesium ions. The DNA molecules are elongated by the flow generated when the mixture is sandwiched between a slide and coverslip. Stretched molecules are fixed in place by agarose gelation. Magnesium ion diffusion into the gel triggers digestion and cleavage sites appear as growing gaps as the molecular fragments relax.

FIGS. 7A–7D. Histograms of optical mapping. Not 1 cut frequencies, showing variation with molecule size and number of cut sites, are indicated. Cutting frequencies were scored by counting the number of Not 1 cuts in nucleic acid molecules present in microscope fields. Such fields typically contain approximately 3–5 molecules. Because approximately half the fields showed no Not 1 cutting and were, therefore, not scored, this underestimates the number of uncut molecules. The expected number of cut sites and chromosome sizes: 7A: Ch. 1(240 kb) 1; 7B.: Ch. V and VIII(595 kb) 3 and 2; 7C: Ch. XI(675 kb) 2; and 7D: Ch. XIII and XVI(950 and 975 kb) 1. Chromosome pairs V and VIII, and XIII and XVI were present on the same mount.

FIGS. 8A–8H. Depicted are some restriction fragment relaxation modes for a singly cleaved, gel-fixed, elongated molecule. Horizontal arrows indicate direction of relaxation. Relaxation modes illustrated: 8A depicts fixed molecule before cleavage, 8B–8E depict possible relaxation modes producing detectably cleaved molecules, and 8F–8H depict relaxation modes producing undetectably cleaved molecules.

FIG. 9. Schematic representation depicting possible relaxation events to form pools of segments or "balls" at coil ends. Agarose gel is illustrated as a series of pegs with free spaces available for molecules. Gel pegs might intersect the embedded DNA molecule during gelation and possibly entrap it. The coil segments positioned in the pool region comprise a relaxed sub-coil region and have higher entropy than the coil stretched out between them. These pools may act as molecular rivets in some circumstances, particularly if the segment pool mass approaches that of the intervening coil.

FIGS. 10A–10D. Optical mapping sizing results for Not I endonuclease restriction fragments from *S. cerevisiae* chromosomes I, V, VIII, XI, XIII, and XVI calculated as described, plotted against published results. The diagonal line is for reference. Typical fragment images are shown in this figure. (See example 13). The inset shows the estimate of population standard deviation (kb). Error bars represent 90% confidence (7) on means (main graph) or standard deviation (inset). 10A and 10B: the relative intensity determination of fragment sizes. 10C and 10D: the relative apparent length determination of fragment sizes.

FIGS. 11A–11C. Scatter plot of normalized absolute intensity vs. apparent length. Absolute intensities from six individual images were calculated and plotted against apparent length over a time interval typically used in optical mapping (10–15 minutes). For each sample, the initial intensity was found by averaging absolute intensity values from groups of 5 adjacent images and taking the largest value. The values from several samples were normalized by dividing values from each image by the initial intensity for the sample. 11A: chromosome I 120 kb Not I fragment, 7 samples. 11B: chromosome XI 285 kb Not I fragment, 4 samples. 11C: chromosome XI 360 kb Not I fragment, 4 samples.

FIG. 12. Comparison of Not I endonuclease restriction maps of optical mapping results of *S. cerevisiae* chromosomal DNA molecules with published restriction maps (L&O). Maps were constructed from length (Len), intensity (Int) or a combination of both (Com). Bar lengths for the optical mapping data are proportional to the means plotted in FIGS. 10A–10D, and typical images are shown in FIGS. 13A–13F.

FIGS. 13A–13F. Typical fluorescence microscopy images of *S. cerevisiae* chromosomal DNA molecules stained with DAPI and embedded in agarose gel during Not I restriction endonuclease cleavage. Chromosomal DNA molecules were prepared and fixed as described in Example 13 and cited references. Images were background corrected using a smoothed and attenuated background image, smoothed, and stretched, using 16-bit precision. Images show Not I restriction digestion evolution, with arrows highlighting cut sites. Intervals are timed after addition of $Mg^{2+}$. 13A: Ch. I (240 kb), 20 and 60 sec; 13B: Ch. XI (675 kb), 500, 880 and 1160 sec; 13C: Ch. V (595 kb), 200, 240, 520 sec; 13D: Ch. VIII (595 kb), 440, 1220 and 1360 sec; 13E: Ch. XIII (950 kb), 100 and 560 sec; 13F: Ch. XVI (975 kb), 460 and 560 sec. Bars, 5 µm. A 100× objective was used to image results in FIGS. 13A–13D and a 63× objective was used for FIGS. 13E and 13F.

FIG. 14. Optical mapping results from Rsr II and Asc I endonuclease restriction digest of *S. cerevisiae* chromosomes III and XI. Maps were constructed from fully cut length (Len) or intensity (Int) data, and refined using partial cut length. Bar lengths are proportional to the calculated means, and typical images are shown in FIGS. 15A–15C. Number of cuts was determined as in FIGS. 7A–7D.

FIGS. 15A–15C. Fluorescence microscopy images of *S. cerevisiae* chromosomal DNA molecules stained with DAPI and embedded in agarose gel during Rsr II or Asc I restriction endonuclease cleavage. Chromosomal DNA molecules were digested and analyzed as in FIGS. 13A–13F. Images show restriction digestion evolution, with arrows highlighting cut sites. 15A: Ch. III, Rsr II, 1100 and 1820 sec; 15B: Ch. XI, Rsr II, 20, 600, 920, 1060 sec; 15C: Ch. XI, Asc I, 1160, 1500, 1780, 1940 sec. An isoschizomer to Rsr II, Csp I, was also used and gave identical results. Bar, 5 µm.

FIG. 16. Glass surface properties as a function of polylysine treatment. Glass surfaces were incubated for 16 hours in different concentrations of poly-D-lysine, MW=350,500. Lambda bacteriophage DNA molecules in EcoRI restriction buffer and ethidium homodimer, minus magnesium ions, were mounted onto the treated glass surfaces. Square and circle show ratio of absorbed DNA and average length of absorbed DNA, respectively. Each point represents roughly 50 molecules measured and bars show the standard deviation about a mean. Sample preparation, imaging techniques and analysis are given in Methodology.

FIGS. 17A–17W. Gallery of fluorescence microscopy images of lambda clones from Optical Mapping results. Clones from a mouse yeast artificial chromosome (YAC) (Burke et al., Science 236:806–812, 1987; Murray and Szostak, Nature 305:189–193, 1983) spanning the Pygmy locus were subcloned into Lambda FIX II and digested with EcoRI and BamHI. Maps for these and other molecules (not shown) were constructed by Optical Mapping techniques (Methodology) and shown in FIG. 19. Images show typical molecules used for map construction. Bars: 5 microns. FIG. 17V is an enlargement of FIG. 17T and FIG. 17W is at the same scale as FIG. 17V. The enzymes used for map construction are indicated as (E) for EcoRI and (B) for BamH I. FIG. 17A uncut lambda DNA; FIG. 17B, B3 (E); FIG. 17C, F (B); FIG. 17D, B (s); FIG. 17E, D (S); FIG. 17F, E (S); FIG. 17G, 914 (S); FIG. 17H, S(E); FIG. 17I, G (S); FIG. 17J, C (E); FIG. 17K, B4 (E); FIG. 17L, Y11 (E); FIG. 17M, 618 (E); FIG. 17N, 617 (E); FIG. 17O, 305 (E); FIG. 17P, A (B); FIG. 17Q, 1004 (B); FIG. 17R, E (E); FIG. 17S, B6 (E); FIG. 17T, A2 (E); FIG. 17U, C3 (E); FIG. 17V, A2 (E); FIG. 17W, F (E).

FIGS. 18A–18D. EcoRI and BamH I endonuclease restriction fragment sizing results for Lambda FIX II clones, calculated as described and plotted against gel electrophoresis data. FIG. 18A, Relative fluorescence intensity results. The diagonal line is for reference. Typical fragment images are shown in FIGS. 17A–17W. Inset: estimate of population standard deviation (kb). Error bars represent 90% confidence on means (main graph) or standard deviation (inset). The size of the whole molecule was determined by gel electrophoresis. b, results for small fragments. The best fit line through the origin (slope 0.665) was used to calibrate fragment originally estimated at less than 6.5 kb prior to incorporation into maps. c, results after correction. d, Relative apparent length sizing results from the same images. The diagonal line is for reference.

FIG. 19. EcoRI and BamH I restriction maps constructed by Optical Mapping. Clones are labeled on the left side. The upper ticks are EcoRI restriction sites and lower ticks are BamH I sites. Table 1 shows the fragment sizes.

FIGS. 20A–20H. Optically sizing insert DNA of lambda FIX II clones. Lambda clones mounted on the surface were digested by an enzyme which cut at the polylinker sites, as described in Methodology. The 20 kb and 9 kb vector arms of FIX II cloning system were used as internal size standards to convert relative sizes to absolute sizes. The results of fluorescence intensity and length were shown in Table 2, together with sizes from PFGE. Cases where the enzyme also cut the insert were easily interpreted. Scale bar is 5 microns. FIGS. 20A–20B, Clone F (Sal I): 20 kb, 7.5 kb, 9.5 kb, 9 kb. FIGS. 20B–20D, Clone G (Sal I): 20 kb, 10.1 kb, 4.1 kb, 9 kb. FIGS. 20E–20F, clone B (NotI): 20 kb, 17.6 kb, 9 kb. FIGS. 20G–20H, B3 (SstI): 20 kb, 13.8 kb, 9 kb.

FIG. 21 DNA binding properties of glass surfaces as a function of APTES deposition. Yeast (AB972) chromosome I molecules (240 kb, 72 mm contour length, assuming B-DNA) in (10 mM Tris pH 7.6, 1 mM EDTA, 50 mM NaCl) were applied in molten agarose to glass surfaces previously treated with APTES for the indicated time. The number and length of molecules was measured by fluorescence microscopy after staining with ethidium homodimer. The plot shows the average number of molecules deposited per 100 m² field viewed (square) and the average molecule length (circle), plotted against the time of prior APTES derivatization. Each point represents $^b$ $^{60}$ molecules imaged. Bars indicate the standard deviation about the means. Sample preparation, imaging techniques and analysis are given in Materials and Methods.

FIGS. 22A–22D. Optical mapping sizing results for NotI endonuclease restriction fragments of S. cerevisiae chromosomes I, V, VIII, and XI calculated as described (Example 13) plotted against published results (Link and Olson, Genetics 127:681, 1991). The diagonal line is for reference. Each point represents 20 to 40 imaged fragments. FIGS. 22B and 22D: estimate of population standard deviation (kb). Error bars represent the 90% confidence intervals. FIGS. 22A and 22B Relative apparent length determination of restriction fragment sizes. FIGS. 22C and 22D Relative fluorescence intensity determination of restriction fragment sizes.

FIGS. 23A–23D. 23A–23C: Typical fluorescence micrographs of S. cerevisiae chromosomal DNA molecules digested with NotI restriction endonuclease. Molecules were stained with ethidium homodimer after digestion. Arrows indicate cleavage sites, bars 10 microns. FIG. 23A, chromosome XI, two cuts; FIG. 23B, Chromosome V, three cuts; and FIG. 23C, chromosome VIII, two cuts. FIG. 23D, graphical comparison of optical mapping results and published PFGE restriction maps of yeast chromosomes digested with NotI. Bar lengths for the optical mapping data are proportional to the means based on the fluorescence intensity measurements plotted in FIGS. 22C–22D.

FIGS. 24A–24I. FIGS. 24A–G: Typical fluorescence micrographs of yeast artificial chromosomes digested with NotI, MluI, EagI and NruI restriction endonucleases and stained with ethidium homodimer. Arrows indicate Cleavage sites, bars 10 microns. YAC 7H6 was digested with: FIG. 24A, NruI; FIG. 24B EagI. YAC 3I4 was digested with: FIG. 24C, NotI; FIG. 24D, MluI; FIG. 24E, EagI; FIG. 24F, NotI and MluI; FIG. 24G, MluI and EagI. Graphical comparison of optical mapping results with PFGE mapping results for YACs: FIG. 24H, 7H6; FIG. 24I, 3I4. Double digestion results are included. Bar lengths for the optical mapping data are proportional to the means based on fluorescence intensity measurements.

FIG. 25 is a diagram depicting a laminar flow elongation device.

FIGS. 26 A, B, and C illustrate the characteristic "sunburst" pattern of fixation of elongated molecules using the spotting technique of the present invention.

FIGS. 27 A and B show relaxation measurements as a function of molecular size.

FIGS. 28 A and B are logarithmic plots of relaxation versus size.

5. DETAILED DESCRIPTION OF THE INVENTION

Figure 1:
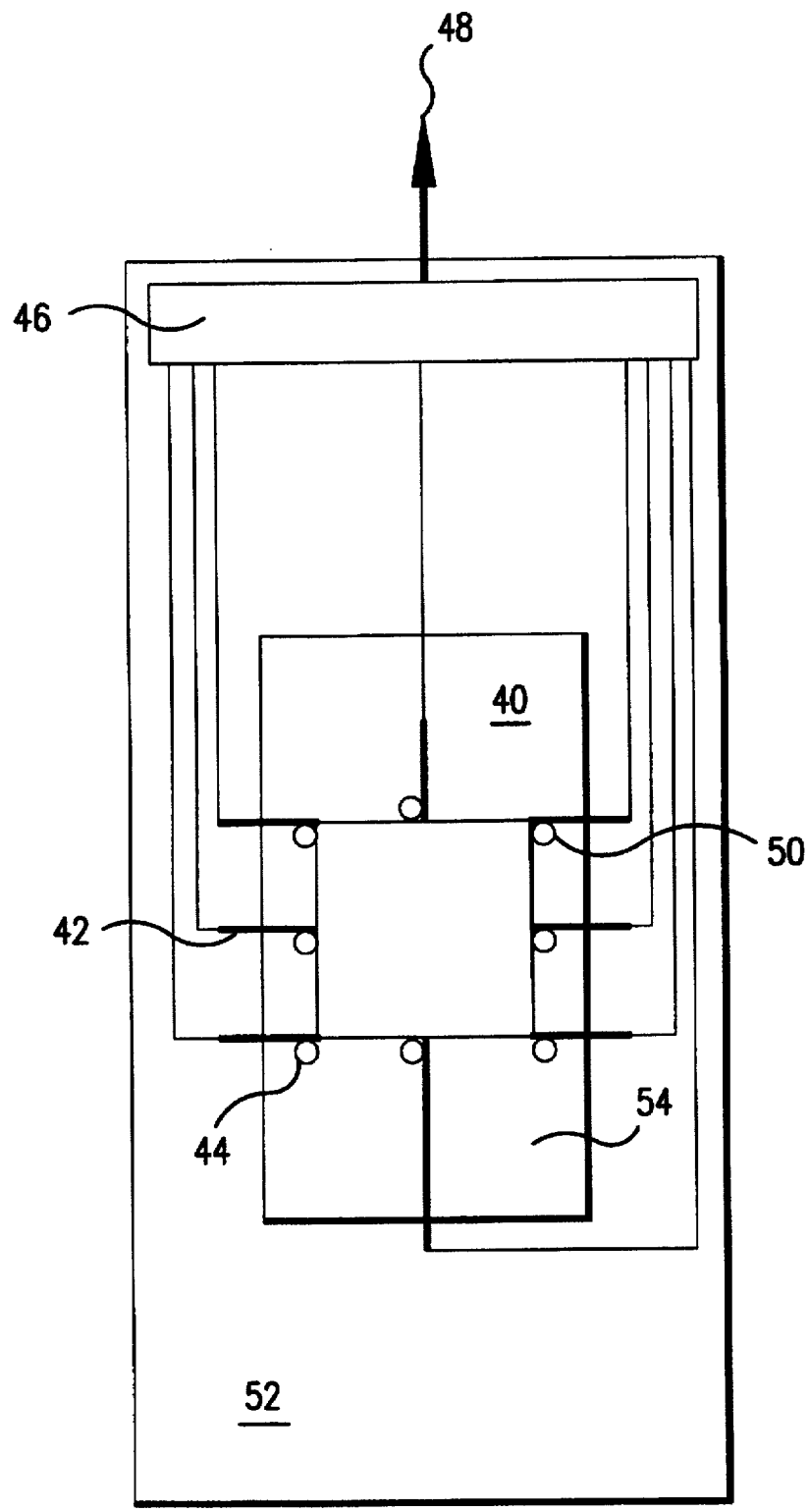

Described herein are methods and compositions for characterizing and manipulating individual nucleic acid molecules, including mammalian chromosome-sized individual nucleic acid molecules. The methods and compositions described herein can be utilized for optical mapping and optical sequencing purpose to generate accurate, rapid, high throughput analyses of nucleic acid molecules at the genome level.

Specifically, Section 5.1 describes methods for the elongation and fixation of single nucleic acid molecules. Such methods include both agarose-based (Section 5.1.1) and solid surface-based (Section 5.1.2) techniques. Section 5.1 also describes assays for the optimization of parameters important to the production of the solid, planar surfaces used-herein. Further, Section 5.1 also describes flow-based elongation techniques (Section 5.1.3) in which a single nucleic acid molecule is elongated, manipulated and/or analyzed in a laminar flow elongation device.

Section 5.2 describes methods for the imaging and sizing of single nucleic acid molecules. The Section includes, for example, nucleic acid staining, microscopy and photography techniques useful for imaging single nucleic acid molecules. Further, the Section describes methods for the sizing of single nucleic acid molecules including both static and dynamic measurement techniques. Section 5.3 describes genome analysis applications to which the single nucleic acid molecule techniques of the invention may be put. Such applications include, for example, optical mapping and optical sequencing techniques. Finally, Section 5.4 discusses methods for rapid, high throughput utilization of the single nucleic acid techniques of the invention.

5.1. SINGLE NUCLEIC ACID MOLECULE ELONGATION TECHNIQUES

A variety of methods can be utilized for the rapid, controllable and reproducible elongation of single nucleic acid molecules in such a manner that allows rapid, efficient analysis and/or manipulation of the molecules. These techniques can include, for example, gel-based (Section 5.1.1), solid surface-based (Section 5.1.2) and flow-based techniques (Section 5.1.3), each of which will be separately described below.

5.1.1. GEL-BASED TECHNIQUES

Gel-based techniques can be utilized for the elongation of single nucleic acid molecules. The gel-based techniques described herein maintain the biological function of the nucleic acid molecules and, further, allow for the manipulation and/or accurate analysis of the elongated single nucleic acid molecules. Nucleic acid molecules which can be rapidly, efficiently analyzed via such gel-based techniary include nucleic acid molecules which range in length from about 20 kb up to mammalian chromosome-sized lengths (i.e. greater than 1000 kb). Further, such gel-based techniques make possible the utilization of dynamic measurement procedures, may generate a lower level of nucleic acid shearing and make possible the utilization of a wide range of biochemical activities with which the manipulate the elongated nucleic acid molecules.

Briefly, gel-based techniques involve elongating single nucleic acid molecules within a molten or nonpolymerized gel composition such that upon cooling or polymerization, the elongated nucleic acid molecules are maintained in a relatively stationary position, while remaining accessible to, for example, enzymatic manipulation and/or hybridization to complementary nucleic acid molecules or binding to sequence-specific proteins or peptides. Further, the gelation process restrains elongated nucleic acid molecules from appreciably relaxing to a random coil conformation after, for example, their enzymatic cleavage.

For optimal imaging and manipulation potential, the amount which the single nucleic acid molecules are elongated within the gel composition is critical. Excessive elongation or stretching causes the molecule to become difficult to visualize. For example, too much stretching presents too little fluorochrome per imaging pixel, lending the intensities generated by the measured molecular intensities to approach background values. Insufficient stretching, however, generates too low a level of tension, which can interfere with an analysis of single nucleic acid molecule manipulations. For example, when restriction mapping, enough elongation must occur such that, upon digestion, the newly formed nucleic acid fragments pull away from each other, thus revealing restriction sites. An additional requirement for optimal gel-based elongation requires that care be taken to preserve the moisture within the gel, such that the maximum biological function of the nucleic acid can be retained.

For optimal imaging/manipulation potential, the extent to which a nucleic acid molecule is elongated within a gel must be great enough to generate a sufficient level of intramolecular tension while not being so great that the elongated molecule becomes difficult to image. In general, elongation methods which produce single nucleic acid molecules that span approximately 20% to 60% of their curvilnear contour lengths are preferred.

Further, the elongated nucleic acid molecules within the gel must lie within a shallow plane of focus for successful imaging. With respect to larger nucleic acid molecules, for example, it is additionally important for the molecules to lie within a plane approximately 0.2 µm in thickness for focused visualization.

Because gelation or polymerization fixes embedded molecules, systematically varying parameters which affect the rate at which the gelation or polymerization can modulate the degree of fixation and, ultimately, the rate of molecule relaxation. Smaller nucleic acid molecules (i.e., molecules less than about 350 kb) relax quickly. Thus, it is preferred that elongation take place under conditions which hasten gelation/polymerization so that the nucleic acid molecules become trapped in an extended conformation before substantial relaxation takes place. Larger nucleic acid molecules relax at a slower rate, and, therefore, can be elongated under conditions which allow for a slower rate of gelation/polymerization.

With respect to agarose gels, parameters which affect the rate of gelation include, for example, the gel concentration and/or temperature at which the gel is formed. A higher gel concentration or gelation at a low temperature hastens gel formation. With respect to polyacrylamide gels, parameters which affect the rate of polymerization include, for example, the acrylamide/bisacrylamide concentration and ratio, the temperature at which polymerization takes place, and the ammonium sulfate and TEMED concentrations used.

While any gel composition may be used for such elongation techniques, an agarose gel composition is preferred, with an agarose composition exhibiting a low gelling temperature being especially preferred. Such low gelling temperature agarose compositions are the most optically clear agarose compositions available and, further, because such compositions can remain molten at 37° C., the biological activity of enzymes, such as restriction enzymes, within the molten agarose can easily be maintained. Additionally, such agarose compositions are useful in that rapid gelation is often desired for fixation of the elongated nucleic acid molecules. For agarose gel compositions, a gel composition comprising from about 0.1% to about 3.0%, with 0.1–1.5% being preferred.

Any number of techniques can be used to apply an external force which will cause the nucleic acid molecules within the gel composition to become elongated. For example, an elongating external force may include an electrical or mechanical force. While the exact amount of external force required for optimal elongation may vary according to, for example, the specific gel composition and nucleic acid molecules being elongated, the optimization of gel parameters can easily and without undue experimentation be assayed by, for example, utilizing the visualization and measurement techniques described in Section 5.2, below.

Elongation may, for example, be accomplished by generating a flow force within a molten agarose gel containing single nucleic acid molecules. Such a flow force may be set up by placing the nucleic acid/molten gel composition between two solid surfaces, such as, for example, between a slide and a coverslip. In such an embodiment, a hole preferably exists in the slide through which reagents for the manipulation of the elongated nucleic acid molecules can be introduced into the gel. Alternatively, molecules may be elongated by pressing the nucleic acid/molten gel composition under, for example, a teflon stamp, as described in Section 5.4, below.

An electrical force may, additionally, be generated via any standard electrophoretic method, including, for example, pulsed field (U.S. Pat. No. 4,695,548) and pulsed oriented (POE) electrophoresis. When utilizing electrophoretic techniques, devices which are suitable for visualization by microscopy techniques are preferred. One such embodiment is the miniature POE device shown in FIGS. 1 and 2 and in Example 4, below.

POE improves separation of polydisperse polymer molecules in a sample by using short electric pulses to create and vary field angles, with the effective field angle being defined by the vector sum of a series of pulses which may vary in duration, intensity and direction. Pulse times and pulse intensities are modulated to effect separation. POE is also useful for creating effective field angles during imaging. The needed instrumentation is readily adapted to the microscope.

Figure 2:
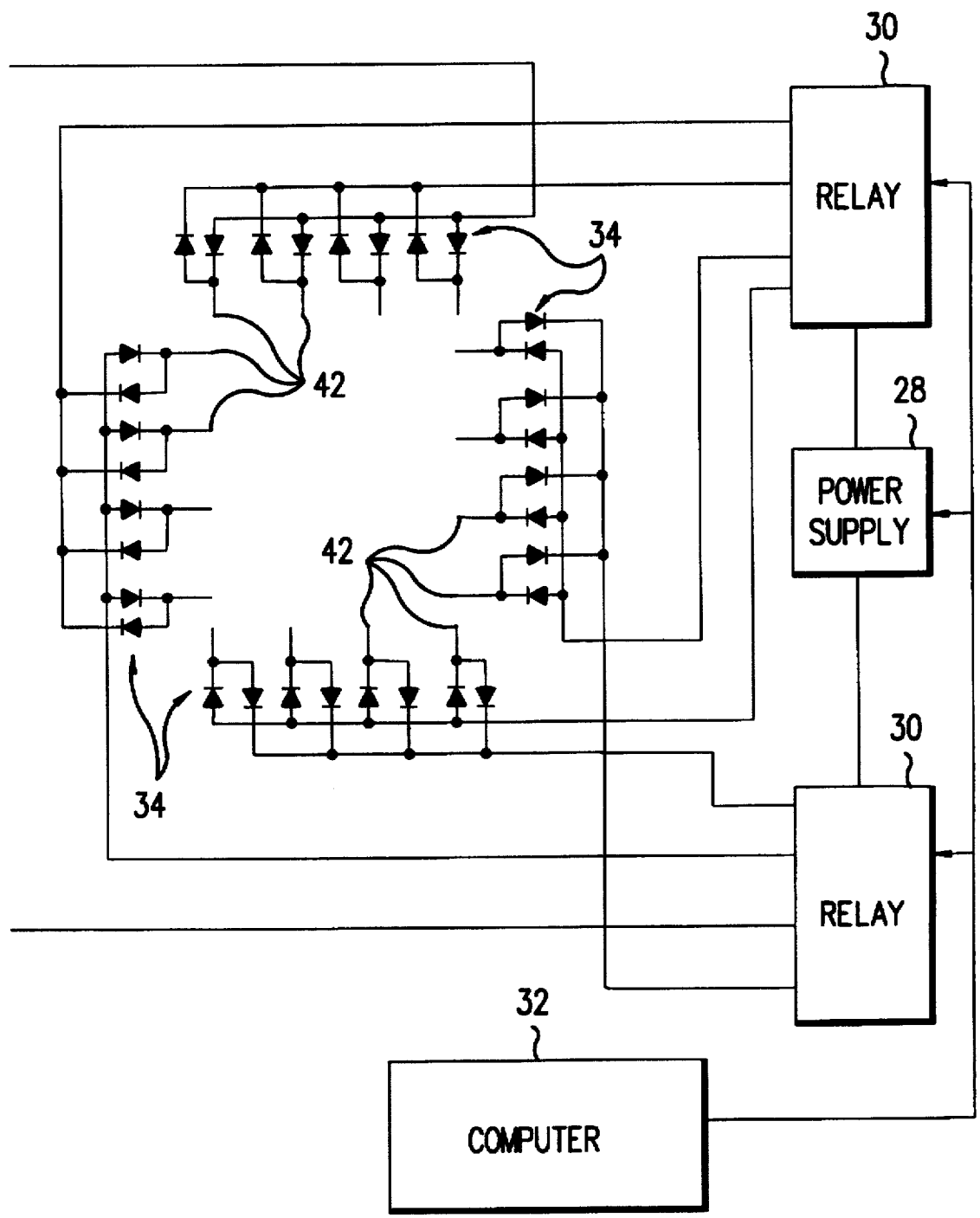

An exemplary laboratory instrument for POE is illustrated in FIG. 1 and a schematic view is shown in FIG. 2.

The instrument exemplified in FIG. 1 is similar to a miniature version of that described in U.S. Pat. No. 4,473,452, but differs in that the POE instrument has two sets of diodes 34 which enable bipolar operation of the discrete electrode array. The diodes 34 can be replaced by a multi-ganged relay (not shown) to provide similar electrical isolation. However, it is best to use the diodes 34 when very fast (less than 1 second) pulsing is needed.

As depicted in FIGS. 1 and 2, the miniature electrophoresis chamber 50 used in this invention measures about the size of a standard coverslip. It has electrodes 42', which are connected to diodes 34 (FIG. 2). In order to generate the desired electric fields, platinum electrodes 42' are interconnected as shown in FIG. 2. In particular, d-c power supply 28 supplies d-c power to relays 30, which are controlled by a computer 32 to connect selected outputs to the d-c power from power supply 28. Computer 32 also controls d-c power supply 28 so that the potential of the power supply can be varied. Outputs to relays 30 are connected to electrodes 42' through respective diodes 34 for each electrode.

As shown in FIG. 1, the miniature POE apparatus has a holder 52, which fits on a microscope stage. A slide 54, which holds an agarose gel, is placed into the holder and the electrodes 42 make electrical contact with the slide/gel/cover-slip sandwich placing drops of 30% glycerol-agarose at the agarose electrical connecting wicks 44. The glycerol prevents drying out of the gel. The electrical connector 46, which is part of the holder 52, provides a link to the bipolar diodes 34 and pulsing instrumentation shown in FIG. 2.

As in the case of the instrument described in U.S. Pat. No. 4,473,452, the presently exemplified instrument generates electrical fields which are orthogonal to each other, which alternate between high and low intensities out of phase with each other according to the chosen pulsing routine as described below and which translate the molecules undergoing separation incrementally through the gel matrix in an overall direction transverse to the respective directions of the generated electrical fields. Due to the novel bipolar nature of the electrode design, it is possible to change polarities, simultaneously if desired, in addition to alternating high and low intensities without any significant electrode induced field distortions.

The determination of effective field angle by a pulsing routine rather than by placement of an electrode array permits molecular orientations (and separations) that would otherwise be difficult. As described in Example 4 below, POE has been used in DNA imaging experiments. The electrophoresis apparatus pictured in FIGS. 1 and 2 and used in Example 4 may be preferred over that of U.S. Pat. No. 4,695,548 because varying the field angle by moving electrodes as taught by conventional pulsed field electrophoresis is not practical due to microscope stage physical constraints.

As described above, gel-based techniques can successfully analyze single nucleic acid molecules ranging in size from approximately 20 kb up to chromosome-sized (i.e. greater than 1000 kb). Thus, techniques for the preparation oft he single nucleic acid molecules to be elongated should be chosen which avoid excessive shearing. Such techniques are well known to those of skill in the art and may include, for example, techniques such as those described below.

First, agarose-embedded cell lysate techniques, such as those described in U.S. Pat. No. 4,695,548, for preparing large DNA molecules without breakage can be adapted for use with the gel-based elongation techniques of the present invention. For example, cells may be washed, mixed with molten low melt agarose, which is then allowed to harden. The resulting block them placed into a lysis solution containing EDTA, protease and detergent, which diffuses into block, lysing the cells and rendering intact naked DNA molecules stripped of their associated proteins. The absence of physical manipulation keeps the DNA essentially intact. The agarose can then be melted and subjected to external elongating forces such as those described above. Alternatively, chromosomal DNA can first be resolved into chromosomal populations via standard methods such as, for example, pulsed field electrophoresis. The resolved DNA populations which may, for example, consist of populations of copies of the same chromosome, can then be subjected to the gel-based elongation methods described above.

Additionally, a condensation agent may be used to collapse gel-bound nucleic acid molecules into small, shear-resistant balls, that can be unfolded with the addition of an ionic compound, such as, for example, sodium chloride or magnesium chloride, when appropriate. Preferably, the condensation agent is spermine. The spermine protocol, which is described further in Example 10, permits the mounting of extremely long DNA molecules with no detectable shear-mediated breakage. Nucleic acid molecules of extremely long length (i.e., about 5.6 Mb) have been successfully condensed by such a technique with no appreciable shearing. In fact, it is conceivable that any size of nucleic acid can be inserted into a gel with no substantial shearing. While the Use of spermine is preferred, other suitable materials for collapsing such nucleic acid molecules include any material which can cause a particular nucleic acid molecule to collapse, e.g., any condensation agent which causes nucleic acid molecules to preferentially solvate themselves. Additional examples of such materials include, but are not limited to, spermidine, alcohol and hexamine cobalt. Spermine-condensed DNA can be added to molten agarose, decondensed, and elongated according to the techniques described herein. Further, large nucleic acid molecules may initially be separating electrophoretically using, for example standard pulsed field electrophoresis techniques. The portion of the gel containing the separated molecules of interest may then be excised.

The excised portion of the gel can then be used as part of the gel-based techniques of this Section. Additionally, nucleic acid molecules in solution can be gently mixed with a molten agarose solution and utilized as part of the techniques of this Section.

Once single nucleic acid molecules have been satisfactorily elongated and fixed within the gel compositions as discussed herein, any of the analysis and/or manipulation techniques described in Section 5.3, below may routinely be utilized.

5.1.2. SOLID SURFACE-BASED TECHNIQUES

Solid surface-based techniques can be utilized for the rapid, controllable and reproducible elongation and fixation of single nucleic acid molecules, as described in this Section. Upon elongation and fixation of the single nucleic acid molecules onto the solid surfaces as described herein, any of the analysis and/or manipulation techniques discussed, below, in Section 5.3, may easily be performed.

Such solid surface-based elongation/fixation techniques yield a number of advantages for single nucleic acid analysis/manipulation applications. For example, the nucleic acid molecule images are very sharp and bright. This is due, in part, to the absence of gel-based image scattering, and to less extraneous fluorescence background in the field. Additionally, fixation techniques can be more precisely controlled and may, for example, be made somewhat tighter than those described, above, in Section 5.1.1, for gel-based techniques. Thus, the solid surface-based techniques described herein make possible the rapid generation of high resolution nucleic acid analysis information from single nucleic acid molecules, including single nucleic acid molecules of much shorter lengths than currently available using the gel-based techniques described, above, in Section 5.1.1.

A wide size range of nucleic acid molecules, i.e., from about 300 bp to mammalian chromosome-size (that is greater than 1000 kb) can efficiently be elongated and stably fixed onto the solid surfaces described herein. These techniques feature gentle fixation approaches which maintain the biological function of the nucleic acid molecules being elongated and, further, allow for the manipulation and/or accurate analysis of the elongated single nucleic acid molecules. Additionally, the solid surface-based techniques described herein make possible the storage and reuse of the elongated nucleic acid molecules. Further, such solid surface-based techniques described herein can easily be adapted for high throughput methods, as described in Section 5.4, below.

The elongation procedures described in this Section utilize solid surfaces which exhibit a positive charge density, as described, below, in Section 5.1.2.B, below. As discussed, below, in Section 5.1.2.A, however, the density of the solid surface positive charge must be optimized to achieve a balance between elongation, relaxation, stability and biological activity parameters.

5.1.2.1. SOLID SURFACE OPTIMIZATION

Unlike instances in the past in which nucleic acid molecules were attached to solid surfaces, the controlled, reproducible solid surface elongation/fixation techniques described herein utilize surfaces, especially glass surfaces, which reproducibly elongate and fix single nucleic acid molecules. As discussed in greater detail, below, in Section 5.1.2.2, the surfaces described herein exhibit a positive charge density. Several parameters must be taken into account, however, in order to optimize the solid surface charge density such that, for example, the genome analysis techniques described, below, in Section 5.3, can be performed.

The solid surfaces of the invention should exhibit a positive charge density which achieves an optimal balance between several parameters, including elongation, relaxation, stability and biological activity. Assays are described in this Section which make surface optimization possible.

First, the solid surface must allow the molecule to be as completely elongated as possible, while allowing for a small degree of relaxation. As used herein, "small degree of relaxation" refers to a level of relaxation which yields a gap of between about 0.5 microns and about 5.0 microns when the elongated nucleic acid molecule is cut. An optimal balance between these two parameters yields improved imaging capability. For example, an efficient balance between elongation and relaxation capability facilitates the imaging of newly formed, growing gaps as develop at restriction enzyme cleavage sites.

In addition to elongation and relaxation, the biological activity retained by the elongated nucleic acid molecule must be taken into account when optimizing the positive charge density of the elongation/fixation solid surface. Further, the stability of the elongated nucleic acid molecules on the surface must be considered. In the case of a restriction digest (i.e., as part of an optical mapping procedure), "stability" refers to how well the restriction fragments formed are retained on the solid surface.

As a first step toward determining the positive charge density which represents an optimal balance between each of these parameters, the positive charge density (e.g., the level of surface derivatization; see Section 5.1.2.2, below) may be titrated against the measured average molecular length of the nucleic acid molecules which are deposited on the surface. Molecule counts (i.e., the number of countable molecules which have been deposited) on the surface can also be measured.

At low levels of positive charge density (e.g., derivatization), the average molecular extension on the surface is low. This may be due to the fact that, at this charge concentration, not enough nucleic acid binding sites exist to hold an extended molecule with stability. As the positive charge density (e.g., the level of derivatization) increases, the average nucleic acid molecular extension also increases, eventually peaking. As the positive charge density (e.g., the amount of derivatization) continues to further increase, the average amount of molecular extension then begins to decrease. This may be due to the presence of such an abundance of nucleic acid binding sites that any flow forces which are present and would drive elongation are overwhelmed and, therefore, molecular extension is, to some extent, quenched.

Once a positive charge density (e.g., a derivatization level) is achieved which affords maximum nucleic acid molecule extension, the elongation parameters must be tested within the context of the specific imaging or analysis procedure for which the single molecules are to be used. Such testing involves an evaluation of the biological activity of the nucleic acid molecule as well as a determination of the relaxation level of the elongation nucleic acid. For example, in instances whereby the elongated nucleic acid molecules are to be used for optical restriction mapping, the level of elongation/fixation must allow for cutting by the restriction enzyme as well as providing a level of relaxation which makes possible the ready imaging of nascent restriction enzyme cleavage sites.

In the case of optical mapping, one such test would include the digestion of the elongated nucleic acid molecule and a determination of first, the enzyme's cutting efficiency, and, second, a measurement of the size of the nascent gap formed at the new cleavage sites (thus measuring relaxation). A cutting efficiency of at least about 50% is an acceptable level of biological activity retention. Acceptable relaxation levels are as described above.

Further, the stability of the elongated nucleic acid molecule must be ascertained. As discussed above, in the case of optical mapping, stability refers to the retention level of newly formed restriction fragments on the surface. For optical mapping, an acceptable stability level is one in which at least about 80% of the newly formed restriction fragments.

5.1.2.2. SOLID SURFACE POSITIVE CHARGE DENSITY

Solid planar surfaces may be prepared for optimal elongation and fixation of single nucleic acid molecules via a variety of simple manipulations. First, for example, the surfaces may be derivatized to yield a positive charge density, which can be optimized by utilizing the assays described in Section 5.1.2.1, above. Additionally, simple manipulations may be performed to reversibly modulate the surface positive charge density to more precisely optimize surface charge density at each step of the nucleic acid elongation, fixation analysis and/or manipulation steps. Such reversible charge density modulation is referred to herein as "faculatiative fixation", as discussed below. Third, additional methods for further affecting the elongation/fixation of the single nucleic acid molecules are discussed. These include, for example, methods for controlled drying, for the generation of gradients of positive charge density and for crosslinking of the elongated nucleic acid molecules.

5.1.2.2.1. SURFACE DERIVATIZATION

Surfaces may be derivatized using any procedure which creates a positive charge density which, presumably, favors an interaction with a nucleic acid molecule. Any compound which absorbs to or covalently binds the surface of interest and, further, introduces a positive charge density onto the surface can be utilized as a derivatizing agent. Such compounds should not, preferably fluoresce. For example, surfaces may be derivatized with amino moiety-containing compounds that absorb to or covalently bind the surface of interest. Such amino-containing compounds can, for example, include amino-containing silane compounds, which are capable of covalently binding to surfaces such as glass. Among these amino-containing silane compounds are 3-aminopropyltriethoxysilane (APTES) 3-methylaminosilane. APTES can be useful in that it may be crosslinked (see below, e.g.), while the use of 3-methylaminosilane may, in certain instance, be advantageous in that the compound resists oxidation.

Among those derivatizing agents which non-covalently absorb to surfaces, such as glass surfaces may, for example, be derivatized with poly-D-lysine (polylysine). Polylysine binds glass via electrostatic interactions. Polylysine may be especially advantageous for pressure-based elongation techniques (see Section 5.1.2.3, below). When utilizing polylysine as a derivatizing agent, the size of the polymeric polylysine is to be taken into account. For example, low molecular weight polylysine (e.g., mw less than 200,000; with about 90,0000 being preferred) appears to fix elongated nucleic acids more tightly than high molecular weight polylysine (e.g., mw greater than 200,000, with 500,000 being preferred). Thus, when elongating and fixating on a solid surface which having polylysine, a low molecular weight polylysine would be preferred for tighter fixation, e.g., for the fixation of smaller nucleic acid fragments.

Surface derivatization may be achieved by utilizing simple, reproducible techniques. When derivatizing a surface with APTES, for example, a clean surface, such as a glass surface, may be incubated in an acidic APTES solution for a given period of time. Increasing the incubation time will increase the resulting charge density of the surface. It is preferred that conditions should be chosen such that the single nucleic acid molecules are elongated to approximately 50–100% of their polymer contour length.

In one embodiment of such an APTES derivatization procedure, a clean glass surface can be incubated for an appropriate period of time in an APTES concentration of about 0.10M, pH 3.5 at a temperature of about 65° C. Incubation times for such an embodiment can range from about 3 to about 18 hours. In order to stop the derivatization process, the surfaces need only be removed from the APTES solution and repeatedly rinsed in highly pure water. Clean, derivatized coverslips are then air dried.

With respect to derivatizing a surface with polylysine, a clean surface, such as a glass surface, can be derivatized in a polylysine solution. The concentration and molecular weight of the polylysine used for derivatization affect the level of derivatization achieved per incubation time. Increasing the polylysine concentration increases the resulting surface charge density which forms. For optical mapping purposes, conditions should be chosen such that single nucleic acid molecules are extended up to about 100% of their polymer contour length.

In one embodiment of such a polylysine derivatization method, a clean glass surface can be incubated overnight, at room temperature, in a solution of polylysine having a molecular weight of about 350,000, at a concentration of about $10^{-6}$ to $10^{-7}$ grams per milliliter. After incubation, the derivatized glass surface is rinsed in highly pure water and either air dried or wiped dry with lens tissue paper. Such conditions are expected to achieve nucleic acid elongation levels which are suitable for, say, optical restriction mapping.

In addition to methods which involve the use of a derivatizing agent such as described above, a positive charge density may be introduced onto a surface by a number of alternate means. Such a positive charge density may, for example successfully be applied to a surface via plasma derivatization, an electrostatic generator (to create electrical charge) or corona discharge, just to name a few.

5.1.2.2.2. FACULTATIVE FIXATION

Described herein are methods for the reversible modulation of solid surface positive charge density. Such methods are designed to optimize solid surface charge density at each step of the elongation, fixation and analysis/manipulation steps described herein. Among the ways by which such a reversible charge density can be effected include changes in the salt concentration, divalent cation concentration, effective water concentration, and/or pH.

Using facultative fixation, the surface positive charge density can be tailored to suit each step of the single nucleic acid techniques described herein. For example, it may be desirable to fix the nucleic acid molecule under reversible conditions which favor a loose charge density, leading to a higher degree of nucleic acid molecule spreading. The charge density may then, for example, be increased for a restriction digest step. Additionally, it may be desirable to digest a molecule so tightly fixed that no relaxation gaps form upon cleavage and then to subsequently lower the charge density such that the gaps are allowed to form. Finally, a very high charge density may then be chosen if the sample is to be stored (i.e., such that the newly formed restriction fragments do not detach from the surface during storage).

With respect to salt concentration, as the salt concentration the surface finds itself in increases (e.g., from 0 to 5M NaCl), the surface positive charge density decreases. With respect to divalent cation (e.g., $Mg^{2+}$, $Ca^{2+}$) concentration, as the divalent cation concentration in the buffer surrounding the surface increases (e.g., 1 mM to 1M), the surface positive charge density decreases. As the effective water concentration is decreased, due to the addition of an increasing concentration of non-aqueous material, the surface positive charge density increases.

Changing the pH represents a gentle and fast method to reversibly modulate the charge density of a surface. A low pH promotes positively charged environment, while a high pH promotes a less positively charged, more neutral environment.

Taking, as an example, a surface which has been derivatized using an amino-containing group, an aminosilane compound, for example, a pH of approximately 6 yields a positive charge density. Raising the pH lowers the charge density until the charge is essentially neutral at a pH of 9–10. A variety of simple methods may be utilized to produce pH-based facultative fixation. For example, the surface can be exposed to buffers, such as Tris or phosphate buffers, of varying pH. Additionally, gas-induced pH changes can be made. For example, $CO_2$ gas can be introduced over the buffer in which the derivatized surface is submerged such that the buffer is acidifies, thereby increasing the overall charge density on the surface. Alternatively ammonia gas, for example, may be introduced over the buffer, raising the buffer pH, thereby lowering the overall surface charge density. These latter gas-based techniques are especially useful in instances whereby it is essential to minimize possible physical disturbances on the solid surface in that the buffer remains undisturbed throughout the facultative fixation process.

5.1.2.2.3. OTHER POSITIVE CHARGE DENSITY METHODS

Derivatization gradients. In addition to a uniform, controllable derivatization of an entire solid surface, it is also possible to reproducibly form a gradient of derivatization. Such a derivatization gradient can be formed by, for example, the use of drops of derivatizing agents deposited on the solid surface. Upon deposition, such a drop would form a meniscus, leading to a greater concentration of derivatizing agent available to the solid surface at the perimeter of the drop than within its interior section. This, in turn, leads to a gradient of derivatization, with the outer portion of the solid surface where the drop had been exhibiting a higher level of derivatization than that within the interior.

Such a gradient of derivatization promotes a higher percentage of fully elongated molecules. Further, due to the tension set up across the nucleic acid molecule, a more efficient level of aligning and packing is observed, thus maximizing the amount of usable molecules per imaging field, one goal of invention.

Crosslinking. The single elongated nucleic acid molecules of the invention may, additionally, be crosslinked to the solid surface. Such crosslinking serves to permanently fix the molecules to the surface, which can be advantageous for a variety of reasons. For example, crosslinking may be useful when working with very large nucleic acid molecules. Further, the surface properties of the solid may be modulated with no possibility of nucleic acid loss. Additionally, the possibility of unacceptable nucleic acid fragment loss or relaxation which could occur over the course of, for example, storage or a long reaction, would not exist with crosslinking.

Crosslinking, as utilized herein, is to be performed in conjunction with the elongation/fixation techniques described in these Sections. First, the desired level of elongation is determined and achieved, and subsequent to this, the elongated nucleic acid is crosslinked for permanent fixation.

A number of crosslinking methods are available, including glutaraldehyde and UV crosslinking. Glutaraldehyde crosslinking may be performed using, for example, via 5 minute incubation in a 10 mM glutaraldehye solution. UV crosslinking may be accomplished using, for example, a Stratalinker (Stratagens) crosslinker, following standard protocols.

Controlled Drying. Additional compounds may be added to the aqueous solution by which the nucleic acids may be deposited onto the solid surfaces (see below for deposition techniques) which yield drying characteristics that promote the production of a greater percentage of fully elongated nucleic acid molecules and which exhibit a lower level of intermolecular overlap or tangling, both features of which are extremely useful for analysis purposes.

Compounds which may be added for such a controlled drying aspect of the elongation methods include, but are not limited to glycerol, DMSO, alcohols, sucrose, neutral polymers such as Ficoll, and dextran sulfate. While their mechanism is not known, it is possible that these compounds promote a liquid crystalline state which promotes the above-described features.

Hydrophobic microwells. Hydrophobic regions may be introduced onto portions of the solid surfaces which can serve as, essentially, "microwells". These hydrophobic regions create closed boundaries, which make possible the introduction of different reagents onto different portions of the solid surface, such that a number of different reactions may be performed simultaneously on the same solid surface.

Prefixation techniques. The solid surfaces of the invention may, be premixed with agents, proteins for example, of interest, prior to the introduction of the nucleic acid molecules top be elongated. Proteins may be fixed onto the solid surfaces by routine means, such as crosslinking means, which are well known to the skilled artisan. Among the proteins which may be prefixed onto the solid surfaces of the invention are enzymes, such as restriction enzymes, which are used to manipulate nucleic acid molecules or any other nucleic acid-binding proteins. Thus, upon elongation of nucleic acid molecules onto the solid surfaces containing such prefixed enzymes and the addition of whatever additional agents, such as certain divalent ions, which are necessary for the enzymes to act upon nucleic acids, the single nucleic acid molecules can be manipulated, for example, cleaved at appropriate restriction sites. Using such a prefixation technique, a number of different reactions may be performed simultaneously on the same surface.

5.1.2.3. SINGLE NUCLEIC ACID MOLECULE DEPOSITION

As described above, a wide size range of nucleic acid molecules may be deposited onto the derivatized solid surfaces described herein. Specifically, nucleic acid molecules from about 300 base pairs to greater than 1000 kb can be analyzed using such solid surfaces. Smaller nucleic acid molecules, which are relatively shear resistant, can be isolated using standard nucleic acid purification techniques well known to those of skill in the art. These smaller nucleic acid molecules may be less than about 150 kb and, generally, are less than about 20 kb. Larger nucleic acid molecules, which are subject to breakage by shearing events, can be isolated by utilizing, for example, the nucleic acid molecule isolation techniques described, above, in Section 5.1. Such shear-sensitive nucleic acid molecules are generally greater than 150 kb, but may include molecules greater than about 20 kb.

Larger nucleic acid molecules (i.e., those greater than about 90 kb) should, generally, be deposited onto the solid surfaces in a manner which minimizes breakage due to shear forces. Preferably, therefore, these larger nucleic acid molecules are deposited onto the surfaces in molten agarose. For example, molten agarose containing nucleic acid molecules can be spread onto surface under conditions which generates a flow force that facilitates elongation. In a preferred embodiment, drops or droplets of molten agarose containing nucleic acid molecules are deposited onto the surface. The force generated when the drop hits the surface is sufficient to provide the required elongation. Upon hardening, the agarose is scraped off the surface, leaving behind intact, elongated fixed nucleic acid molecules.

In instances in which smaller nucleic acid molecules (i.e., ones ranging from about 300 bp to about 90 kb) are being deposited, the above gel techniques can be utilized. Further, the nucleic acid molecules can be deposited onto the surface in an aqueous solution. Elongation can then be achieved via various methods. For example, molecules can be sandwiched between two surfaces, one of which is the derivatized surface. In such a procedure, one of the two surfaces should contain a hole through which reagents may be introduced. Alternatively, the solution on the derivatized surface containing the nucleic acid molecules can be pressed with, for example, a teflon stamp.

Preferably, however, the nucleic acid molecules deposited in such an aqueous fashion can be elongated by merely allowing the aqueous solution to dry. Thus, in the absence of any manipulations apart from simple deposition onto a derivatized surface of the invention, single nucleic acid molecules can efficiently, successfully and rapidly generate stably elongated and fixed nucleic acid molecules suitable for imaging and/or further manipulation. As described, below, in Section 5.4, such a technique is especially suited to high throughput analysis techniques.

5.1.3. FLOW-BASED TECHNIQUES

The single nucleic acid molecules of the invention may be elongated manipulated and/or analyzed in flow-based techniques such as those described in this Section. Such techniques may be especially useful in instances whereby only low concentrations of the nucleic acid molecules of interest are available.

Briefly, such a flow-based technique involves the introduction of a single nucleic acid molecule into a laminar flow elongation device. Gentle solvent flow fields are generated within the device which cause the nucleic acid molecules to be elongated without significant shearing. Further, as the elongated nucleic acid molecule flows through the laminar flow elongation device, it can be imaged via, for example an attached microscope and camera. Still further, the methods described herein make possible the controlled, regio-specific restriction digests of the elongated nucleic acid molecules which, coupled with the flow aspect of the device, makes possible the generation of real-time restriction maps.

Figure 25:
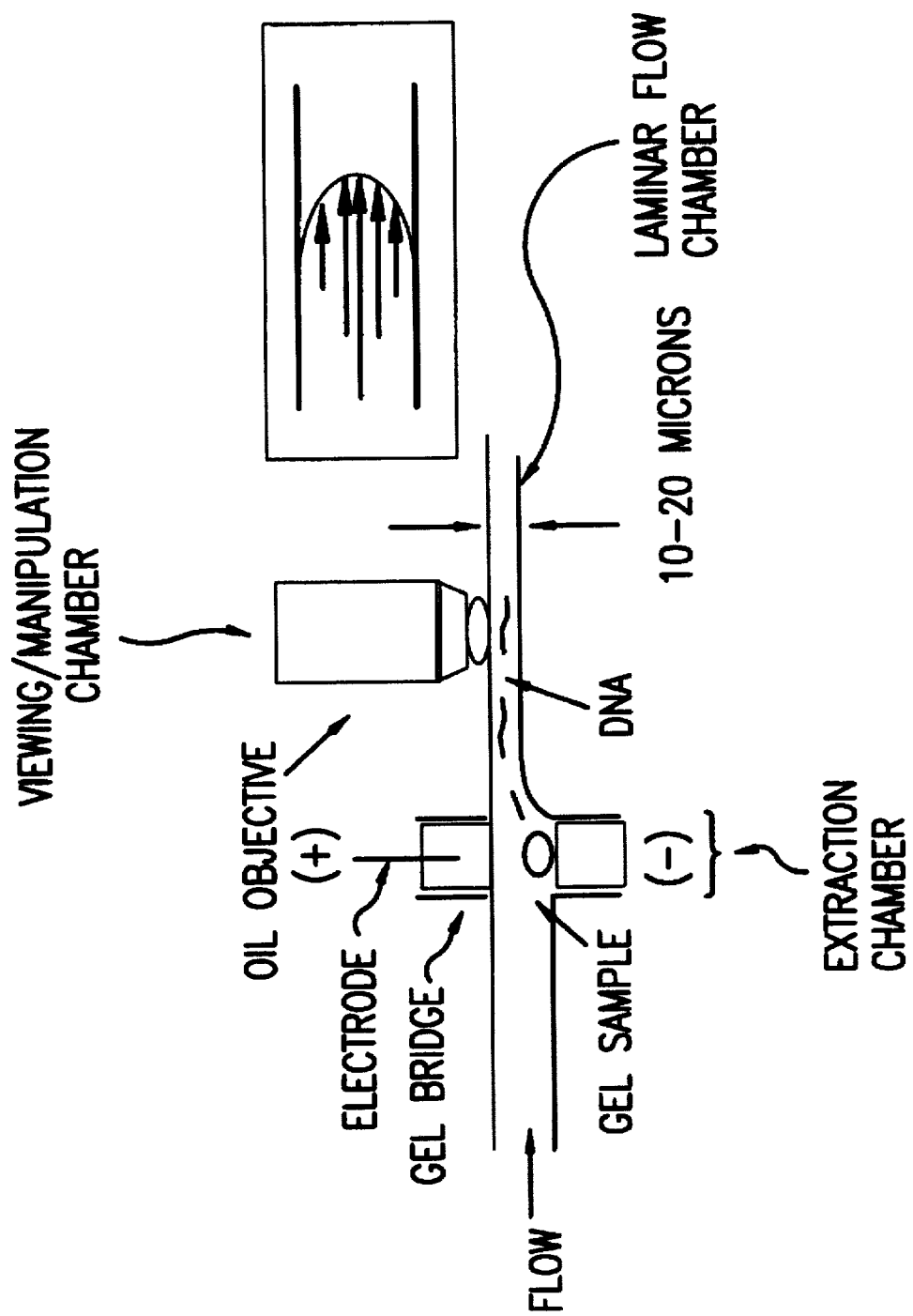

A preferred embodiment of such a laminar flow elongation device is illustrated in FIG. 25. Briefly, such a device, which is designed to liberate and elongate nucleic acid molecules out of gel inserts, comprises a laminar flow chamber to which are attached an extraction area and a viewing/manipulation area. While the device diagrammed in FIG. 25 depicts a single laminar flow chamber, a multiplexing laminar flow elongation device may also be utilized. Such a device may contain, for example, a branched laminar flow chamber, such that multiple analyses of copies of identical single nucleic acids can be accomplished rapidly.

The laminar flow chamber should contain a thin space, for example, a space generated via a 10–20 micron opening. The solvent flow generated within the chamber should be gentle enough to avoid significant shearing of the nucleic acid molecules. For example, one acceptable flow would be approximately $5 \times 10^{-2}$ nl/sec at 100×20 micron opening. The fluid flow may be generated by a pumping means attached to the chamber upstream of the extraction and the viewing/manipulation areas or, alternatively, may be generated by a vacuum means attached to the chamber downstream of the extraction and the viewing/manipulation areas.

The extraction chamber, through which the laminar flow chamber passes, serves to simultaneously liberate the nucleic acid from a gel insert and to move the nucleic acid into the flow of the device. Such an extraction chamber comprises electrodes which set up an electric field through which the nucleic acid moves out of the insert and into the flow of the laminar flow chamber.

The viewing/manipulation chamber comprises a microscope/light source mounted chamber through which the laminar flow chamber passes. The microscope is preferably an epifluoresence microscope containing an oil immersion objective, to which is attached a camera, preferably a video camera. The elongated nucleic acid molecules can be visualized and, optionally, their images can be recorded, as the molecule passes through the viewing/manipulation chamber.

In a preferred embodiment of such a procedure, the nucleic acid molecules are enzymatically manipulated as they pass through the viewing/manipulation chamber. Taking the case of optical mapping as an example, the elongated, flowing nucleic acid molecules can be digested with restriction enzymes as they pass through the viewing/manipulation chamber.

For example, the fluid in the laminar flow chamber can contain restriction enzymes and each of the reagents necessary for digesting the nucleic acid molecule flowing through the chamber, except that the divalent cation (usually $Mg^{2+}$) which is necessary for enzyme activity is present in a reversibly chelated form. As such, the nucleic acid is protected from digestion until the divalent cations are liberated. By chelating the divalent cations with, for example, a light-inactivated chelator such as, for example, DM-nitrophen, as described below in Section 5.3, the cations can be released within the viewing/manipulation chamber as the fluid passes through the microscope light source. Thus, the nucleic acid molecule first becomes subject to digestion as it passes through the viewing/manipulation chamber. Further, as digestion occurs, the flow maintains the order of the resulting restriction fragments, which are imaged and which, therefore, instantly produce restriction maps which have been generated in real time. An example of such a photo-inactivated chelator is described, below, in Section 5.3.

5.2. SINGLE NUCLEIC ACID MOLECULE IMAGING SIZING TECHNIQUES

Imaging

The elongated, fixed single nucleic acid molecules of the invention may be imaged via a number techniques to generate a digital image of the molecule which can be processed to obtain quantitative measurements of molecular parameters of interest. To this end, in a preferred embodiment of the present invention, the molecules being imaged are stained with fluorochromes which are absorbed by the molecules generally in proportion to their size. Accordingly, the size of the stained molecules can later be determined from measurements of the fluorescent intensity of the molecule which is illuminated with an appropriate light source; as known in the art.

The following table summarizes fluorochromes used in accordance with a preferred embodiment of the present invention for imaging purposes.

|    | Fluorochromes         | Excitation max | Emission max |
|----|-----------------------|----------------|--------------|
| A) | DNA counter stains    |                |              |
|    | (PI)                  | 330 and 520    | 620          |
|    | DAPI                  | 350            | 460          |
|    | Hoechst 33258         | 360            | 470          |
|    | Quinacrine            | 455            | 495          |
|    | Chromomycin           | 430            | 470          |
| B) | Hybridization site labels |            |              |
|    | FITC                  | 490            | 520          |
|    | TRITC                 | 554            | 573          |
|    | XTRITC                | 580            | 600          |
|    | TR                    | 596            | 620          |
|    | AMCA                  | 350            | 450          |
|    | CY5$^c$               | 646            | 663          |

In another embodiment, detection is based on fluorescent beads and on chemiluminescent tagging using alkaline phosphatase. Single fluorescent beads are easily imaged with fluorescence microscopy, including the smallest ones with a diameter of just 0.01 microns. (Although exceeding the Rayleigh limit, this bead appears as a bright spot.) Fluorescent beads provide a good way to label single DNA molecules for image processing purposes because individual beads are intensely fluorescent, morphologically distinctive, available in wide range of fluorochromes of differing spectral qualities, and are easily attached to oligonucleotides. For example, Molecular Probes, Inc., sells latex beads with coatings of carboxylate, avidin or streptavidin in 6 spectral ranges (colors) and sizes varying from 0.01 to 2 microns. The availability of carboxylate modified and streptavidin coated beads offers many alternatives for binding them to DNA molecules.

Synthesizing oligonucleotides can be covalently attached to a series of differently sized fluorescent beads (0.01–0.05 microns) to optimize RARE conditions. Smaller beads are preferable because they diffuse more readily through agarose gel but larger beads are easier to derivatize due to their larger surface area. Fluorescent beads of similar size have been imaged electrophoresing through gels by fluorescence. Forming RecA filaments using these modified oligonucleotides and assaying their formation by functionality in a RARE test system can also be used.

Providing Chemiluminescent Detection of RecA-Mediated Hybridization:

Chemiluminescent labeling of oligonucleotides for nonisotopic detection in Southern blots and other techniques is a popular labeling technique especially because of its high sensitivity, among other merits. In general, alkaline phosphatase is attached to oligonucleotides (commercially available systems), which are then hybridized to target DNA. Following formation of hybrids, a chemiluminescent substrate is added, usually 1,2 dioxetane, which rapidly decomposes into a chemiluminescence generating compound. Light is emitted with a maximum at 470 nm and a half life of 2–30 minutes depending upon the chemical environment.

Given its high sensitivity and the availability of high quality commercial kits, chemiluminescence can be used in this invention to optically detect RARE on single DNA molecules using the techniques developed for optical mapping. For example, alkaline phosphatase can be covalently linked to oligonucleotides, or DNA can be linked to biotin-streptavidin attachment schemes; with kits commercially available). The conjugated oligonucleotides will then be made into RecA filaments and tested for RARE effectiveness. An advantage of the biotin-streptavidin mediated alkaline phosphatase linkage is that excess biotinylated alkaline phosphatase can be easily dialyzed out of the system to reduce stray chemiluminescence. A chemiluminescent detection system can be used with RARE, and optical mapping using most of the steps described herein. The RecA-oligonucleotide (linked to alkaline phosphatase)-target DNA complex in molten agarose gel and then mount this for optical mapping. Instead of diffusing magnesium ions in to trigger enzymatic cleavage, dioxetane is diffused, required by the chemiluminescence system, for visualization of RARE sites. The chemiluminescence activity can then be visualized through the microscope using an ICCD camera; with no illumination necessary. To image the entire molecule, DNA-fluorochrome fluorescence can be used, and different fluorochromes used if initial compounds used quench or interfere with chemiluminescence.

Using Imaged Energy Transfer to Reduce Background from Tagged RecA Filaments

An alternative approach to molecular imaging is to use energy transfer between the fluorochrome labeled DNA and the bead-attached to the oligonucleotide. Excitation can be selected making the DNA-fluorochrome complex the donor and the bead the acceptor. This means that the bead could fluoresce only when it is within 100 angstroms or less of the donor. However, the efficiency of transfer falls off dramatically with distance. Energy transfer imaging using fluorescence microscopy with different microscope filter combinations allows visualization of the donor, acceptor, and the donor-acceptor pair; these are conveniently slid in and out of the illumination path. A good energy transfer donor to use here is ethidium bromide or the homodimer, since these fluorochromes bind tightly the fluorescence yield increases dramatically upon binding. A concern is that free fluorochrome can act as a donor, though probably not as effectively the intercalated material. If free chromophore does in fact become a problem, the filament can be split into two parts and fluorescent beads can be attached in a head-to-head head fashion so that they will serve as the acceptor-donor pair for energy transfer imaging. Another concern is that latex beads are prone to aggregation, which problem can be solved appropriate selection and use of chromophores (Molecular Probes, Inc., Portland, Ore.). Measures which can be used against aggregation include maintaining some charge on beads through careful attention to ionic strength, and use of Triton X-100 detergent or BSA.

The molten RecA-bead-DNA mixture is then stained with DAPI and spread on a microscope slide for optical mapping. Finally, length and intensity measurements are used to map the bead position. "Red" beads (Molecular Probes, Inc.), can be used to provide contrast to DAPI's blue fluorescence.

The amount of labeled RecA filament may be a concern in optically based methods: too many free fluorescent beaded filaments can obscure imaging beads present in the complex with target molecules. The following simple actions can be taken to eliminate this problem if it occurs:

Carefully titrate the amount of labeled filament and balance the minimum necessary hybridization efficiency for convenient observations against contrast quality. RecA-mediated hybridization does not require the RARE methylation and restriction enzyme cleavage steps, so that hybridization efficiencies do not have to be critically optimized for acceptable results.

Unbound filaments can be diffused out through dialysis, or mild electrophoresis in gel fixed systems could selectively sweep filaments from the viewing field and leave the much larger target-filament complexes in place. If necessary, additional RecA protein can be added for stabilization.

The discussion above is not meant to provide an exhaustive list of molecular imaging techniques. Others techniques can also be used, as known in the art, if necessary.

Sizing Techniques

Methodologies for quantitative measurements of physical parameters associated with single nucleic acid molecules are of critical importance in virtually every aspect of physical genomic analysis. Especially valuable are techniques for sizing single DNA molecules or fragments obtained from restriction digestions that can be used for construction of high resolution restriction maps. Although pulsed electrophoresis has been shown to adequately separate large DNA molecules, accurate sizing remains problematic in a variety of other settings, and independent size measurements using parallel methods are often lacking.

In accordance with one aspect of the present invention, several different methods are proposed for measuring the size of nucleic acid molecules. These methods can be broadly classified into two groups: (a) techniques in which the measured molecule remains static during the measurement period; and (b) techniques in which the size of the molecule is determined using dynamic measurements that require molecular perturbation.

Static sizing techniques in accordance with the present invention include measurements of the relative fluorescence intensity of imaged molecules and measurements of their apparent length. These methods are convenient to use because they do not require very sophisticated equipment and are well suited for high-throughput parallel measurements, as described in more detail in section 5.4. On the other hand, dynamic, or perturbation-based sizing techniques, while at present being less suited for high-throughput measurements, sometimes provide superior results in terms of information content, precision and resolution.

5.2.1 STATIC MEASUREMENT TECHNIQUES

Figure 26A:
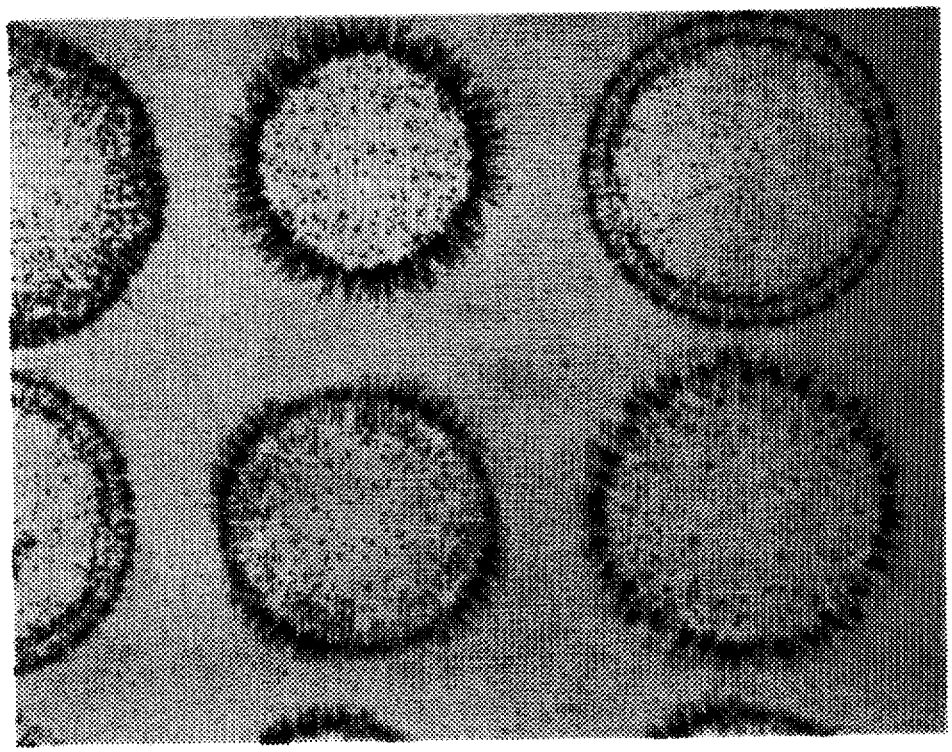
Figure 26B:
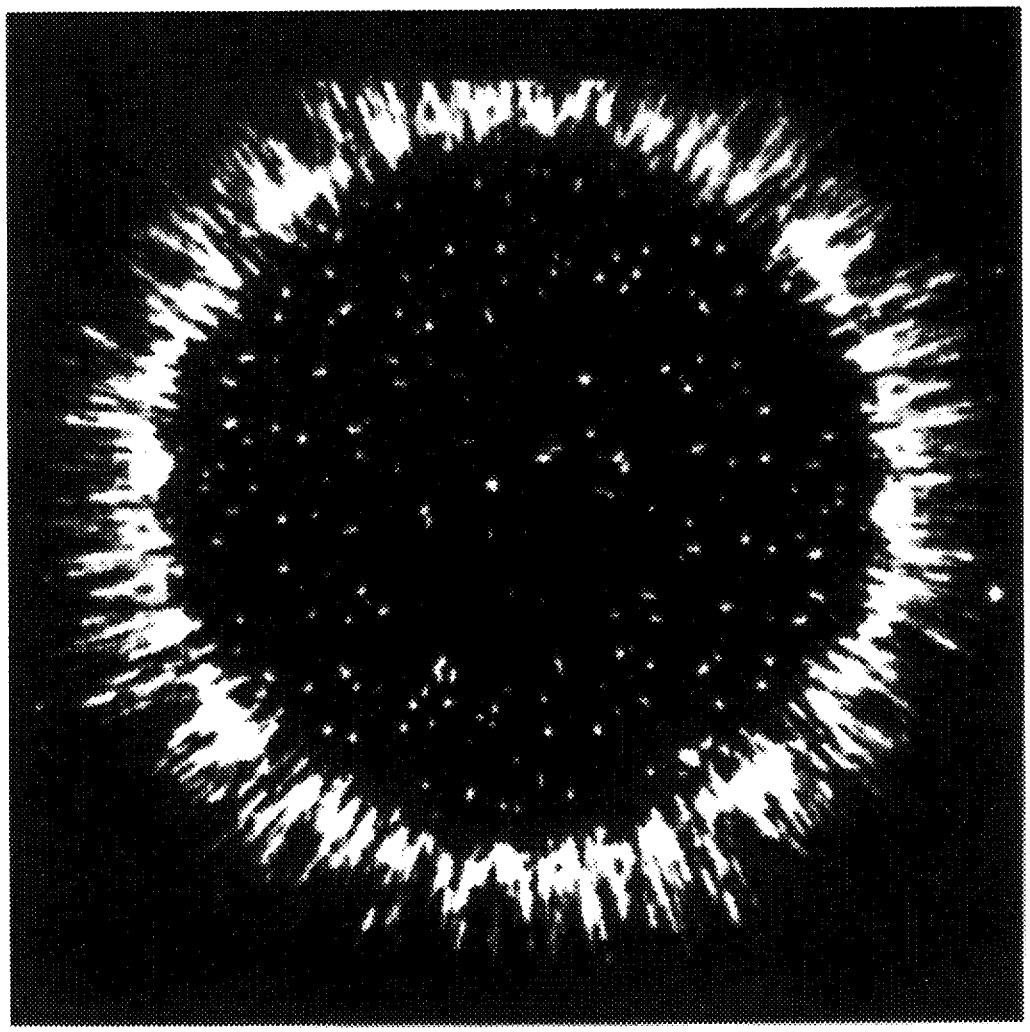
Figure 26C:
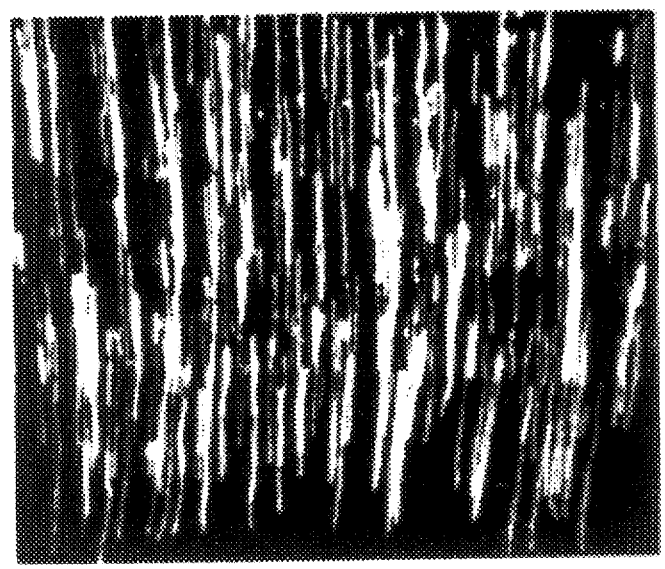

Static molecular sizing techniques are based on fixing the molecule to be measured on a plane surface, staining it with fluorescent dye, obtaining an image of the molecule and measuring parameters of the imaged molecule which have known correlation to the parameters of interest. In accordance with the present invention when used in a static measurement, molecules to be sized are first elongated and fixed on a plane surface using any of the methods described in section 5.1 above. Restriction enzymes may also be added if required to enable the digestion of the fixed molecule. In such case, magnesium ions are diffused in, triggering digestion, after which restriction sites can be visualized as growing gaps in the elongated DNA molecules. This imaging approach is simple, effective, and has excellent sensitivity, since molecules can be visualized directly. In accordance with a preferred embodiment of the present invention, the molecules are elongated and fixed using the spotting approach described in more detail in section 5.4, where small droplets of solution are deposited in a regular grid manner onto a plane derivative surface and let dry. As shown in FIGS. 26 A, B and C, after the spot dries, molecule remain elongated and fixed onto the surface in a "sunburst" pattern.

A. Sizing Single Molecules Using Fluorescence Intensity Measurements

In accordance with one embodiment of the present invention molecular sizing can be performed using measurements of the intensity of fluorescently stained molecules. This measurement approach is based on the observation that the size of a molecule is proportional to the amount of fluorescent dye it can absorb, which amount can be estimated by imaging the molecule. In a specific embodiment, the amount of fluorescent dye, and thus the size of the molecule is determined using a measurement of the absolute fluorescent intensity. In this approach, however, the illumination source has to provide a very stable and reproducible light output for the measurements to be accurate. Due to the fact that in practice absolute intensity measurements require precise calibration of the imaging equipment, and often are inaccurate, the size of the molecule is instead determined by measuring its relative intensity compared to the intensity of a standard, a molecule of known size within the image field and frequently consists of a portion of the imaged molecule.

In accordance with one aspect of the present invention, the accuracy of this sizing method can further be increased by providing a series of standards of different sizes and comparing the measured molecule to each individual standard. The size of the molecule being measured can thus be determined by combining all congruent size measurements, i.e. homologous restriction fragments within different molecules and averaging the results, which operation reduces the standard variation of the sizing error in proportion to the square root of the number of measurements taken. In order to generate the desired series of standards, in one important embodiment of the present invention restriction enzymes can be used to cleave a known molecule into a sequence of fragments with physical dimensions which can be known to within a single base pair.

In accordance with the present invention, the relative intensity sizing measurement involves obtaining of a digital image of the molecule being sized and of the standard, as defined above. High resolution, i.e. 1K×1K images with 16 bit gray level resolution are used in a preferred embodiment. If necessary, flat field correction of the digital image can be used to equalize the illumination intensity level over the image field. The method further involves: applying median filtering or a similar filtering operation to remove spot noise, if necessary; thresholding the resulting image to obtain binary images corresponding to the contours of the imaged molecules; applying a background correction to remove the pixel intensity which corresponds to the background level of illumination for the image field; and measuring the relative intensity of the molecules to be sized with respect to the intensity of the known standard. The intensity of the molecule to be sized is measured by adding the intensities of all pixels within the molecular contours obtained in the binarization step. Comparing the intensity measurement of the molecule being sized to the intensity of the standard determines the relative molecular size. Thus, if the underlying size of the standard is known, the absolute size of the molecule can be determined directly. The functional relationship between the relative image intensities and the molecular mass is linear (i.e. the relative intensity is proportional to $M^1$).

One drawback to this approach is that, depending on the fixation, the measurement errors often tend to be absolute instead of being relative. This means that, for example, a 20 kb standard deviation applies to a 60 kb fragment as well as to a 900 kb sized one. In other words, the coefficient of variation (the ratio between the mean size and the estimated standard deviation) can vary enormously and will penalize small fragments disproportionately compared to larger ones. The use of improved fluorochromes and better camera equipment, as described in section 5.4 next, can resolve this problem to a large degree.

Experimentally, the lower size limit of the relative intensity optical mapping is currently about 300 bp, which limit can further be extended to smaller fragments by using sample averaging over a series of identical measurements. As discussed below, if the initial images are of good quality and are relatively noise-free, the accuracy of the method using fluorescence microscopy of DNA fragments can be increased to a single bp.

An important advantage of relative fluorescence intensity measurements over the contour length approach discussed next is that molecules do not have to be perfectly stretched, because the method depends on the relative fluorescence intensity, which is in turn determined by the amount of absorbed dye and thus does not change much even if the fixation is not perfect. On the other hand, contour measurements rely for accuracy on optimal fixation which can be detrimental in some instances.

Finally, an important improvement of the relative fluorescence intensity measurements can be achieved if sequence-specific fluorochromes, such as DAPI, which prefer AT sequences, or ethidium bromide, which favor GC regions, are used to differentiate between similarly sized fragments of a molecule. In particular, non-specific fluorochrome measurement can be made first, as described above. Next, using DAPI to discriminate between different fragments allows size differences to be quantified to within single bp.

B. Sizing Single Molecules Using Contour Length Measurements

According to another embodiment of the present invention, a second way of measuring the size of static nucleic acid molecules is to image the molecules and measure their contour length by processing the digitized molecular images. As discussed below, the measured length can be used to obtain an adequate estimate of the size of the molecule.

As known in the art, objects in a digitized image can in many instances be characterized satisfactorily by structures composed of line and arc patterns. In accordance with the present invention, morphological image processing can be applied to obtain a quantifiable topological representation of the molecules being sized. Morphological processing in the context of this invention refers to operations where the imaged molecule is represented as a set of structural elements, and thereby can be reduced to a more revealing shape.

In a specific embodiment, the parameter of interest is the length of the imaged molecule which may not be entirely stretched. To this end, following the image correction and binarization steps discussed above, algorithms known as "thinning" can be used to reduce the imaged molecule into a set of simple digital arcs, which lie roughly along the medial axes of the molecule. (The medial axis of an object is defined as the set of points which are equidistant from the nearest boundary point of the object). The image of the molecule can be thinned using an image processing operation known as erosion, which consists of deleting from the border pixels that have more than one neighbor pixel which belongs to the object. (Jain, Fundamentals of Digital Image Processing, Prentice Hall, 1989). Once the medial axis is determined, the apparent length of an object can easily be computed and next used to derive other molecular parameters of interest by comparing it, for example, to the length of a known standard. Alternatively, if the magnification of the system is known, the length of the digital image of the molecule can be converted directly to kb measurements. The contour length measurement method approach above resembles the measurement of the length of a rope and because it is simple to implement can also easily be automated.

Contour length measurements have been found in some cases to be more accurate than the relative intensity measurements described in section A above, especially for small size molecules. The reason is that, as shown in Example 4 below, and in FIGS. 4A–4I and FIGS. 5A–5J, fluorescence microscopy can image single polymer molecules stained with an appropriate chromophore and provide a distinguishable outline of the molecule being imaged. Thus, even though the molecular diameter dimension may only be about 20 angstroms, single molecules can still be easily visualized on the basis of their apparent contour. On the other hand, the intensity of the fluorescent light from the molecule may not be sufficiently distinguishable from the background intensity, in which case the relative intensity measurement method will give inaccurate results.

As in the relative intensity size measurements, size measurements using the contour length approach vary approximately as $M^1$ and are only sensitive compared to the dynamic measurement methods discussed below, which can have $M^{1.5-3.3}$. However, molecular measurements using static approaches are particularly suitable for high throughput systems and can be used for fast sizing and ordering of DNA fragments, such as restriction digests, as described in detail in Example 10, since the measurement time is limited to imaging. No complicated molecular perturbation are necessary, such as laser tweezers, flows and complex electrical field arrangements.

In a specific implementation of both static sizing methods discussed above, image measurements can be performed using images having 16 bit gray level resolution. The original raw digital image is displayed in an enlarged format using, for example, pixel replication,.and an overlay image is prepared by manually tracking the DNA contour. The contour length map can be prepared from this overlay directly. For intensity calculations, the 13-bit raw image data is smoothed and the overlay image dilated five times to cover all foreground pixels. For each pixel marked on the overlay as being part of the molecule, a synthetic background level is calculated as the weighted average of the surrounding pixels, with weight factors decreasing with distance, and equal to zero for the marked pixels. For example, a 3×3 or a 5×5 window can be used for this purpose, with coefficients determined to add up to unity, as known in the art.

Using this method, the intensity of a particular molecule or DNA fragment can be determined by subtracting the sum of the matching background pixel intensities from the sum of all pixel intensities which belong to the fragment. This measurement can be repeated for each frame of raw image data that had an overlay image, excluding those frames with poorly focused images. To increase the accuracy of the experiment, intensity measurements are averaged over several images (e.g. images). The same measurement approach can also be used to measure the relative sizes of two different fragments. In this case, if the length (or the relative intensity) of one fragment is labeled x, and the same measurement for the other fragment is y, the relative sizes of the two fragments can simply be calculated as $$SIZE_1=x/(x+y); SIZE_2=y/(x+y);$$

Analogously, if one of the fragments (e.g. y) is later cut into sub-fragments u and v, the size of fragment u, for example, is computed as $$SIZE_u=[u/(u+v)][y/(x+y)];$$

For a series of cuts, the relative size of each segment analogously as the ratio of the segment measurement (x) over the sum of all fragment measurements.

5.2.2. DYNAMIC MEASUREMENT TECHNIQUES

Measuring fragment sizes using dynamic relaxation methods has important advantages over the static methods discussed above. The reason is that in static sizing it is sometimes critical that the molecules are optimally stretched. Overstretched or suboptimally elongated molecules cannot be measured accurately using absolute-length based static measurements because the functional relationship to the molecular mass in this case is dependent on the level of elongation. Relative length measurements, as described here are, however, immune the level stretching. In addition, a specific problem encountered using stationary sizing approaches is that due to imperfect fixation, inadequately fixed fragments are prone to premature relaxation which can complicate the sizing process. On the other hand, strong fixation of the DNA to the surface typically interferes with the observation of cut sites, which requires local relaxation to produce visible gaps. The facultative fixation technique described here, however, can deal with this problem successfully.

In contrast, dynamic measurements of DNA molecules do not always require molecules to be completely stretched out in order to obtain an accurate measurements. The measured relaxation times are typically independent of the degree of coil extension. This important feature has been shown for measuring DNA relaxation times using the visco-elastic technique (Massa, D. J., Biopolymers 12, 1071–1081 (1973)).

Additionally, parallel dynamic measurements can be made using molecular imaging techniques (e.g., fluorescence microscopy), and size distributions can be determined accurately since the conformational dynamics of each molecule is measured separately. There is another compelling reason for using dynamic relaxation methods: the associated relaxation times. ($\tau$) are strongly size dependent, with $\tau$ being proportional to the molecular weight $M^{1.5-3.3}$, so that size discrimination is much more precise and ultimately accurate compared to the static methods considered above. Naturally, the determined size dependence will vary with the chosen relaxation mode. Molecular relaxation measurement techniques in fact surpass any other sizing technique with the exception of sequencing.

A. Dynamic Molecule Sizing Using Optical Contour Maximization (OCM)

The OCM molecule sizing method of the present invention is based on the observation that when a linear DNA molecule snags an obstacle during electrophoresis in a loose gel matrix it elongates nearly completely to form a metastable hook that can persist for several seconds (46). Such loose matrix can be formed, for example, at the coverslip-agarose gel interface, as described in section 5.1.1. The gel-coverslip interface in this case consists of a loose matrix, a few microns deep, which is ideal for OCM use because it provides a convenient series of "pegs" for DNA molecules to ensnare and form hooks upon (see FIG. 9). A relatively weak electrical field (e.g., 5–30, volts/cm) is sufficient for complete elongation of a tethered or temporarily snared DNA molecule. If the hook arms are similarly sized, the molecule can be stretched out to nearly its full contour length. The longest observed hook contour length can be determined from a set of rapidly collected images.

Unlike the static contour length measurements approaches discussed above, the degree of molecular elongation using OCM is optimal. In fact, the maximal contour lengths determined in this method show a linear correlation to the reported size in the 240–680 kb interval. OCM sizing accuracy and precision is very high, as good as or better than pulsed electrophoresis based measurements. A disadvantage of this approach is, however, that in order to complete the measurements, a series of consecutive images must be taken in order to capture the optimum molecule elongation before it leaves the visual field due to the applied electrical field.

(B) Matrix-Mediated Visco-Elastic Sizing Methods

Measurements of coil relaxation times are simple to carry out. To this end, large DNA molecules, stained with ethidium bromide, are embedded in 1% agarose and mounted on a epifluorescence microscope, equipped with a SIT camera (a low light level sensitive device) and interfaced to an imaging board set contained within a computer. Electrodes in the microscope chamber are pulsed so that molecules form hooks, and their lengths are measured automatically during relaxation by a special program written in NIH image macroprogramming language available from Wayne Rasband (wayne@helix.nih.gov). The relaxation of the DNA molecules starts when the applied field is shut off. In a specific example of yeast chromosomal DNAs, single exponential relaxation times are calculated for a series of molecules and are graphed as shown in FIG. 9, as a ln—ln plot versus size. The slope of this line gives the molecular weight dependency for τ, the relaxation time (τ)=constant (size)$^{1.45}$ (kb).

In accordance with one embodiment of the present invention, fast coil relaxation times that correspond to Zimm-Rouse relations normally encountered in solution can be initially measured. In a gel matrix, a stretched out DNA molecule with length L(t) (this is actually the length of the primitive tube, will relax as <L(t)>=Aexp(–t/τ)+<Le> (74, 75), where τ is the relaxation time, t is time and the brackets represent an ensemble average. L(t) is not the molecular contour length, but can be interpreted as the apparent molecular length as imaged by the microscope. Le is the equilibrium molecular tube length and is measured as a plateau region in an exponential decay. L forms the basis of the baseline sizing methodology, as discussed below. Both experimental and theoretical studies of DNA conformation during gel electrophoresis show that a DNA molecule stretches out to form long hooks, which relax back to a compact conformation in a cyclically occurring fashion. Hook formation can be used to stretch DNA molecules out so that when the perturbing electrical field is shut off, relaxation kinetics of single molecules can be quantified by simply imaging them and measuring the length changes. This measurement is similar to stretching out a spring, releasing it and monitoring the recoil kinetics by watching it shrink back to a relaxed state.

Viscoelastic measurement techniques perturb coil conformation and measure the time needed to return to random states. The measured relaxation time is quite sensitive to molecular weight and varies as $M^{1.66}$. Within a given size distribution the largest molecules dominate the measured relaxation, so that size mixtures cannot be fully analyzed.

In one embodiment of the present invention, coil relaxation is measured in gels and in free solution for developing rapid and sensitive techniques for size determination of heterogeneous samples. In practice, fluorescence microscopy can be used to monitor coil conformational relaxation kinetics to rapidly size large, single molecules (in gels). In this respect, it has been shown that coil conformational dynamics can be measured in solution, yielding reliable average molecular dimensions that can be easily related to size.

In a different embodiment, coil relaxation using morphological analysis can be measured in agarose. Specifically, parallel experiments similar to the ones done in solution described above can be performed using agarose instead. As known, the coil relaxation size dependency in gels is superior to that in a solution: $M^{2-3}$ as predicted both by reptation theory (B. Zimm, personal communication). DNA molecules from mammalian chromosomes may be difficult to measure because their relaxation times are extraordinarily long, even in a solution. For example, if a 100 Mb sized molecule has a measured relaxation time of over 7 hours, a whole day will be needed to collect all the necessary data. Relaxation processes of large molecules are complicated as assessed by spectroscopic studies. It is estimated that the relaxation times are increased 10 to 50 fold in gels as compared to solution, in which case the experiment can last several weeks or even months.

In accordance with one embodiment of the invention, the time to return to a random conformation can be shortened using the "twitch" technique to distort the molecule only slightly. The measured relaxation time using this method has been shown to be the same as if the coil was fully distorted. Essentially, in this preferred embodiment using the twitch approach makes the total relaxation time equal to the perturbation time and thus takes much less time.

In a specific embodiment of this invention, free solution measurements can be made using relatively mild electrical field strengths (40 volts/cm) to perturb conformation. In this embodiment, molecules are suspended in solution, mounted on the microscope, electrically perturbed, and the resulting relaxations are monitored by fluorescence microscopy and digitally recorded by an image processor. Morphological analysis of these images can be used to track relaxation by automatically characterizing molecular shapes.

Image collection procedures for the visco-elastic sizing method above are virtually identical to those described in the previous sections so that the same images can be used for both length and relaxation measurements. In this approach, the morphological analysis uses image processing routines to fit ellipsoids around the image of the relaxing coil mass. In accordance with the method, the associated major and minor axes of the fitting ellipsoids are used to estimate the relaxation progress. A set of molecules can be used to benchmark and establish relaxation dependent sizing conditions. Statistical analysis can be used to determine the precision and accuracy of these measurements. The functional dependence of the molecular size to the relaxation time is approximately $M^{1.5}$.

C. Sizing Molecules Using a Baseline Measurement

In accordance with another embodiment of the present invention, single molecule sizing can be performed using what is known as "baseline" measurements. Specifically, typical DNA relaxation plots, as apparent length versus time, provide plotted points which are averages of several (usually 4–5) relaxation measurements. Such plots show that the measured length of the molecule decreases in an exponential fashion and, importantly, that the molecule does not fully relax to a spherical random conformation. Instead, the quasiequilibrium structure is a thickened, short rod-like object, which signals an end of the exponential decay, and its length is the baseline for the plot. Very slow relaxation processes are still happening, but they are of a different nature and develop in a different time scale, which could be proportional to $M^3$.

Within the time scale actually used (e.g., hundreds of seconds), length measurements settle down to an equilibrium value which is termed the "baseline". Baseline values vary linearly with DNA size and are very reproducible. In this embodiment of the present invention, a relaxation measurement yields molecular size estimates in two independent ways: 1) by determination of the relaxation time, τ, and 2) by length measurements for baseline determination. Thus, the two measurement approaches could be used simultaneously to derive different estimates of the molecular size.

More specifically, the procedures for carrying out the relaxation measurement in accordance with the baseline measurement method of the present invention are as follows:

(1) Apply an electrical field and keep the selected molecule in view by switching field orientation. When a hook is formed, turn off the electrical field immediately before one hook arm is pulled off from the apex, and then start collecting images. Proper imaging requires that the entire molecule be in focus.

(2) Collect images, every 10 or 20 seconds using 8 or 16 video frame-averaging to reduce noise. Up to about 50 images for each measurement are necessary.

(3) Repeat steps (1) and (2) for a given molecule as many times as possible for subsequent data averaging.

(4) Analyze and image process each of the 50 images. (Processing steps may include noise reduction, smoothing and skeletonization to produce suitable images for binarization, so that an automatic analysis algorithm can operate on the images. Extract length parameters and obtain the relaxation plots $L_i(t)$, where i is the image number.

(5) Add all relaxation plots of a given molecule together to perform ensemble average, i.e. determine $<L(t)>$ over all images. Determine the baseline $<L>$ from the end plateau of the relaxation curve and fit the curve using the expression $$<L(t)> = A \exp(-t/\tau) + <L>$$

to obtain an estimate of the relaxation time $\tau$.

The method steps above can be implemented in a specific embodiment of the present invention using a Zeiss Axioplan epifluorescence microscope with #15 filter cube (green excitation, red observation), and Pol Plan-Neofluar 100xz and 63×1.30 numerical aperture objectives (for larger molecules). The distance per pixel can be calibrated using a USAF-1951 resolution target, and was determined in a specific embodiment to be 0.217 μm and 0.345 μm respectively. A 6115A precision power supply (Hewlett-Packard) can be used to provide potential across the chamber electrodes. Frames from a C2400-SIT camera (Hamamatsu) can be averaged by PixelPipeline (Perceptics), digitized (480× 512×8 bits) and be stored in a Macintosh IIfx computer. Averaged images are preferably processed to remove background, reduce noise, and simulate shadowing (some images) using NIH Image (wayne@helix.nih.gov) and NCSA Image (softdev@ncsa.uiuc.edu) software for Macintosh, and photographed by a film recorder (Polaroid).

In a specific application of the baseline sizing method described above, yeast chromosomal DNA was resolved by Pulsed Oriented Electrophoresis in 1% Seakem low melting agarose (FMC), ½×TBE (42.5 mM Tris[1], 44.5 mM boric acid, 1.25 mM disodium EDTA). Excised gel bands, or alternatively a synthetic matrix, were repeatedly equilibrated in TE (10 mM tris, 1 mM EDTA, pH 8.0)(19). Bands were further equilibrated in TE containing 10 mM NaCl, melted 72° C., 10–15 min and equilibrated to 37° C. Ethidium bromide (final concentration 1 μg/mL) and 2-mercaptoethanol (final concentration 10 μL/mL) for minimizing photodamage were added to melted sample, equilibrated at 37° C. from 10 min to a few hours. To prepare the final sample, 10 μL (cutoff yellow pipette tip used) was cast onto a preheated slide with 1.8 cm.×1.8 cm. coverslip and applied to a stage electrophoresis chamber (11), electrode spacing 2 cm. The edges were sealed with mineral oil to prevent evaporation. Coverslips and slides were cleaned by boiling in 0.075M HCl for one hour, rinsed with distilled water several times, and stored in 100% ethanol before use. Mounted samples were incubated at 4° C. for at least 15 min before image collection at 37° C.

Sample preparation is prone to variations that can affect results. For example, small gel samples are melted and reformed within a thin region between a slide and a coverslip. Evaporation can also be a problem. Despite these concerns, it was found that measurements are reproducible if fluid adhering to the gel slices, containing DNA, is removed prior to melting. Uniform gelation conditions must also be stringently followed. Following the method steps above, relaxation time determinations were made more accurate by averaging of 3–8 measurements. For each curve, the $L_i$ is determined from the last 15 data points, which are then used along with the first 20 or 30 data points to extract the relaxation time $\tau$. The distribution of the measured Li is relatively narrow and the standard deviation is less than $<L>$–½.

Figure 27A:
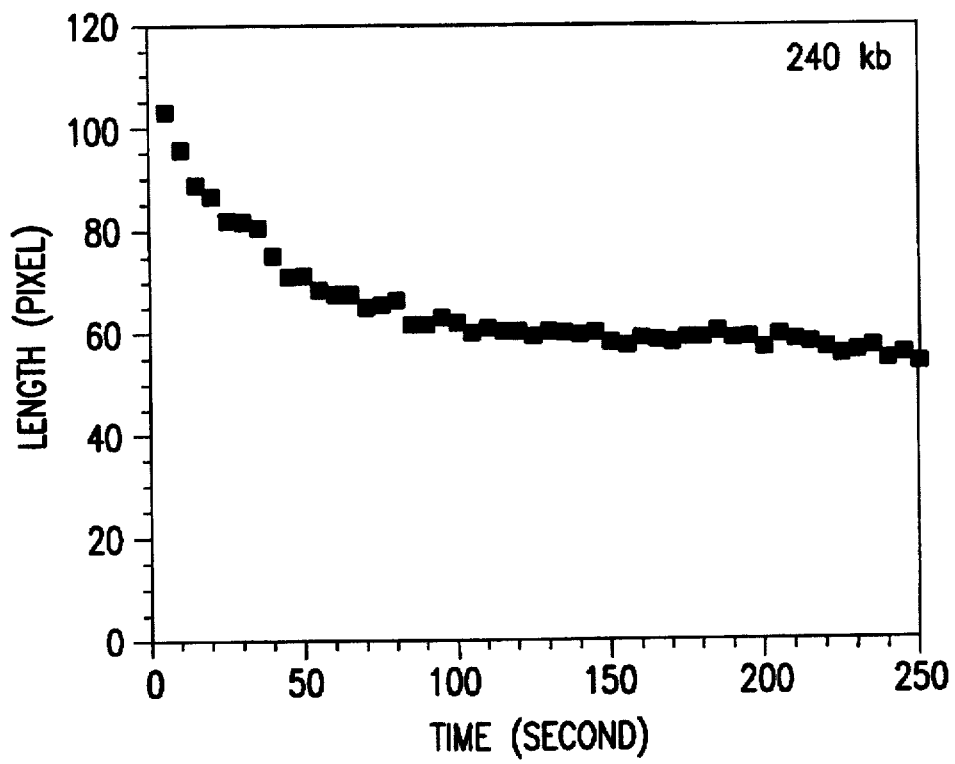
Figure 27B:
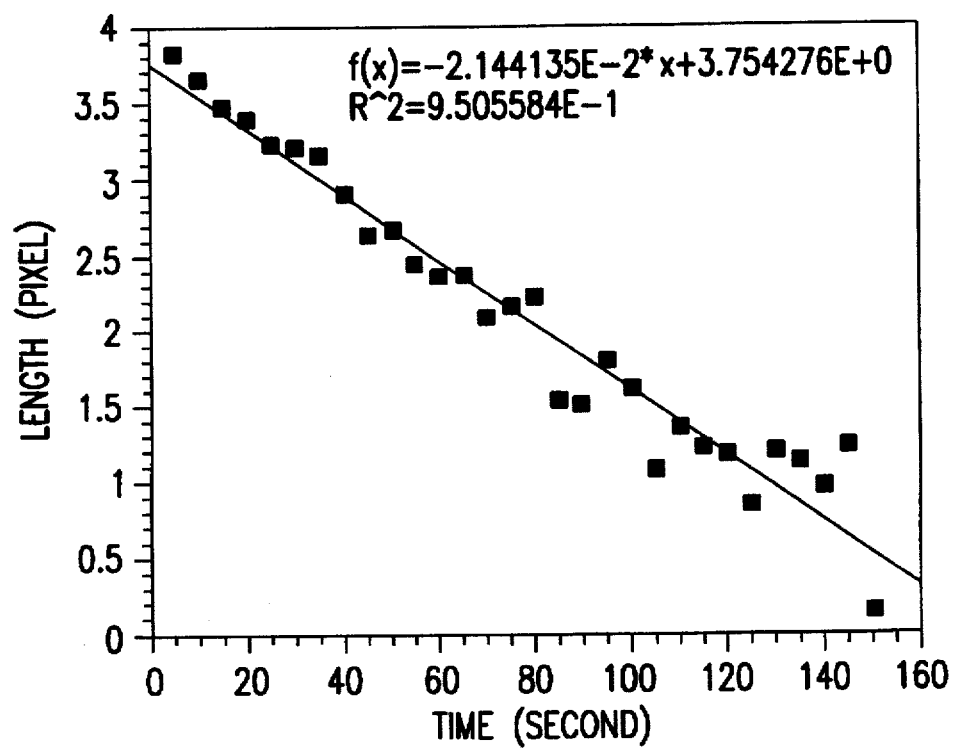

FIGS. 27 A and B show relaxation measurements as a function of molecular size (245–980 kb) and the parameters extracted from each. All curves can be seen to fit reasonably well single exponential decay. Disengagement from the tube is not significantly observed from the figures.

Figure 28A:
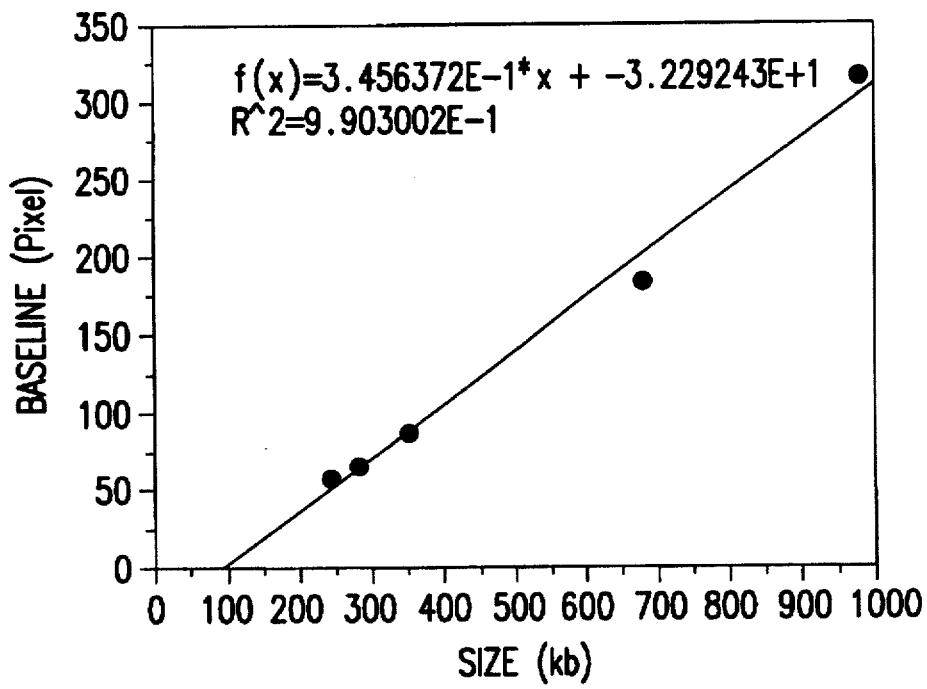
Figure 28B:
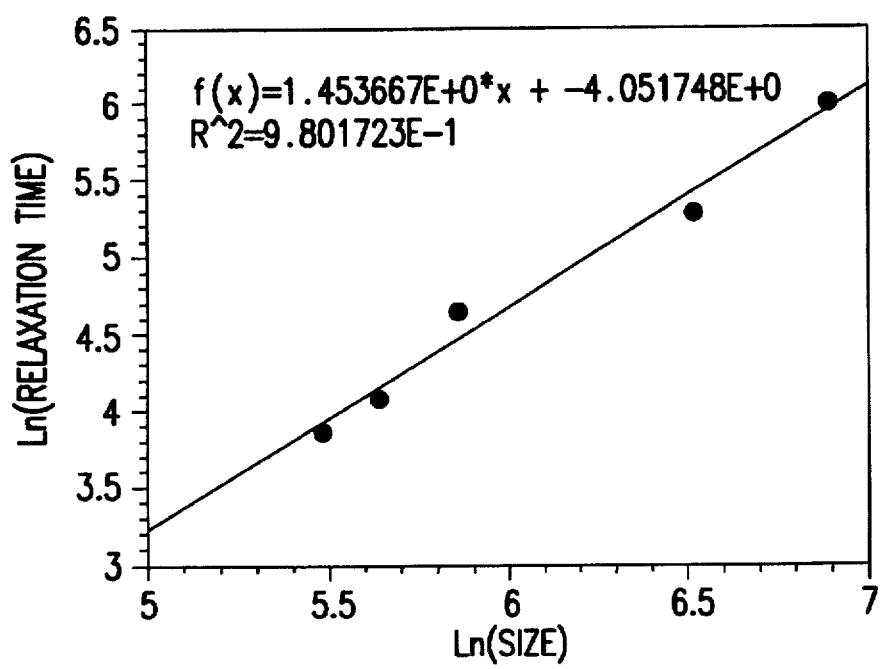

FIGS. 28 A and B are plots of relaxation vs. size respectively. By fitting the experimental measurements to the adopted mathematical models, the following two relationships were obtained:

$$<L>(\text{pixel}) = 0.345 \text{ SIZE (kb)} - 32, \text{ (1 pixel} = 0.27 \text{ μm)}$$

$$\tau(\text{second}) = 0.017 \text{ SIZE}^{1.45}(\text{kb}).$$

Notably, the relationship for $<L>$ has a negative intercept after fitting data for a wide range of molecular sizes. For small molecules the relationships are $<L> = \text{SIZE}^v$ with $v=\frac{1}{2}$. Values for v depend on molecular size and range from ½ to nearly 1 for large molecules.

F. Other Methodologies For Molecular Measurements

Other aspects of the present invention involve measurement of the reorientation time of a molecule subject to at least one external force, for example, sequential electric fields in different directions. This approach is described below in Example 6 and is illustrated in FIGS. 4A through 5J. Using the process as described below in the Examples, it has been determined that during pulsed field electrophoresis, the blob train of a DNA molecule orients with the applied electric field in a very complicated manner and during this process, electrophoretic mobility is retarded until alignment is complete, e.g., until the molecule is aligned with the applied field. Upon field direction change, the blob train moves in several new directions simultaneously (i.e., the blobs appear to be moving somewhat independently). Eventually, some part of the blob train dominates in reorienting with the applied field and pulls the rest of the blobs along its created path through the gel. The time necessary for complete blob train alignment varies directly with size; i.e., a 10 mb (1 mb=1,000 kb) molecule requires one hour to reorient, while a 10 kb molecule requires only ten seconds, using similar field strengths. The phenomenon is illustrated in FIGS. 4A–4I. Reorientation is measured in various ways, including by light microscopy and by microscopy combined with spectroscopic methods.

Another embodiment of this invention involves measurement of the rotation time of a molecule subject to sequential electric fields in different directions. Rotation of a molecules using this approach requires a series of incremental reorientation steps, each of which causes the molecule to rotate further in the same direction, until the molecule has undergone a rotation of a specified angular increment, for example, 360°. This embodiment is particularly well suited to characterize stiff, rod-like molecules, such as small DNA molecules, which do not significantly change conformation upon application of an external force. However, large molecules also may be sized by this method if the conformation of the molecules is kept relatively constant, preferably in a rod-like or elongated conformation. This is accomplished by applying a pulsing routine which is appropriate to the size, shape and perhaps also the composition of the molecule.

As a non-limiting example, molecules are rotated in the presence of sinusoidally varying electrical fields applied at 90° to each other. Stiff, rod-shaped molecules or stretched molecules are rotated about their long or short axis. Rotation about the long axis has the greatest molecular weight dependence, with rotation diffusion varying proportional to about $M^3$. Rotational motion of a rod-shaped molecule immersed in a gel or any other confining may be difficult if an attempt is made to simply rotate the molecule as a boat propeller rotates in water. When a gel is used, the matrix affects rotation of the molecule much as seaweed affects the rotation of a boat propeller. Thus, a pulsing routine is applied which also provides back and forth motion of the molecule, thereby facilitating rotation.

Generally speaking, an algorithm defining the pulsing routine can depend on variables such as the angle increment, time, electric field intensity, etc., and these may in turn be functions of different variables. Thus, numerous types of algorithms can be used in accordance with this embodiment of the present invention.

In a preferred embodiment, the pulsing routine used in the present invention is defined as follows $$\bar{E}_1(t) = E(t,\theta_i)(\hat{i}\cos\theta_i + \hat{j}\sin\theta_i)(\Delta t)$$

$$\bar{E}_2(t) = E(t,\theta_i)(\hat{i}\cos(\theta_i+\pi) + \hat{j}\sin(\theta_i+\pi))(\Delta t)$$

$$P_i = K_1 * \bar{E}_1(t), K_2 * \bar{E}_2(t), K_1 * \bar{E}_1, (t)$$

wherein $\bar{E}_{1(t)}$ and $\bar{E}_{2(t)}$ are electric field vectors multiplied by time (volt.sec/cm);

$E(t,\theta_i)$ is the electric field intensity in volt/cm;

$\hat{i}$ and $\hat{j}$ are unit vectors;

$\theta_i$ is the field angle, in radians or degrees, with $i=1-n$, where $n/\Sigma * \theta_i/i=1=2\pi$ or $360°$ for a complete rotation;

$\Delta t$ is pulse length, in seconds;

t is time in seconds;

$k_1$ and $k_2$ are the number of successive identical pulses; and

P is a pulsing routine, which may be repeated.

Using the above routine, a molecule to which appropriate pulses are applied rotates about $(\theta_{i+1}-\theta_i)$ radians or degrees when each set of pulses P are initiated. Also, the molecule is translated, moving laterally in the directions of $\bar{E}(t)$ and $-\bar{E}(t)$, thereby facilitating rotation.

In the above equation, $\Delta t$ is a constant, however, this need not always be the case. E may be a function of one or more variables. For example, E may be a function of total elapsed time and/or angle increment. Also, the sum of all the angular increments need not be 360°, and may be any number of partial or total rotations which provide measurements of sufficient accuracy. A specific set of conditions for measuring the rotation rate of molecules are set forth in Example 7.

In another embodiment of the present invention, sizing involves measuring the diameter of a relaxed molecule. Measurements of the molecular diameter are made according to the same procedure of staining molecules, placing the molecules in a medium, etc. as the curvilinear length measurements. However, it is not necessary to perturb the molecules before measurement. Instead, the molecules are measured when they are in a relaxed state, having a spherical or elongated elliptical shape. Because the volume of a sphere is proportional to $R^3$ where R is the radius of the sphere, and the volume of an ellipsoid is proportioned to $ab^2$ where a is the radius of the major axis, and b is the radius of the shorter axis, resolution for this technique varies as about $M^{0.53}$. Molecules measured by this technique do not need to be deformable. This technique can be used for all sizes of DNA molecules and is useful for sizing large DNA molecules, on a microscope slide, as well as for sizing densely packed molecules.

In accordance with the present invention, molecules can also be sized by measuring rotational diffusion in free solutions. The rod rotational diffusion coefficient is remarkably sensitive to size—approximately length³. The equations describing rotational frictional coefficients are as follows:

$$f_{rot} = 8\pi\eta L^3/3[(J-Y_{rot})],$$

where $\eta$ is viscosity, $Y_{rot}=1.57-7(1/J-0.28)^2$, and $J=\ln(2L/b)$; L and b are half of the rod long and short axes respectively. A useful value is the molecular rotary relaxation time:

$$\tau_r = f_{rot}/kT = 4\pi\eta L^3/9(J-Y_{rot})],$$

In accordance with one embodiment of the present invention rod rotational diffusion coefficients are determined using fluorescence dichroism, as measured by microscopy, of small (100–3,000 bp) single, ethidium bromide stained DNA molecules. Fluorescence dichroism tracks orientation as a function of time, providing the necessary kinetics information for coefficient determinations. Orientation analysis utilizes the equations above. An advantage of the single molecule approach over standard bulk measurements is that the data is intrinsically size deconvoluted.

The experimental setup consists of a Zeiss microscope fitted with an ethidium bromide filter pack, illuminated by an argon ion laser source, providing 488 nm polarized radiation, a Hinds photoelastic modulator and detection by a microchannel plate detector interfaced to a CCD video camera. Camera output is provided to the image processor for data storage and analysis. A Fluke, high power/speed amplifier provides +/–1500 volts at the needed frequency for alignment. Since the thin sample films used for microscopy draw little power, temperature control is relatively simple. Molecular alignment can be done tried using both AC or DC electrical fields. AC fields have the advantage of zero net translation during an experiment. If increased field strength is required, the sample cell can be reduced in size, bringing the electrodes closer together.

To measure the rotational diffusion coefficient, an electrical field is applied briefly to orient molecules and shut off, allowing brownian motion to relax the molecules. Depolarization is next tracked by gathering the total fluorescence decay output of each molecule in the field by a microchannel plate/CCD video camera. As the molecule tumbles and falls out of plane with the exciting radiation, its fluorescence intensity changes in an exponential fashion with a characteristic time given by the rotational diffusion coefficient. Since video cameras operate at a frame rate of 30/second, fluorescence intensities are recorded every 1/30 second by the image processor. The whole process is repeated several times and the results are averaged. An advantage offered by a video camera detection system is that an ensemble of individual molecules can be measured distinctly and simultaneously, resulting in parallel data collection and processing. The calculated relaxation time for a 300 bp DNA molecule is about 4 microseconds in water, too fast for our detection system. But since the rotational diffusion constant increases linearly with viscosity, substituting 98% glycerol can be used to boost the viscosity, and chilling the sample on the stage can further increase viscosity by a factor of $10^5$. If high glycerol concentration causes DNA denaturation at low temperature, sucrose can be tried. Either approach should provide a viscosity boost sufficient to bring the rate into range for video data collection.

Although rotational coefficients are usually determined in solution, it is known that DNA molecules less than 300 bp can freely rotate within an agarose matrix since their measured rotational diffusion coefficients are similar to free solution values. Embedding small DNA molecules in agarose during measurements can be used to stem any convective forces, should they be found to severely perturb measurements.

G. Statistical Methods to Increase the Measurement Accuracy

In this section we provide a brief outline of the statistical techniques used to increase the accuracy of the size measurements on the basis of obtaining a series of estimates of the desired parameters and manipulating in accordance with known statistical error analysis criteria. Conceptually, each measurement of the desired size of the molecule using any one of the methods described above can be interpreted as an estimate of the true quantity, which is free of measurement errors. There is no guarantee, however, that a specific measurement will not be grossly incorrect, in which case the estimated parameter is not useful for analysis. A well known method to reduce this probability is to take a series of measurements and use the mean value (the sum of all measurements divided by the number of measurements). On the other hand, a measurement of the sample variance gives an estimate of how accurate the measurements are, that is how close they are to a hypothetical ideal value.

Without going into much detail, it is known that for a set of independent, normally distributed measurements, the accuracy of the measurement increases with the sqrt(n), where n is the number of the sizing measurements. Thus, obtaining the average of 10 independent measurements will increase the accuracy of the size estimate by a factor of about sqrt(10)=3.16. What is known as statistical confidence intervals which determine the probability that a specific measurement deviates from the mean value can be used to estimate the consistency of the measurements. Thus, probability density functions (pdf) for the sample variations which are widely spread indicate inaccurate measurements (which can be discarded), while highly peaked pdfs indicate that the sample bin is consistent and likely to be accurate.

In accordance with the present invention, averaging a series of measurements to increase the accuracy of size measurements is used in all cases, when possible. To characterise the sample population further, after the measurements are averaged, the 90% confidence interval on the mean measurement value is calculated using the t distribution with n−1 d.f. and the sample standard deviation. (Bendat et al., Random Data: Analysis and Measurement Procedures, John Wiley, 1986). This calculation assumes that the measurement data represents random samples from a normal distribution and means that there is a 90% chance that the population mean falls within the confidence interval. The midpoint of this interval can be used to estimate the population standard deviation. The coefficient of variation (CV) is the estimated population standard deviation divided by the sample mean. The pooled standard deviation is the sqrt(the average of the variances). The relative error is the difference between the measurement value and the reported value divided by the reported value. These, and other relevant statistical measurements are of critical importance in increasing the accuracy of the measurement approach used, and in comparing the results to that of other sizing techniques.

5.3. GENOME ANALYSIS/MANIPULATION

Described herein are methods whereby the single elongated molecules of the invention may be utilized for the rapid generation of high resolution genome analysis information. Such methods include, as described below, both optical mapping and optical sequencing techniques.

5.3.1. OPTICAL MAPPING

The optical mapping techniques of the invention allow direct, ordered mapping of restriction sites, for the rapid generation of high resolution restriction maps. Briefly, such mapping techniques involve the elongation and fixation of single nucleic acid molecules, digestion of the molecules with one or more restriction enzymes and the visualization and measuring of the resulting restriction fragments. Because the single nucleic acid molecules which are being digested are fixed, the resulting restriction fragments remain in register, such that their order is immediately apparent and a rapid restriction map is instantly generated.

The optical mapping techniques described herein have a variety of important applications, which include, for example the efficient generation of genomic physical maps, which, until the present invention, have proven to be time consuming, costly, difficult and error prone. In fact, the approaches described herein make possible the creation of ordered, complex high resolution restriction maps of, for example, eukaryotic, including human chromosomes without a need for analytical electrophoresis, cloned libraries, probes, or PCR primers.

Further, such techniques have wide ranging diagnostic applications. For example, nucleic acid from individuals may be tested for polymorphisms which may be associated with certain disease alleles. For example, such polymorphisms may represent restriction fragment length polymorphisms, rearrangements, insertions, deletions and/or VNTR (variable number tails repeats).

Nucleic acid molecules of from about 500 bp to well over 1000 kb can efficiently be mapped by utilizing the techniques described herein. The single nucleic acid molecule-based techniques can easily be utilized in high throughput applications such as are described, below, in Section 5.4.

For optical mapping, single nucleic acid molecules are elongated and fixed according to the techniques described in Section 5.1, above. While either agarose or solid surface-based elongation/fixation methods may be utilized, solid surface techniques are, generally, preferred. As discussed in Section 5.1, the elongation/fixation techniques should be optimized to yield a balance between elongation capability, relaxation capability and retention of biological function. By appropriate elognation and fixation, the single nucleic acid molecules relax somewhat, with the fragments, therefore, moving apart upon cutting.

Cleavage sites are, therefore, visualized as growing gaps in imaged molecules. The molecules are restrained, however, from fully relaxing to a random coil conformation, which would make accurate fragment measurement impossible. In addition to gaps, cleavage is also signaled by the appearance of bright condensed pools or "balls" of DNA on the fragment ends at the cut site. These balls form shortly after cleavage and result from coil relaxation which is favored at ends (see FIGS. 13A–13F and 15A–15C). Cleavage is scored more reliably by both the appearance of growing gaps and enlarging bright pools of segments at the cut site. Otherwise, it is possible that what appears to be a gap may, in fact, be a single molecule, part of which is out of the plane of focus.

Optical mapping restriction digests may be performed by utilizing standard reaction mixtures and conditions (e.g., incubation times and temperatures). Because the technique relies on the fixed nature of the nucleic acid molecules being digested, however, it is critical that the elongation/fixation process be completed prior to the initiation of restriction digestion. There exist a number of methods by which the start of restriction digestion can be controlled, a number of which involve keeping the restriction enzyme apart from whatever cofactor (e.g., $Mg^{2+}$) is necessary for that particular enzyme's activity until the initiatin of digestion is desired.

For example, when using agarose-based elongation/fixation techniques, the nucleic acid may be mixed into molten (preferably low melting) agarose along with restriction enzyme and appropriate buffer, but without cofactor. When the reaction is to begin, the cofactor can be added, thus activating the restriction enzyme. Alternatively, the cofactor can be mixed into the agarose in the absence of restriction enzyme. In order to begin digestion, the enzyme can be added and allowed to diffuse into the gel.

When solid surface-based elongation/fixation techniques are used, restriction digestion reaction mixture, in the absence of either restriction enzyme or cofactor, can be put into contact with the solid surface. At the appropriate time, the missing component (i.e., either the restriction enzyme or the cofactor) can be added to the surface. Alternatively, a complete reaction mixture can be introduced onto the solid surface, with digestion beginning once the mixture comes into contact with the elongated/fixed nucleic acid molecules. Additionally, a necessary divalent cation can be introduced in a chelated fashion wherein the chelation is a photo-labile chelation, such as, for example, DM-nitrophen. When the digestion is to begin, the chelator is inactivated by light, releasing the divalent cation which begins the digestion.

It should be noted that not each of the restriction sites present on a given nucleic acid molecule will be cut simultaneously, meaning that not all gaps will appear at the same time. This is expected, given the variable rate of enzymatic cleavage exhibited by restriction enzymes (64). Rather, cuts usually appear within a short time, for example, 5 minutes, of each other.

The molecules being restricted and analyzed via such techniques may be visualized via techniques including those described, above, in Section 5.2.

The resulting fragments can be sized according to techniques such as those described in Section 5.2. Such techniques can include, for example, a measure of relative fluorescence intensities of the products and by measuring the fragments' relative apparent molecular lengths. Averaging a small number of molecules rather than utilizing only one improves accuracy and permits rejection of unwanted molecules or fragments. Maps are then constructed by simply recording the order of the sized fragments.

The mapping techniques described thus far function in the efficient generation of single nucleic acid molecule restriction maps. A knowledge of the orientation of these individual molecules, however, would be very useful for the alignment of greater than one such restriction map into a large, ordered map. A variety of techniques may be utilized to distinguish or diferentially identify one end of a molecule, thereby marking its orientation or polarity.

For example, mapping vectors may be produced and used in conjunction with the mapping techniques described herein. Such vectors can serve to introduce a "tag" to one end of a molecule being analyzed. Such a tag can comprise, for example, a rare restriction enzyme cutting site, a protein binding site (which, for example, can be tagged by a labeled version of the protein) or a region of DNA tending to kink (and which would, therefore, serve as a visual tag requiring no further manipulation), just to name a few. Further, such vectors may include a nucleotide sequence to which a labeled nucleotide probe may hybridize via, for example, techniques such as those described, below, in Section 5.3.2.

Size standards may additionally facillitate the accurate measurement of the restriction fragments which are generated herein. Such standards may, for example, be engineered into mapping vectors such as those described above. Methods, such as the methylation of the mapping vector, can be utilized to ensure that the siing standards remain intact during restriction. Alternatively, sizing standards may comprise fluorescent beads of different sizes which exhibit a known level of fluorescence.

The successful use of the optical mapping teshiques of the invention is demonstrated in FIG. 12, which illustrates three types of ordered restriction maps produced by optical mapping of the present invention. These maps are compared with published restriction maps. Additionally, FIGS. 13A–F, shows selected corresponding processed fluorescence micrographs of different yeast chromosomal DNA molecules digested with the restriction enzyme Not I. These images clearly show progressive digestion by the appearance of growing gaps in the fixed molecules. From such data, the order of fragments can be determined by, for example, inspection of time-lapse images obtained every time interval, e.g., 0.07–200s, or any range or value therein, e.g., 1–30s. Agreement is expected to be, and has been found to be excellent, between the optical (length or intensity) and the electrophoresis-based maps. The third type of restriction map (e.g., Com. FIG. 12) combines length- and intensity-derived data; small restriction fragments (100–20, or any range or value therein, e.g.<60 kb) can be sized by length, whereas intensity measurements can provide the remaining fragment sizes needed to complete the maps.

5.3.2. OPTICAL SEQUENCING

The elongated, fixed single nucleic acid molecules of the invention can be utilized as part of methods designed to identify specific, known nucleotide sequences present on the fixed nucleic acid molecules. Such methods are referred to herein as "optical sequencing" methods. In part because these methods involve the analysis of naked nucleic acid molecules (e.g., ones which are not in a chromatin state), optical sequencing is capable of providing a level of resolution not possible with chromatin-based detection schemes such as in situ hybridization. Optical sequencing methods, in general, comprise the specific hybridization of single stranded nucleic acid molecules to at least one nucleotide sequence present within the single elongated fix nucleic acid molecules of the invention in a manner whereby the position of the hybridized nucleic acid molecule can be imaged and, therefore, identified. Imaging can be performed using, for example, techniques such as those described, above, in Section 5.2. The position of the imaged hybridization product can be identified using, for example, the sizing techniques described, above, in Section 5.2.

As discussed above, the optical sequencing technique comprises the hybridization of nucleic acid molecules to the elongated, fixed single nucleic acid molecules of the invention such specific hybridization products are formed, in a manner which can be imaged, between at least a portion of the elongated, fixed single nucleic acid molecules and the hybridizing nucleic acid molecules. Because the hybridization is based on sequence complementarity between the hybridizing nucleic acid molecule and at least a portion of the elongated single nucleic acid, imaging of the hybridization product, coupled with the precise sizing techniques described in Section 5.2, above, optical sequencing rapidly identifies a nucleic acid region according to its specific nucleotide sequence.

The optical sequencing techniques described herein have a variety of important applications. First, such techniques can be used to generate complex physical maps, by, for example, facillitating the alignment of nucleic acid molecules with overlapping nucleotide sequences.

Second, such techniques make it possible to rapidly identify and locate specific genes of interest. For example, in instances where at least a portion of the nucleotide sequence of a gene is known, optical sequencing techniques can rapidly locate the specific genomic position of the gene, and further, can rapidly identify cDNA molecules which contain sequences complementary to the nucleotide sequence. Further, such optical sequencing methods have numerous diagnostic applications, such as, for example, the rapid identification of nucleic acid molecules containing specific alleles, such as genetic disease-causing alleles. For example, single elongated, fixed nucleic acid molecules from one or more individuals can be hybridized with a single stranded nucleic acid molecule probe which is specific for (i.e., will specifically hybridize to) an allele of interest. Such an allele may, for example, be a disease-causing allele. A positive hybridization signal would indicate that the individual from whom the nucleic acid sample was taken contains the allele of interest.

Alternatively, the single elongated fixed nucleic acid molecules may represent nucleic acid molecules which are specific for (i.e., will specifically hybridize to) an allele of interest. In such an instance, a nucleic acid sample can be obtained from an individual and hybridized to the elongated fixed nucleic acid molecules. The presence of specific hybridization products would indicate that the individual from whom the nucleic acid sample was obtained carries the allele of interest. In order for the nucleic acid sample:single molecule hybridization products to be imaged, the sample nucleic acid may be labelled via standard methods, e.g., by PCR amplification in the presence of at least one labelled nucleotide. Alternatively, as described below, the hybridization product need not be labeled, but can be identified by the imaging of a site-specific restriction cleavage event within the hybridization product. Further, as described, below, the hybridization product can be indentified via indirect labeling, via hybridization product-specific binding of a labeled compound to the produc.

Conditions under which the introduced nucleic acid molecules are hybridized to the elongated fixed single nucleic acid molecules of the invention must be stringent enough to yield only specific hybridization products. "Specific", as used in this context, refers to nucleotide sequence specificity, and a "specific hybridization product" refers to a stable nucleic acid complex which as formed between at least a portion of the elongated nucleic acid molecule and at least a portion of the introduced nucleic acid molecule which is complentary to the elongated nucleic acid molecule. The sequence complentarity between these two hybridizing portions of the nucleic acid molecules is at least about 80%, with at least 90% being preferred, and at least about 98–100% being most preferred.

Hybridization conditions which can successfully yield the specific hybridization products described above are well known to those of skill in the art. First, apart from RecA-mediated methods (see below), the fixed, elongated nucleic acid molecules must be denatured (made single stranded) such that hybridization to the introduced single stranded nucleic acid molecule is possible, by following standard denaturation protocols which are well known to those of skill in the art.

The specific hybridization products formed must be imaged in order to, first, identify that such products have formed, and, in some cases, to identify the postion along the elongated fixed nucleic acid molecule at which such hybridization products have formed. A variety of methods may be utilized for the imaging of the specific hybridization products formed during the optical sequencing techniques described herein.

First, the nucleic acid molecules which are hybridized to the elongated, fixed single nucleic acid molecules of the invention can be labeled in a manner whereby the hybridization products they contribute to can be imaged. Any of a number of standard labeling techniques which are well known to those of skill in the art may be utilized. These include, but not limited to, colorimetric, fluorescent, radioactive, biotin/streptavidin and chemiluminescent labeling techniques, with fluorescent labeling being preferred. In instances wherein the elongated, fixed nucleic acid molecules are colorimetrically or fluorescently stained, the labeled nucleic which hybridizes to the elongated molecule should be labeled in a manner which produces a different color or fluorescence than the stained elongated molecule. The labeled nucleic acid will generally be at leasat about 20 nucleotides in length, with about 100 to about 150 nuelcotides being preferred. Specific hybridization products can be imaged by imaging the labeled nucleic acid within the hybridization product.

Second, methods may be utilized which obviate the need to label the nucleic acid which hybridizes to the elongated, fixed single nucleic acid molecules of the invention. For example, optical sequencing methods may be used in conjunction with a technique known as the RecA-assisted restriction endonuclease (RARE) technique (Koob, M. et al., 1990, Science 250:271; Ferrin, L. J. et al., 1991, Science 254:1494; Koob, M. et al., 1992, Nucleic Acids Res. 20:5831). Briefly, the RARE technique involves the generation of restriction endonuclease cleavage events that occur solely within the specific hybridization product. By combining sequence-specific RARE methods with the ability to visualize the formation of restriction cleavage sites, as described for optical mapping, above, in Section 5.3.1, specific hybridization products can be detected without prior labeling of the nucleic acid being hybridizaed to the elongated, fixed single nucleic acid molecules of the invention.

The RARE technique, more specifically, makes hybridization product-specific restriction possible by selectively blocking methylase, such as EcoRI methylase, enzymes from acting upon the specific hybridization products. Methylases are enzymes which methylate nucleic acid molecules in a sequence specific manner, and nucleic acid which has been methylated is no longer subject to restriction endonuclease action. For example, EcoRI methylase methylates nucleic acid molecules at the EcoRI recognition site such that EcoRI will no longer cut at that site. Once each of the restriction sites outside the site of specific hybridization are methylated, restriction digestion is performed. The only resulting cleavage sites are those within the region where specific hybridization had occurred, thereby identifying the position of such hybridization.

RARE uses RecA protein to block methylase activity in a site specific manner. The RecA protein exhibits an ability to pair a nucleic acid molecule to its complementary, homologous sequence within duplex DNA such that a triple stranded nucleic acid/RecA complex is formed. Such a complex is protected from methylase activity. Thus, the introduction of a nucleic acid molecule which will hybridize to at least a portion of the elongated, fixed single nucleic acid molecules of the invention, together with a RecA protein (and necessary RecA cofactor reagents) under conditions, such as those described, above, which will yield specific hybridization products, generates a triple stranded complex at the site of such specific hybridization. After formation of such a triple helix complex, the nucleic acid molecule is methylated. After methylation, enzymes and introduced nucleic acid molecules are removed, leaving duplex DNA which has been methylated at all positions except those within the site of hybridization.

The triple stranded complex formation and and subsequent methylation steps can be performed either before or after the elongation/fixation of the single nucleic acid molecules. In instances wherein these steps are performed prior to elongation, care must be taken with large nucleic acid molecules to avoid shearing of the molecules. One method which can successfully avoid such shearing is to perform the steps in agarose gel blocks or "chops". "Chops" refer to agarose gel blocks containing nucleic acid molecules, in which the gel blocks have been cut into small pieces. When triple strand formation is performed in a gel composition, it is generally more efficient to combine the components in molten agarose rather than diffusion into a hardened gel.

After removal of excess non-hybridized nucleic acid molecules and reagents, the nucleic acid molecules can be elongated and fixed according to the gel-based or solid-surfaced based techniques described, above, in Section 5.1.

Elongated fixed single nucleic acid molecules which have been treated as above (either before or after elongation) are then subjected to restriction digestion with a restriction enzyme that cannot act upon (i.e., cannot cleave) the methylated DNA. Restriction digestion and cleavage site visualization can be performed according to the methods described for optical mapping described above in Section 5.3.1. The only cleavage sites which form are those within the site of specific hybridization. In cases where the exact position of such hybridization lies, sizing techniques such as those described, above, in Section 5.2, may be utilized to ascertain position. Such sizing techniques are not necessary in cases where the mere occurence of hybridization, rather than position, of hybridization is being assayed.

Additionally, methods can be utilized which obviate both a need to image a cleavage site and the need to denature the elongated nucleic acid prior to hybridization. These techniques, especially in light of the fact that denaturation is not necessary, allow for more extensive coupling of the optical sequencing techniques of this Section with the optical mapping methods of Section 5.3.1, above.

In one embodiment of such an optical sequencing technique, a modified RARE method is utilized. Such a modified RARE technique involves, as described above, the generation of a triple stranded nucleic acid/RecA complex. Because no subsequent restriction will take place, no methylation is necessary after the generation of the complex. In this version of the method, complex generation should take place after the elongation/fixation of the single nucleic acid molecule of interest. The nucleic acid molecule which hybridizes to the elongated fixed single nucleic acid molecule is labeled, as, for example, described, above, in this Section. Because RecA is being used to promote triple stranded complex formation, no prior denaturation of the elongated duplex DNA is necessary. Upon triple strand complex formation, the site of the specific hybridization is identified by imaging the labeled nucleic acid molecule with the complex.

Further, techniques may be utilized which obviate both the need for the introduction of a labeled nucleic acid and the need to image a restriction cleavage site. Such techniques involve the binding of a labeled component to a site containing a specific nucleotide sequence, such as the site of a specific hybridization product such that this site is, in effect, indirectly labeled. The bound component is imaged, thereby identifying, first, that hybridization has taken place, and second, making possible the identification of the position of such hybridizaton. Techniques such as this may be especially useful, for example, in diagnostic instances wherein the nucleic acid which is introduced to hybridize to the elongated single nucleic acid molecules is scarce. Further, these techniques make unecessary a need for amplification of such scarce material prior to hybridization, thus avoiding potential amplification-generated artifacts.

In one embodiment of such a technique, a modified RARE procedure is followed. Specifically, a triple stranded/RecA protein complex is formed, as decribed above, however, in this case, the RecA which is utilized is labeled. Once again, because no restriction will take place, no methylation step is necessary. The RecA protein must be labeled in a manner which retains its activity while allowing for its imaging. Such techniques are well known to those of skill in the art, and may include, for example, addition of epitope tags, biotin, streptavidin, and the like. In instances wherein the elongated nucleic acid molecule is stained, it is important that the color or fluorescence generated by the labeled RecA protein is distinguishable from that of the stained nucleic acid molecule. Instead, therefore, of generating and imaging a restriction cleavage site, or the imaging of a labeled nucleic acid molecule, the site of specific hybridization is identified by merely imaging the bound RecA protein.

In another embodiment of such a technique, the labeled component is a labeled compound, such as a protein, which binds nucleic acid in a nucleotide sequence-specific manner. By contacting the labeled protein to the elongated fixed single nucleic acid molecules of the invention, the presence and positon of such a binding protein could be identified.

5.3.3 DIRECTED OPTICAL MAPPING

The optical mapping and optical sequencing techniques described herein may be combined such that mapping may be performed in a directed fashion. Such technique is referred to herein as "directed optical mapping". Such techniques function to target specific portions of a genome for further high resolution mapping analysis. Specifically, single nucleic acid molecules which contain specific sequences of interest may be identified from among the total single nucleic acids present in a population of single nucleic acid molecules. Once the specific nucleic acid molecules containing the sequences of interest are singled out, such nucleic acid molecules may be further analyzed.

Such directed optical sequencing can serve a number of important applications, which include, but are not limited to diagnostic applications which can directly image, for specific loci, any genetic lesion which can be imaged via optical mapping. Additionally, fingerprints of specific genetic loci can rapidly be obtained for individuals or populations.

A number of methods may be utilized to select the single nucleic acid molecules to be further analyzed. First, each of the nucleic acid molecules which may contain the specific sequences of interest can be elongated and fixed, utilizing techniques such as those described, above, in Section 5.2. Once elongated, the single nucleic acid molecules to be further analyzed can be identified by using the optical sequencing techniques described in this Section. Finally, those single nucleic acid molecules which hybridize via optical sequencing, can be mapped at high resolution via, for example, the optical mapping techniques described in this Section.

Alternatively, nucleic acid molecules which will hybridize to the sequences of interest can be elongated and fixed on the solid surfaces of the invention. Once mounted onto a surface, all nucleic acid molecules which may contain the sequences of interest are contacted with and hybridized to the nucleic acid molecules fixed on the surface. Those single nucleic acid molecules which contain sequences complentary to those fixed on the surface will become bound to the surface. Once bound to the complementary nucleic acid molecules, the entire single nucleic acid molecule which contains such hybridizing sequences will become fixed onto the surface. Thus, the nucleic acid molecules which are to be further analyzed are not only identified, but are additionally elongated and fixed in a manner which makes them amenable to the optical mapping techniques described, above, in this Section.

5.4. HIGH THROUGHPUT OPTICAL MAPPING AND SEQUENCING SYSTEMS AND METHODS

The high throughput automated system and method of the present invention are based on optical mapping and sequencing, approaches described above, which are capable of providing high speed, high resolution mapping and sequencing of PCR products, clones and YACs and require little or no input from human operators.

Reliable, high speed molecular sizing is at the heart of any high throughput molecular analysis method. As defined in Section 5.2, there are two main sizing approaches, dependent on whether or not the molecule being sized is stationary or not. High throughput methods can be classified accordingly. Static sizing generally involves simple equipment and is thus more suitable to high throughput measurements at present. Dynamic sizing, on the other hand, is more accurate but at present is less adapted to high throughput measurements because of the more sophisticated equipment it requires.

In accordance with the present invention, high throughput molecular analysis is performed using image processing of digitized images of stationary or dynamically perturbed molecules. Both approaches are considered next.

5.4.1. STATIC MEASUREMENTS

A. Fixation and Spotting

In accordance with the present invention a novel system was developed for automated, high speed molecular fixation using surface-based methods for fixation. As discussed above, desirable DNA fixation attributes include: a high degree of molecular extension, preservation of biochemical activity and reproducibility at high deposition rates. Furthermore, the development of high-throughput systems for genomic analysis requires that the fixation approach provides high sample deposition rates, high gridded sample densities and simplified access to the arrayed samples. Inadequate attention to any of these fixation aspects is likely to unduly complicate the sample analysis and increase its cost.

Accordingly, the fixation equipment of the system of the present invention includes an automated Eppendorf Micro-Manipulator, Model 5171, and Injector, capable of depositing a large number of clone DNA molecules on a derivatized glass surface while maintaining molecular extension and biochemical accessibility. To this end, a small capillary tube (about 100 microns), or a blunt-ended glass rod are used to draw DNA samples and transfer them to the surface by simple contact as small droplets of DNA solution. The solution droplets can be mixed with a variety of dopants to produce different types of elongation conditions, as described above in Section 5.1.

The droplets are spotted on the surface in ordered arrays with spacing and deposition conditions controlled by an electronic Ludl Mac 2000 interface box connected to a computer. Spot diameters can range between 40–1000 microns which dimension is controlled, for example, by the inner diameter of the capillary tube. Preferably, smaller-size, high grid density spots are used for Optimal throughput. In addition, as clearly illustrated in FIGS. 26A, 26B and 26C, smaller size spots seem to increase the efficiency of the fixation technique, because of the relatively large number of molecules which are stretched on the periphery of the spot after it dries. In a specific embodiment of the present invention, illustrated in these figures, each spot is about 100 microns in diameter, the variation between spots being about +/−20 microns. The center-to-center spacing between adjacent spots is on the order of 150 microns, but smaller or larger spacings may also be used, if desired. The deposition of spots is controlled by computer program settings of the Micro-Manipulator and a x-y table connected to microstepped motors. Typical deposition rate for this equipment is one spot in less than about every 2 seconds.

In a preferred embodiment of the present invention a very large number of clones can be deposited on a derivatized surface using a Beckman Biomek 2000 robot programmed for sample spotting, which completely obviates the need for human intervention and is capable of achieving approximately 10 times faster deposition rates. Furthermore, the robot-aided fixation approach can result in a reliable deposition of very closely spaced DNA samples (20 microns with spot-to-spot spacing of about 35 microns).

In another preferred embodiment of the present invention, a vision controlled pick-and-place robot, manufactured for example by Research Genetics or Sci-Tech (Switzerland) can be used to completely automate the spotting process by selecting objects randomly distributed on a plane surface and spotting them in a controlled manner on the derivatized surface.

As discussed above, although small drops of DNA solution can easily be deposited onto derivatized surfaces, these molecules (below 40 kb) in solution are not elongated and thus cannot be optically mapped. In accordance with the present invention, any one of three different approaches may be used to spread and fix the spotted DNA. In one embodiment of the invention, spotted DNA molecules can be "sandwiched" with a coverslip between two glass surfaces which, when pressed together, stretch the DNA molecules positioned in between. This approach gives acceptable mapping results, however, it is serial in nature so that only one sample can be measured at a time and is thus not effective for high-throughput processing.

Figure 29:
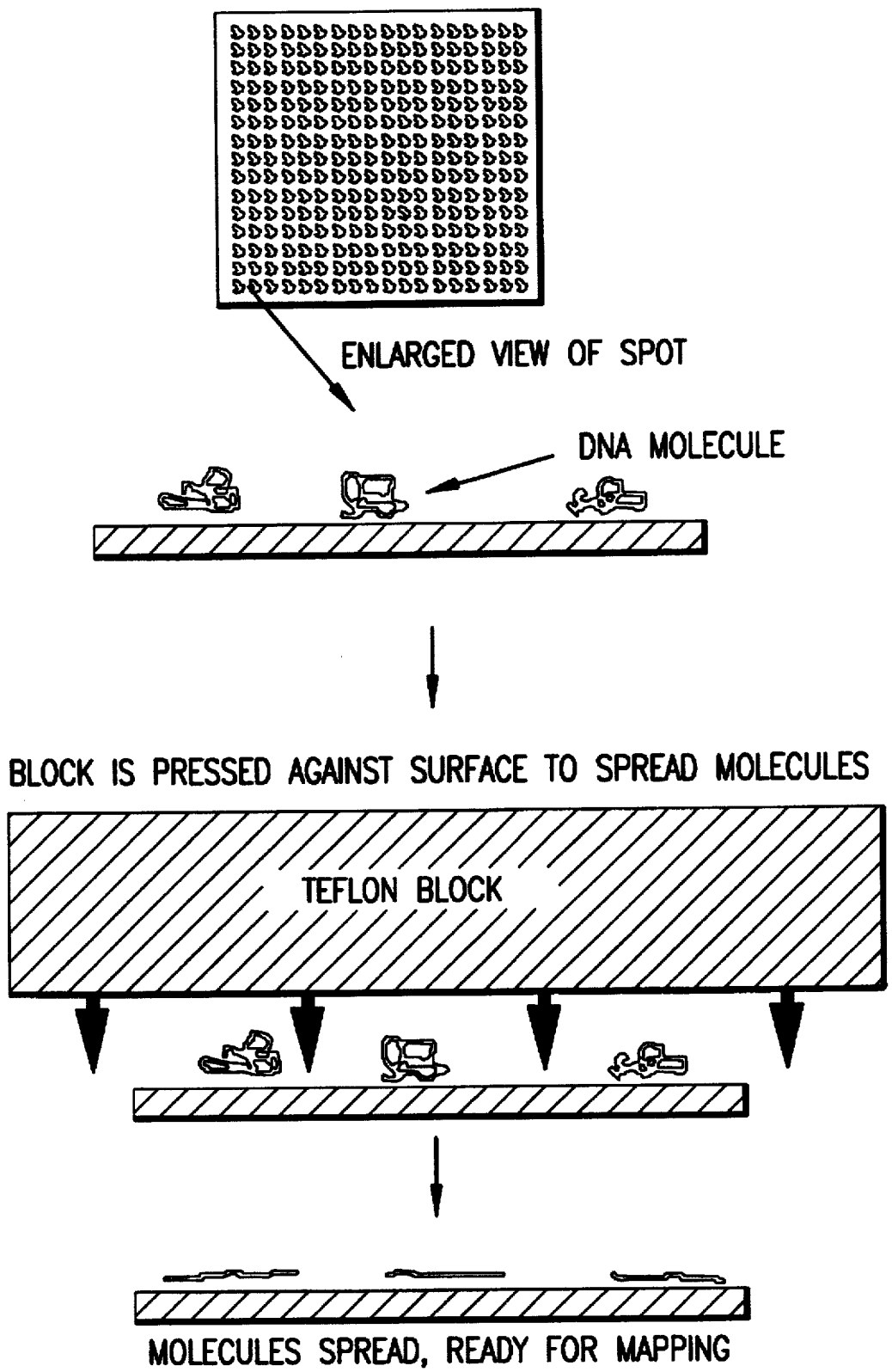
FIG. 29 shows a enlarged view of a DNA spot and one method of spreading molecules onto a derivatized surface.

In a second embodiment of the present invention, the spotted glass surface is rehydrated, after which a teflon block stamp is pressed onto the DNA spots, causing them to spread and fix on the sticky, derivatized surface. Experimental results indicate that this approach is effective for elongating surface mounted DNA without significant breakage. FIG. 29 shows an enlarged view of a DNA spot and the use of a teflon block in accordance with this embodiment of the present invention to spread the molecules onto the derivatized surface.

In a third, preferred method of the present invention, the deposited droplets of DNA solution are simply let dry on the derivatized surface. Experiments show that as the droplets dry, most of the fixed DNA remains fully elongated, aligned, and primarily deposited within the spot peripheries in a characteristic "sunburst" pattern, clearly observable in FIGS. 26 A, B and C. Addition of glycerol to the spotting solution results in well elongated DNA molecules which are more uniformly distributed. As discussed above, the rehydration of spotted DNA samples with restriction endonuclease buffer effectively restores the biochemical activity of the spotted molecules. The sunburst fixation pattern of elongated molecules in accordance with the present invention is a completely unexpected discovery which provides the basis for novel high throughput analysis methods, and has implications which are impossible to predict at this time.

In a next image preprocessing step, surface-fixed molecules are digested by adding 20–40 μl of 1× commercial restriction buffer (manufacturer recommended) containing 10–20 units of the corresponding restriction endonuclease per spotted coverslip; surfaces are then incubated in a humidified chamber for 5–20 minutes; after digestion, the overlaying buffer is removed by washing in a beaker of TE (10 mM Tris-Cl, 0.1 mM EDTA, pH 7.4) buffer. Excess TE buffer is removed with an aspirator. The surface is then stained with YOYO-1 (100 nM) fluorochrome from Molecular Probes and sealed with immersion oil to prevent drying. Preferably, Cargille Immersion Oil for Microscopy can be used. The surface-fixed molecules are ready for optical mapping.

Figure 30:
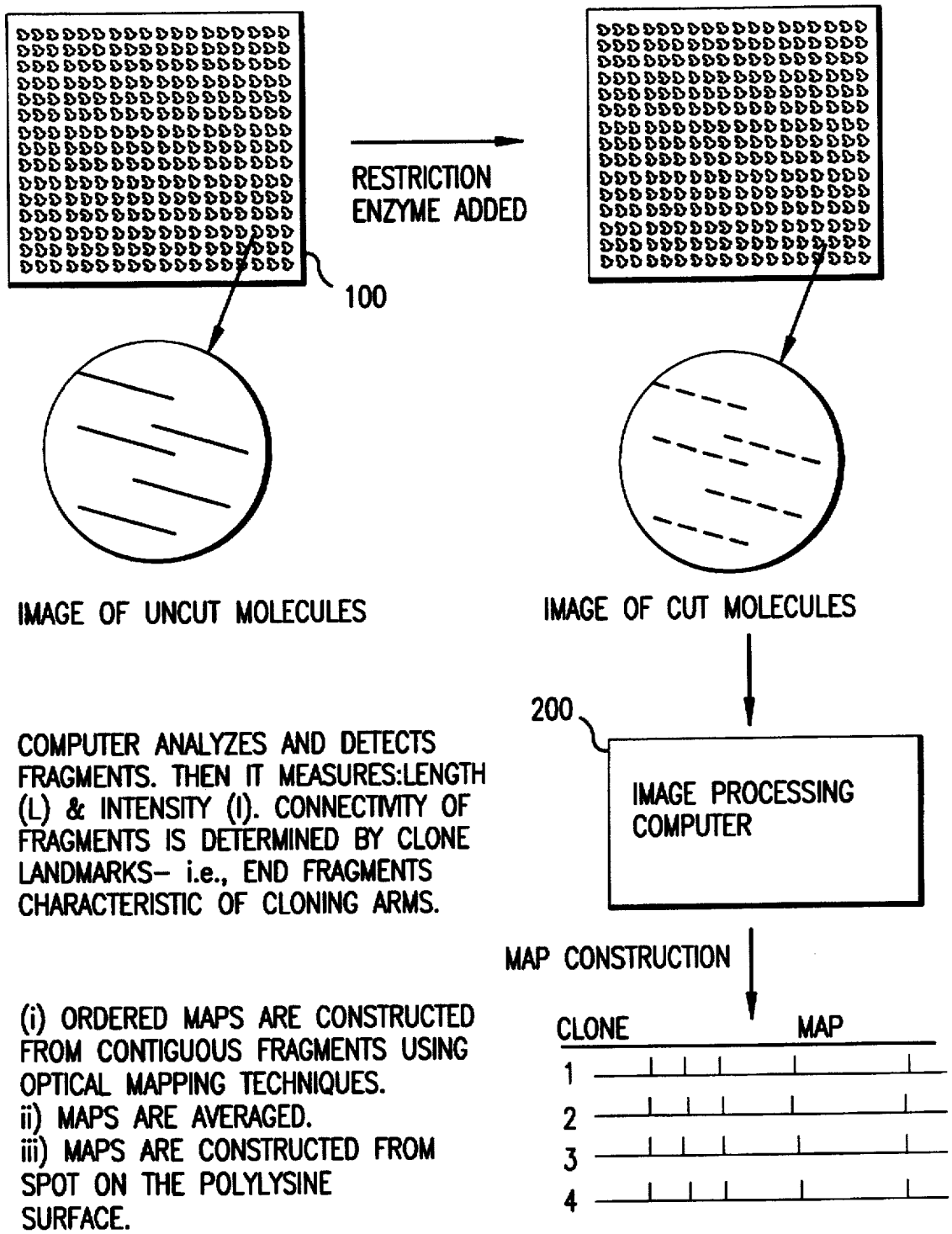
FIG. 30 is a block diagram of a method for high throughput optical mapping of lambda or cosmid clones.

FIG. 30 illustrates in a block diagram form the method of the present invention for high throughput optical mapping of lambda or cosmid clones. The figure illustrates the sequence of steps of robot-aided spotting of clones onto a rectangular derivatized glass plate 100; adding restriction enzyme; and image processing analysis in computer 200 after digestion.

High Throughput Optical Mapping of Gridded YAC DNA

Figure 31:
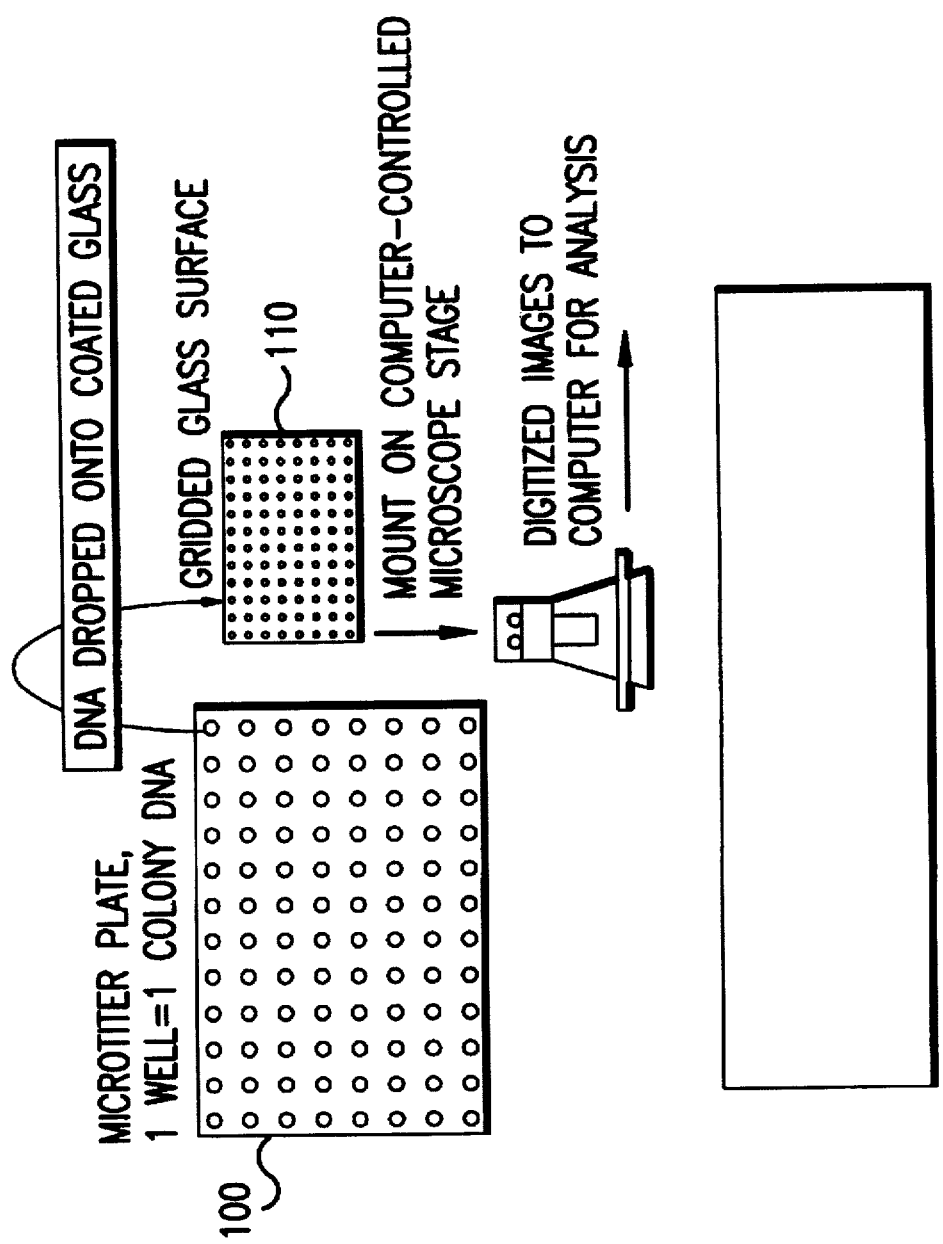
FIG. 31 is a block diagram of the system used for high throughput optical mapping of gridded YAC DNA.

FIG. 31 is a simplified block diagram of the system of the present invention when used for high throughput optical mapping of gridded YAC DNA. The system in FIG. 31 is an adaptation of the clone spotting system for YAC analysis which is a rapid, accurate system for YAC restriction mapping that readily interfaces with existing automated equipment yet is useful to laboratories lacking sophisticated sample handling technologies.

FIG. 31 shows one method for spotting YACs as intact chromosomal DNA molecules prepared in microtiter plates (100). The proposed approach uses yeast chromosomal DNA prepared in agarose. As seen in the figure, single droplets of molten-agarose are dropped onto a coated surface, such as polylysine-, or APTES-coated glass. Experimental results show that approximately 30–75% of dropped molecules are found on the surface with little breakage, even for megabased-sized molecules. Restriction enzyme is then added, and digestion proceeds for a defined period. Finally, a high-contrast fluorochrome, such as ethidium homodimer, is added and only imaged molecules fixed on the surface are taken for analysis. Note that fluorochrome addition is after fixation and digestion, avoiding possible fluorochrome-restriction enzyme conflicts. Imaging is also done post-digestion.

Alternatively, surface mounted DNA can be analyzed for map formation by adding restriction enzyme to the yeast chromosomal DNA molecules in the microtiter plate. Products are analyzed after mounting. Analysis techniques would include first end-labeling YACs, using other approaches. The high throughput approach again images restriction digestion products post digestion.

Spotting Intact YAC DNA:

Experimental data shows that YAC-sized DNA molecules suspended in molten agarose, can be elongated and fixed when gridded onto the surface as small droplets. The mounting procedure is as follows: a small amount of DNA embedded in agarose is dropped onto a treated surface (110). The droplet flows, DNA sticks to the surface and elongates. This technique is similar to spreading procedures used for karyotyping mammalian cells.

To increase the throughput and accuracy of the method, in accordance with one embodiment of this invention it is proposed to minimizing breakage, and optimize molecular elongation distributions. Ideally, it would be helpful to have all molecules perfectly positioned on a surface, completely biochemically active, and elongated by the same factor. This is a stringent set of specifications that in practice does not have to be met, since simple image processing routines can accommodate less than perfect data, given a sufficient sample size.

To this end, DNA concentration is varied systematically, changing pipetting variables (orifice size, delivery time, etc.) gel concentration, surface conditions (polylysine composition, and other compounds such as APTES, the temperature of surfaces and fluids. Coated glass surfaces are scored in a defined direction to provide sticky grooves for molecules to adhere to. The analysis uses fluorescence microscopy to measure the numbers of fixed molecules, distributions of apparent molecular lengths, and biochemical activities. Biochemical activity assayed by measuring the restriction digestion activity of previously mapped molecules bound on the surface. Importantly, this work does not involve molecules above the surface, trapped in the agarose gel layer.

For high throughput mapping it is also important to evaluate how dense spots can be dropped onto a surface. The Eppendorf micromanipulator/injector instrument is used as described above. The injector unit provides a very reproducible pipetting rate, as well as pipette filling time, and it is already interfaced with the micromanipulator. In this measurement, it is not possible to perform high-volume gridding, although micromanipulation is reproducible to a fraction of a micron. Molecular densities are optimized to maximize numbers of molecules imaged in a field without significant amounts of overlap and crowding, since crowding can complicate the recognition of individual molecules or fragments. Optimal mount conditions depend on a number of factors, molecular size being a major one. Approximately 5–10 500 kb molecules can be imaged simultaneously, using a 100× objective and our camera/digitizing systems. If restriction digestion efficiencies run approximately 20% (for full digestion), it is possible that accurate maps can be created from 50 to 100 molecules. This means that approximately 5–20 fields will be necessary to produce 1 to 10 fully digested, scorable molecules. In terms of space, this translates to a maximum of about $(0.5 \text{ mm})^2$ per spot. And 400 spots can be placed on a $(2 \text{ cm})^2$ coverslip, assuming a 1 mm center-to-center spacing between spots. A final consideration is preventing agarose spots from drying out during gridding operations. Possible solutions to this problem include performing gridding operations under high humidity, adding glycerol to the agarose (D.C.S., unpublished results), and pipetting through buffer covered with a layer of a light hydrocarbon.

Surface mounted molecules provide sharp, high contrast images. Most automatic image processing routines start with binary images since they are simple for the computer to interpret. The high contrast images obtained from surface-mounted DNA molecules are, in fact, almost ideal for creating binary images, since they require little or no processing outside of ordinary shading correction operations. Simple automatic imaging routines can be used discriminate a variety of individual DNAs. For example, optical mapping techniques to size resulting restriction fragments by measuring fluorescence intensities and molecular contour lengths. One of the problems using this approach is the recognition of useful molecules. From binary images of mounted DNA molecules "masks" can be created automatically, to guide optical mapping programs to recognize fragments, size them and create maps from them.

Molecules can be tagged and discriminated by changing fluorescence microscopy filter packs using a computer-controlled filter wheel. Naturally, tags are designed with spectral characteristics that differ from the bulk-stained molecule. Other molecular tagging approaches, that are compatible with optical mapping can also be used.

B. Image processing Equipment

In a preferred embodiment of the present invention imaging of the pretreated surface-fixed molecules is performed using a Zeiss Axioplan or Axiovert 135 microscope equipped for epi-fluorescence (filter pack for green excitation and red emission, or preferably a YOYO filter pack, 490 nm excitation, 510 nm emission) and Plan-Neofluar objectives (16×, 100×; made by Zeiss). The microscope is coupled to a Hamamatsu C2400 SIT focusing camera and an imaging Photometrics PXL Cooled CCD camera. The spatial resolution of the image processing equipment is 1032×1316 pixels per image, with 12 bits/pel raw image gray-level resolution and 16 bits operating resolution.

In a preferred automated embodiment of the present invention the output of the focusing SIT camera is used in a feedback loop for auto-focus control and positioning to adjust the x-y position of the spot being imaged. The electronic auto-focus unit and a stepping motor unit connected to the microscope focus control are provided by Ludl Electronics and is known in the art. This system acts as an automated microscope capable of automatically moving from one imaged spot to another.

In one embodiment of the present invention, the digitized images are stored for subsequent processing using a Macintosh computer. In this embodiment, a modified version of the commercial software package Ip Lab distributed from Signal Analytic, or a modified version of the NIH commercial software for Macintosh computers can be used as discussed below. In a preferred embodiment, the processing computer is a SUN workstation with 128 MB RAM and 32 GB hard drive space enabling continuous processing of large volumes of image data.

Figure 32:
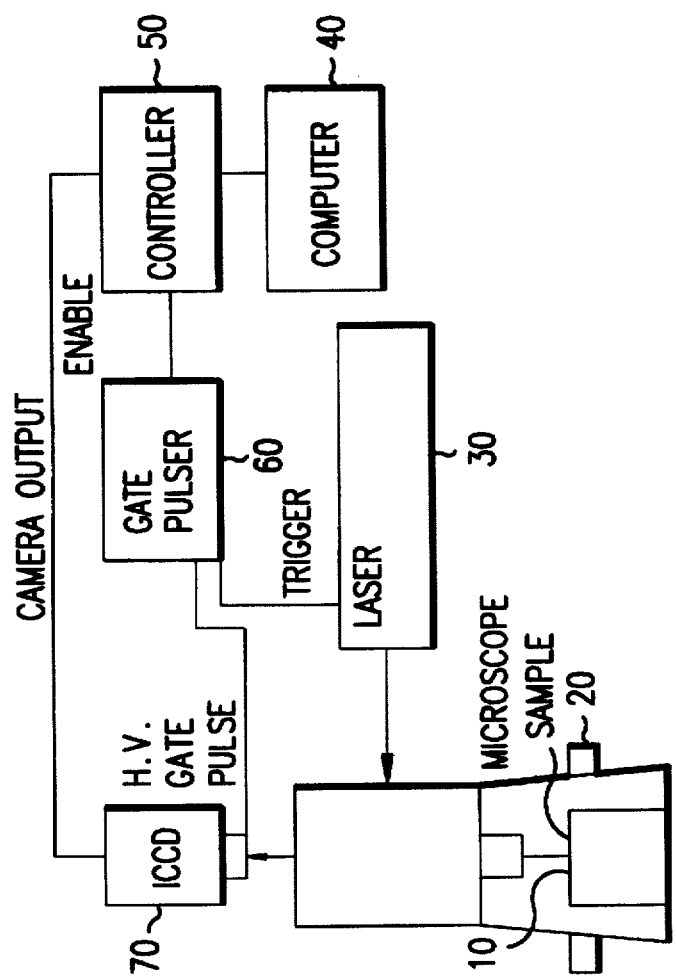
FIG. 32 is a block diagram of one embodiment of the automated system for high throughput optical mapping.

FIG. 32 is a block diagram of another embodiment of a system for optical mapping in accordance with the present invention which preferably includes a cooled CCD camera (Photometrics, AZ). While the equipment in FIG. 32 is less suited for high throughput measurements than the one described above, it can be used in certain applications which require the use of fluorescent lifetime microscope, as when it is necessary to distinguish life molecules.

In FIG. 32, microscope 20, is used to image sample 10 which is placed on computer controlled x-y table (not shown). Illumination for the microscope is provided by illumination source 30 which can be a mercury lamp or, in a preferred embodiment, a laser source. Computer 40 is connected to controller 50 which controls the operation gate pulser 60. In this embodiment of the present invention gate pulser 60 is connected to illumination source 30 and triggers a illumination pulse which results in a fluorescence emissions from the sample 40. These emissions are collected by microscope 20 and read out by ICCD camera 70 synchronously under the control of a gate pulse from gate pulser 60.

Fluorescent Lifetime Imaging

Figure 33:
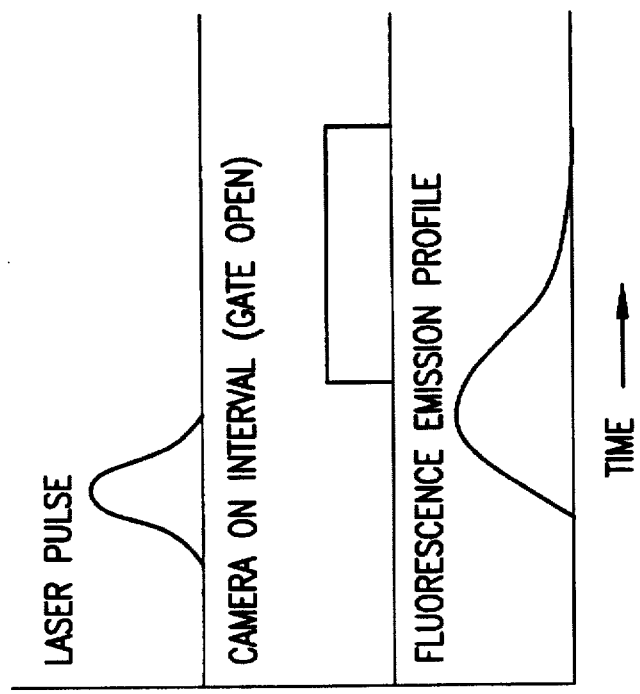
FIG. 33 illustrates a method of optimizing the image collection process and maximizing the signal-to-noise ratio.

FIG. 33 illustrates a method of optimizing the image collection process and maximizing the signal-to-noise ratio in accordance with the embodiment of the present invention which is illustrated in FIG. 32. The method is based on limiting the interval during which the camera can collect and record images to a time slot when the intensity of the illumination source has gone down to zero, as to eliminate stay light and scattering from this source.

As shown in FIG. 33, the heart of the imaging fluorescence lifetime microscope is the coiled image intensified charge coupled device, or, simply, ICCD. This low noise device can image under remarkably low light conditions that approach single photon counting levels. The signal/noise performance is at least twice as good as a frame averaged SIT camera. The ICCD is also gatable down to 5 ns, which is shorter than most fluorescent probe lifetimes. The intensification stage on this camera consists of a microchannel plate, which functions like a bundle of photomultiplier tubes, so that a small number of photons triggers an avalanche of electrons that hit a phosphor screen and produce a bright image. The phosphor screen image is sensed by a CCD chip attached to the intensifier by a fiber optic coupler, and the chip-born image is transferred into the camera controller and digitized. Similar devices are often used for military night vision equipment. As mentioned, the intensifier is gated so it can be opened and closed, just like a camera shutter. This "shutter", however, is very fast and has a gating ratio of greater than $5 \times 10^6:1$. The ICCD is a preferred imaging system for quantitative work using fluorescent lifetime microscopy.

To maximize the signal/noise ratio, exploitation of the gating feature of the ICCD is used to open the shutter only after the excitation pulse is finished, stray light and scattering from the illumination source thus being substantially eliminated. Hence, having created emission photons exclusively from fluorescence under controlled and careful timing of the image collection, bound from unbound emissions, or stray fluorescence, can be distinguished on the basis of fluorescence lifetimes.

As non-limiting example, for the ethidium bromide-DNA complex, the dye lasers are tuned to 525 nm, and the gate widths are set to 63 ns, since the lifetime of the bound species is 21.1 ns (93), so approximately 3 t should be optimal. The lifetime of unbound ethidium bromide fluorescence in water is only about 1.6 ns, so the free fluorochrome emission will closely follow the excitation laster profile and are easily selected against. Other sources of background fluorescence include immersion oil, glass slides and sample impurities, and fluorescence from these sources can also be attenuated with this technique.

Gated pulses can be are timed and synchronized with fluorescence decay. The gating pulser is timed to produce a high voltage signal during the fluorescence lifetime of the fluorochrome-DNA complex. The high voltage pulse opens and closes the electronic shutter. Illumination are pulsed with a 8 ns FWHM duration so that excitation is present only when the shutter is closed. Eliminating filters increase light throughput and remove another source of unwanted fluorescence. The laser excitation repetition rate is variable (1–100 Hz), and the fluorescence emissions accumulate as charge on the ICCD head; a resultant image builds up consisting of bright spots with intensities proportional to mass.

Two nanosecond lasers are appropriate for these methods, such as but not limited to, a Continuum Corporation Nd-YAG pumped TiSaphire tunable solid state laser and a Lambda Physik excimer pumped dye laser.

The sensitivity and size resolution of such system can be evaluated using EcoRI digests of lambda bacteriophage DNA stained with ethidium bromide. Images are generated in the described system and the spot intensities, corresponding to single molecules, are tabulated by our image processing routines. These are subsequently binned to obtain histograms depicting intensity populations which correspond to fragment size populations. This sort of analysis can be done according to (94) on DNA molecules flowing through a synthetic silicon matrix. The precision and accuracy of these measurements can be calculated and used to set proper bin widths for the histogram analysis.

DNA fragments preferably are in nearly perfect focus. If fragments are out of focus, intensity values can vary for the same sized molecule. To ensure that molecules are in focus, the surface mounting techniques described here can be used. Other methods may also include the use of centrifugal forces to spread DNA fragments in solution or gel out on a glass surface.

Non-uniform illumination can be corrected by a combination of careful illumination adjustments and by use of processing routines developed for relative intensity measurements in optical mapping. Essentially, this routine locates local surrounding pixels and uses their intensity values to calculate local background values. Local background values will compensate for uneven illumination and thus act as shading correction.

Other fluorochromes can be used, e.g. those having varying degrees of sequence specificity and, if appropriate, fluorochromes with complementary sequence biases used, such as ethidium homodimer and ethidium-acridine orange heterodimer. Contrast can be further improved by eliminating unbound fluorochrome. Ethidium monoazide (Molecular Probes, Inc.) is a fluorochrome that covalently attaches to DNA in high yield by photochemical means, and unbound compound can be readily extracted from the labeled DNA before mounting.

A series of well-defined DNA fragments is added to the sample as internal fluorescent size standards. The concentration of fluorescence intensity standards is adjusted so that they are readily identifiable in any histogram analysis. A nearly linear relationship between mass and fluorescence intensity is expected.

Fluorescence lifetime microscopes can also be used to improve intensity based sizing for larger fragments (50–1,000 kb) or 1–1,000,000 kb. The results of the above sizing analysis obtained for a restriction digest of a pure sample can be an optical fingerprint and analogous to a fingerprint (without the hybridization step) derived from gel electrophoretic methods. Ancillary methods can use this advanced sizing methodology to produce ordered maps from genomic DNA and YACs of particular individuals or populations or subpopulations at high speed.

5.4.2. IMAGE PROCESSING

A. Factors Affecting the Image Quality

A number of factors are known in the art to affect the quality of images obtained in molecular imaging. One of the main factors is the level of noise generated by the equipment. Such noise is related to fluctuations in the intensity of the light source; to electronic noise associated with the camera system: including its dark current, the level of radio frequency interference, etc. It has been experimentally determined that for the system of the present invention described above the noise factor is relatively insignificant and can be ignored in practical measurements.

The Zeiss Axioplan equipment used in accordance with a preferred embodiment of the present invention has automatic gain control and calibration as a result of which the calibration of the cooled CCD camera is simple and reliable. Problems associated with saturation have not been observed.

Figure 34:
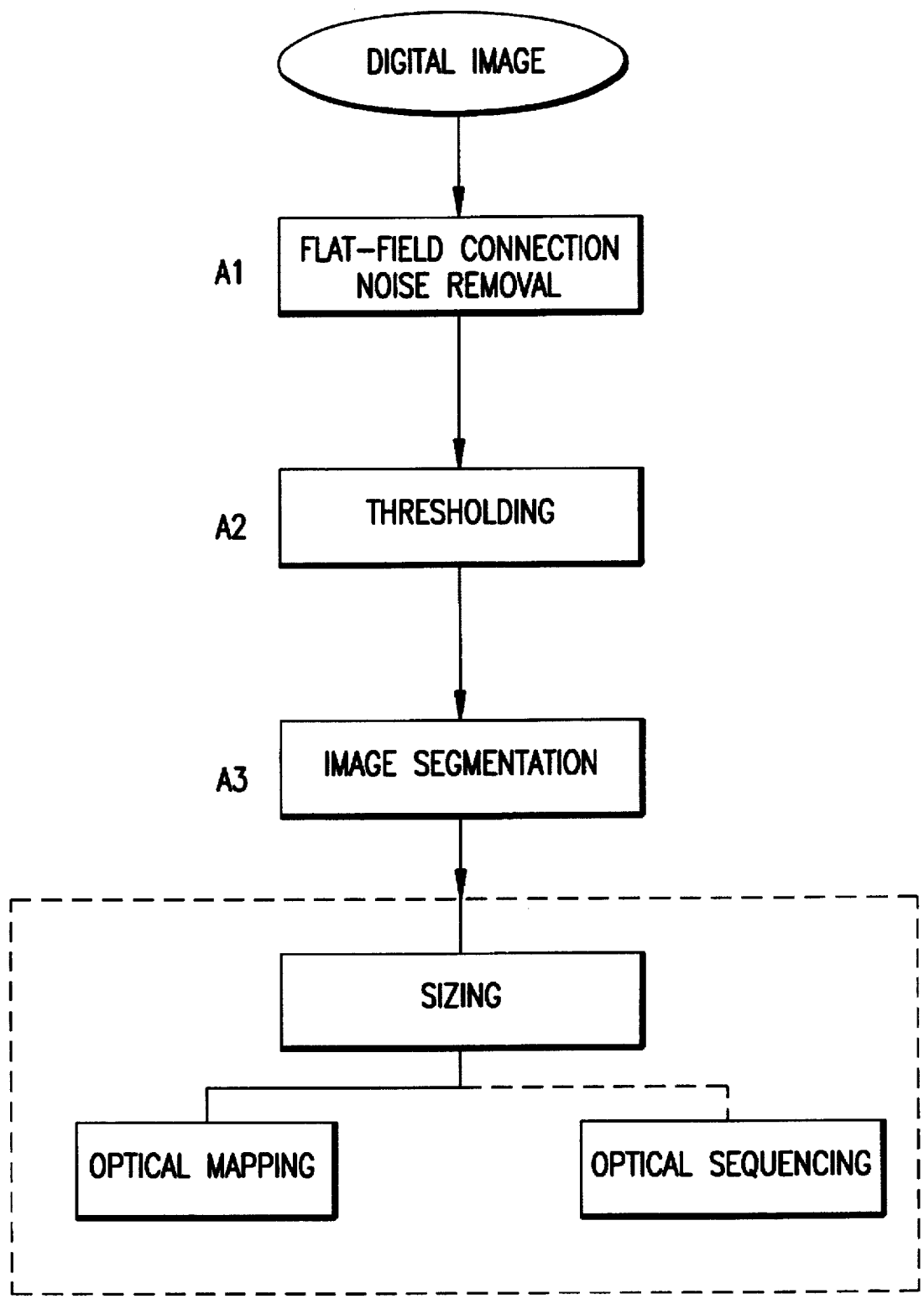
FIG. 34 is a block diagram of the image processing method in accordance with a preferred embodiment of the present invention.

FIG. 34 is a block diagram of the image processing method in accordance with a preferred embodiment of the present invention.

Step A1 of the method is a flat field correction of the raw image. The flat field correction is used to provide an image in which pixel values are proportional to the amount of dye present at each pixel location of the sample plane. It is typically required in cases when the illumination is not uniform over the entire field of view. It may also be used to eliminate the effects of imperfect image filters which may cause visible beat patterns similar to the Moire effect at the sampling frequencies of the system. The correction is based on the assumption that the emitted fluorescence is linear in both the amount of illumination in the field of view and that the camera response is linear.

Two auxiliary images are used to perform the flat field correction: a dark image (no input signal from the field of view) and the image of interest (an illumination image). Both images should be collected under identical conditions with no saturation of the video signal in which case the gray-level histogram of both images is distributed normally. In the next step, the dark image is subtracted on a pixel-by-pixel basis from the illumination image to generate a difference signal which is proportional to the level of illumination at the corresponding pixel of the image generated from the light striking the camera. The resulting difference signal at each pixel is then normalized by the value of the corresponding pixel in the illumination image to generate an image in which pixel values are proportional to the amount of dye in the sample.

The second step A2 of the image processing method in accordance with the present invention is to generate binary images which roughly correspond to and thus identify the contours of the desired molecule fragments. In the system of the present invention thresholding is automated on the basis of constructing a histogram of the image and setting the threshold level for binarization equal to the computed midpoint between gray levels corresponding to background (no light) pixels and gray levels corresponding to foreground, or molecular fragments. This step is well known in the art and will not be considered in further detail. In a preferred embodiment of the invention, the step of generating binary images is preceded by a filtering operation designed to remove spot noise or other artifacts that may affect the accuracy of the method. Preferably, such spot noise can be eliminated by the use of a 2-D median filter of size 5×5 or 7×7, as known in the art.

In step A3 of the method the imaged molecules are segmented on the basis of the thresholded images. Morphological operation of this type were described in some detail in Section 5.2. In one embodiment of the present invention, using NIH image processing routines, a seed fragment is selected by pointing near a desired fragment. An overlay image of the selected portion of the image field is next presented after a four-time dilation using pixel replication. Background correction may be used prior to the step of segmentation to reduce the effects of unbound dye or imperfect emission filters. In this processing step the average background pixel value is simply subtracted from each pixel of the image.

In a preferred embodiment of the present invention, segmentation of the image, including for example the computation of the medial axis of the imaged molecule, and the definition and storage of connectivity information is done automatically, as described, for example in Jain, 1989.

In one embodiment of the present invention the segmentation step A3 is complete with the identification of the DNA fragments. In a second, preferred embodiment of the present invention, the identification of fragments is followed by the step of boundary extraction and edge linking as part of a computer routine connecting molecule fragments into complete reconstructed molecules.

As shown in FIG. 34, the last step of the high throughput image processing involves sizing of the molecules which have been imaged followed by optical mapping, or possibly optical sequencing, as described in more detail next.

In accordance with a preferred embodiment of the present invention, it is proposed to use high throughput optical mapping to generate clone maps. The method includes the following steps:

(1) Imaging the molecules to obtain digital images of the clones being analyzed;

(2) Use relative fluorescent intensity or contour length to create maps from individual molecules. This involves computation of the relative sizes of individual fragments, as described in Section 5.2. above;

(3) Create a histogram of all measured molecules according to the number of cuts detected. As shown, for example in FIGS. 7A–7D the created histogram indicates the number of molecules having a specified number of cuts following digestion.

(4) For each histogram bin which corresponds to a specific number of cuts, use statistical analysis of the maps created in step (2) to obtain information about the clustering consistency of the cuts. This consistency measurements is determined by computing the pooled standard deviation within molecules of a single histogram bin. The consistency analysis is based on programs which minimize the Euclidean distance between members of a single cluster, and maximize the distance from other measurement clusters. This step of the method can, for example, be performed using a commercial statistics routine, such as Systat. (Thus, for example, in accordance with the present invention all molecules determined to have specified number of cuts are examined to determine the consistency of the spacial position of the cuts).

(5) In accordance with the present invention, the histogram bin which has the highest consistency (lowest pool standard deviation) and the largest number of fragments is used for further analysis purposes. Next, all individual fragment sizes within the selected bin are averaged to obtain the estimate of the desired ordered map. As indicated in Section 5.2.6 above, using sample averaging increases the measurement accuracy as sqrt(n).

(6) Maps can then be aligned (i.e. the largest fragment can be placed to the left, etc.) to generate the desired ordered map.

The proposed optical mapping approach is simple to implement and can thus easily be automated. Furthermore, due to the fact that a large number of measurements can be made in parallel, the method can provide very high throughput and also because of its high accuracy, is expected to provide an extremely valuable analysis tool for all kinds of practical applications.

C. De Novo sequencing

Optical sequencing is a genomic analysis technique which is likely to become especially important with the use of high speed optical measurements. The method was considered in some detail in Section 5.3 above. An important practical application of optical measurements of the rotational diffusion coefficients is to analyze the size distribution of a Sanger dideoxy sequencing ladder. Specifically, trimmed molecules are stained with ethidium bromide, mounted on the microscope stage and sized using the rotational diffusion methods described above.

The Sanger sequencing technology provides the ideal substrates: stiff, rod-like duplex DNA molecules, for determining rotational diffusion coefficients. Since the dependence of rotational diffusion coefficients on length has been experimentally determined for molecules in this size range (50–500 bp), a resolution of one base pair difference in size is realistic. For example a 200 vs. a 199 bp molecule will show a relative rotational diffusion coefficient ratio of 1.025; 100 and 99 bp, 1.0360. This worst possible case, at moderately long polynucleotides, shows there is still adequate resolving power. Furthermore, the data measured can be expected to be very accurate despite some errors in measurement, since the determined length varies as the time$^{1/3}$ measured.

The primer length has to be long enough to carry enough chromophore for detection of the smallest molecule in the ladder but not so long as to show random coil behavior. To keep size differentiation high, primer length should be minimized. Sensitivity could be a problem despite the extraordinarily high molar chromophore concentration contained within a small rod of DNA, since the total number of chromoforms is low. Therefore, the total fluorescence photon flux will likewise be low. Fortunately, a microchannel plate detector can detect single photons, although noisily. By connecting the microchannel plate detector to a sensitive SIT camera, and averaging using image processing techniques, proper data can be obtained.

A group of discrete molecules is used and size population histograms made. Careful statistical analysis is used to fully characterize a given sequencing ladder. To increase the throughput of the system, the image processing equipment can measure many objects in parallel. Since the measured molecules are small, it is possible to image intensity changes of thousands of molecules simultaneously.

The optical sequencing data rate in principle are many times faster than gel based methods. It is estimated that with millisecond relaxation times and multiple alignment/size determinations lasting 30 cycles/sequence and very fast computers, a 300 base pair ladder can be sized in 120 seconds assuming 4 reactions per sequence or a final rate of 9,000 bp/hour. This rate is approximately 15× faster than the automated sequencer rate presented in the National Academy report on mapping and sequencing the human genome (1).

5.4.3. DYNAMIC MEASUREMENTS

In accordance with one embodiment of the present invention, OCM dynamic molecule sizing, described in Section 5.2, can be modified to provide high throughput methodology by using a new physical effect to elongate molecules and new image processing methods to measure molecular lengths in real time. Specifically, in accordance with the proposed method, fluid-gel interfaces have been found to provide an optimal situation for differential frictional forces to act on an electrophoresing molecule and elongate it to nearly its full contour length. The net elongation force on the molecule in this case is determined by the differences in the DNA frictional coefficient in the gel matrix versus the fluid phase. More precisely, when a DNA molecule electrophoreses through a gel-fluid interface, the fluid frictional forces are much less than those posed in the gel matrix. These forces are, typically, at least 10-fold less, but differences can vary with gel concentration. Molecular conformation is dynamic within the gel matrix, but on the average it is relatively compact. Frictional forces are reduced when a molecule emerges from the gel matrix into the free solution presenting a differential force across the molecule sufficient to cause it to elongate. Immediately after a molecule completely pulls free of the matrix, elongation forces disappear, and the molecule relaxes back to a compact, free solution conformation. Reversing the electrical field sends the free molecule back into the gel matrix; this process can be imaged by taking a series of digital images, and measuring the apparent length of the molecule as it is elongated across the boundary between the gel matrix and the fluid; measurements can then averaged as many times as needed, depending upon the desired accuracy.

In another embodiment of the present invention, high throughput relaxation time measurements are performed by electrophoresing molecules through the gel-fluid interface described above, and estimating the molecular relaxation by measuring the optical length of the molecule at periodic intervals to quantitate the degree of relaxation. As discussed in Section 5.2, the changes of the apparent molecular lengths as a function of time can be fitted to a single exponential decay function to obtain the relaxation time.

In this embodiment, solution relaxation mechanisms are somewhat different than gel-based ones, in that coil segments are not confined to move within a tube, or a series of connected gel pores. Rather, in a free solution, elongated DNA molecules relax by evolving from a drawn-out prolate ellipsoid to a more symmetric, spherical conformation. Relaxation times are also shorter in free solution (generally 10-fold less): for example, a 500 kb molecule has a relaxation time of 4 seconds. However, since solution relaxation times are inversely proportional to the solution viscosity, measurements on small molecules can be made on a convenient time scale by simply adding glycerol or sucrose to increase viscosity. It is significant to note that the shorter relaxation times manifested by solution based relaxation measurements are advantageous for any high throughput approach because they can enable automated collection of images at regular intervals, which can then be used to determine automatically the desired relaxation times In a specific embodiment, the high throughput dynamic size measurement techniques can be performed by electrophoresing molecules through the interface at a rate of approximately 20-50 molecules/minute. Contour lengths can be measured and tabulated from stored data by the same techniques and computer algorithms developed for optical mapping and coil relaxation measurements, imaged, such as the non-limiting example of images from a SIT camera are rapidly digitized, frame averaged and stored as 16 bit files at a frame rate of 30/sec. For example, 120 file frame buffers can be used in the analyzing computer. This means that 120, 512×512 pixel images can be digitized and stored in as little time as 4 seconds. More rapid image storage is available by simply reducing image size, in which case the same hardware can store 480, 128×128 pixel images. Processing algorithms can thus size 5–10 molecules simultaneously by gathering approximately 10 images (averaging 4–16 frames together) in a 20 second interval. Using a 1 gigabyte hard disk provides storage space for close to 2,000 full frame images or sizing data for 1,000–2,000 molecules. Processing algorithms can be set up to work in batch mode and require approximately 3–5 hours to process 1 gigabyte worth of image data into 1,000–2,000 sizes tabulated on a spreadsheet. These processing times are based on unattended operation, but operator interfaces can also be used that permit convenient manual identification and marking of molecules for analysis.

High image quality greatly facilitates image processing. Fluorescence images of DNAs obtained in fluid rather than gel are brighter, sharper and relatively free of fluorescing artifacts. Consequently, they are preferred for unattended image processing since they can be transformed into reliable binary or digital images, which are easily processed. This high throughput sizing methodology can be tested and benchmarked by using a series of Not I digested yeast chromosomes mixtures (containing DNAs 30–900 kb), of increasing complexity. Statistical analysis to calculate the precision of single measurements can be performed and the ultimate accuracy of this methodology determined. Confidence intervals are determined to establish the minimum number of molecules necessary for adequate analysis of complex mixtures. This analysis will help determine the usable size resolution and size discrimination levels. Sources of noise and systematic error are detected and eliminated as much as possible, as discussed in more detail below. A lower size limit of 5–20 kb and an increased upper size limit are provided by the present invention since molecules with contour lengths greater than the microscope viewing field are sized by offsetting a known distance from the interface and monitoring only coil ends.

The following examples are offered in order to more fully illustrate the invention, but are not to be construed as limiting the scope thereof.

EXAMPLE 1

Preparing DNA for Microscopy

G bacteria was grown as described by Fangman, W. L., Nucl. Acids Res., 5, 653–665 (1978), and DNA was prepared by lysing the intact virus in ½× TBE buffer (1×: 85 mM Trizma Base (Sigma Chemical Co., St. Louis Mo.), 89 mM boric acid and 2.5 mM disodium EDTA) followed by ethanol precipitation; this step did not shear the DNA as judged by pulsed electrophoresis and microscopic analysis.

DNA solutions (0.1 microgram/microliter in ½× TBE) were diluted (approximately 0.1–0.2 nanogram/al agarose) with 1.0% low gelling temperature agarose (Sea Plague, FMC Corp., Rockport Me.) in ½× TBE, 0.3 micrograms/ml DAPI (Sigma Chemical Co.), 1.0% 2-mercaptoethanol and held at 65° C. All materials except the DNA were passed through a 0.2 micron filter to reduce fluorescent debris. Any possible DNA melting due to experimental conditions was checked using pulsed electrophoresis analysis and found not to be a problem.

EXAMPLE 2

Imaging DNA in a Gel

The sample of Example 1 was placed on a microscope slide. To mount the sample, approximately 3 microliters of the DNA-agarose mixture were carefully transferred to a preheated slide and cover slip using a pipetteman and pipette tips with the ends cut off to reduce Shear. Prepared slides were placed in a miniature pulsed electrophoresis apparatus as shown in FIGS. 1 and 2. All remaining steps were performed at room temperature. Samples were pre-electrophoresed for a few minutes and allowed to relax before any-data was collected. Pulsed fields were created with either a chrontrol time (Chrontrol Corp., San Diego, Calif.) or an Adtron data generating board (Adtron Corp., Gilbert, Ariz.) housed in an IBM AT computer and powered by a Hewlett Packard 6115A precision power supply. Field Strength was measured with auxiliary electrodes connected to a Fluke digital multimeter (J. Fluke Co., Everett, Wash.). A Zeiss Axioplan microscope (Carl Zeiss, West Germany) equipped with epifluorescence optics suitable for DAPI fluorescence and a Zeiss 100× Plan Neofluar oil immersion objective was used for visualizing samples. Excitation light was attenuated using neutral density filters to avoid photo-damage to the fluorescently labeled DNA. A C2400 silicon intensified target (SIT) camera (Hamamatsu Corp., Middlesex, N.J.) was used in conjunction with an IC-1 image processing system (Inovision Corp., Research Triangle Park, N.C.) to obtain and process video images from the microscope. Images were obtained continuously at the rate of one every five or six seconds, and as many as 200 digitized images could be stored per time course. Each digitized time-lapse image benefitted from the integration of 8 frames obtained at 30 Hz, which was fast enough to avoid streaking due to coil motion. After the time-lapse acquisition was complete, the microscope was brought out-of-focus and a background image was obtained. Each time-lapse image was processed by first attenuating a copy of the background image, so that the average background intensity was 82% of the average time-lapse image intensity. The attenuated background was subtracted from the timelapse image and the resultant image was then subjected to a linear-stretch contrast enhancement algorithm. Photographs of the processed images were obtained using a Polaroid Freeze Frame video image recorder (Polaroid Corp., Cambridge, Mass.).

EXAMPLE 3

Perturbing Molecules in a Gel

The molecules of Example 2 were perturbed by POE. POE was accomplished by using a series of relatively short normal pulses of a chosen ratio and then after a longer time period, the polarity of one of the fields was switched. The switch time and normal field ratio are analogous to the pulsed electrophoresis variables of pulse time and field angle.

The nomenclature used to describe a POE experiment is as follows: 3.5–80 second pulses, 3 volts/cM). "3.5–80 seconds" means a 3 second pulse south-north, followed by a 5 second pulse east-west; after 80 seconds of this 3.5 second cycle, the polarity of the 5 second pulse is changed (west-east) for another 80 seconds, and a zig-zag staircase path is defined for the molecules involved. The pulse intensity was 3 volts/cM. In this Example, epifluorescence microscopy was coupled with the POE method to enable the general study of DNA conformational and positional changes during electrophoresis. While the POE method using the adapted microscopy chamber shown in FIG. 2 was used in this experiment, ordinary electric fields switched on and off could have been used. POE offers certain advantages when electric fields are to be applied at different angles, as may be needed to rotate a molecule about its long axis. FIGS. 1 and 2 show diagrams of the adapted POE chamber.

EXAMPLE 4

Observing and Measuring Molecular Relaxation in a Gel

The relaxation of the G bacteriophage DNA of Examples 1–3 was observed after POE was conducted for 600 seconds (3.580 second pulses, 3 volts/cm).

Figure 3A:
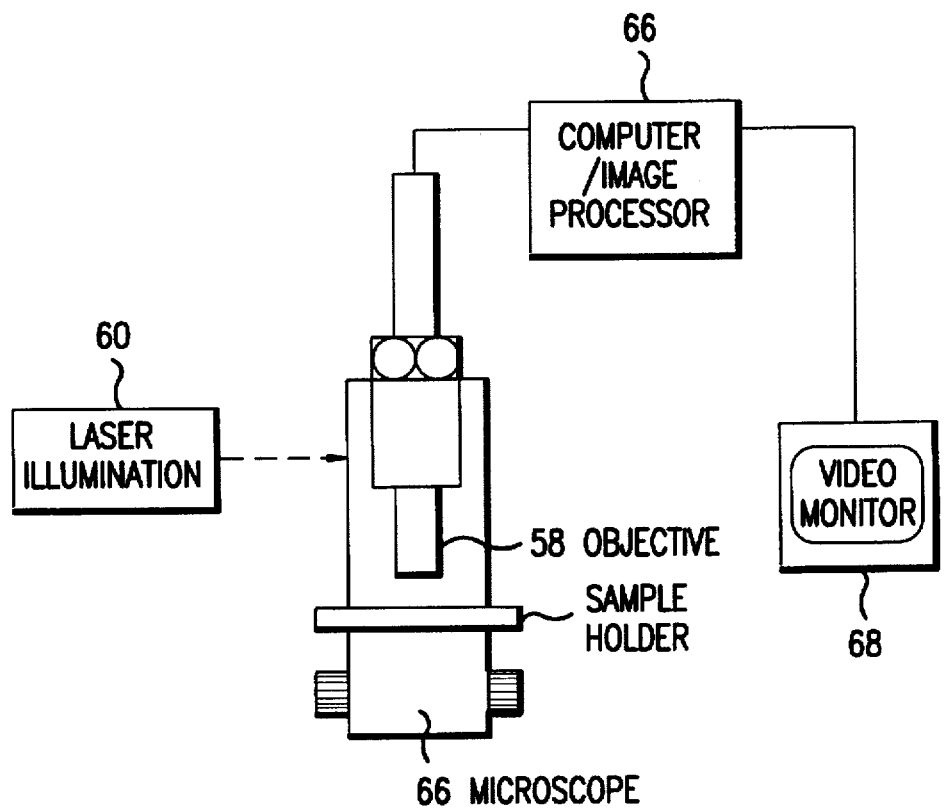

The image processor is used to quantify and automate the imaging of the relaxation process, for example, through "feature analysis". Feature analysis works after successive images have been digitized and stored, as shown in FIG. 3A. The image processor then identifies discrete objects in the images, numbers them, and characterizes them according to shape. For example, the computer determines the effective ellipsoid axes (long and short) for a collection of distorted coils and calculate these features as a function of time as the coil approaches a spherical conformation during the relaxation process. Other types of computerized measurements also can be made to characterize the DNA.

The images displayed in FIGS. 5A–5J, obtained at 12 second intervals, show the relaxation of several molecules over a 96 second time span. In (a), several coils are shown 3 seconds after the applied field was turned off. The coils appear to relax through the same corrugated staircase path defined by the applied electrical pulses (see molecules marked by arrows) as determined by the limits of microscopic resolution. In (c), a molecule is shown splitting into two, and by (j), all coils have relaxed to a round, unelongated conformation. The bar shown in (j) is 10 microns in length.

EXAMPLE 5

Determining the Molecular Weight of One or More Molecules by Measuring Relaxation Kinetics Molecules of known molecular weight are prepared for imaging according to the procedures of Examples 1–3, and the relaxation time of the molecules is determined by the methods of Examples 1–4. Relaxation time data is collected by imaging and is used to calculate a mathematical relationship between molecular weight and relaxation time of DNA molecules of similar composition. The relaxation time of a sample of molecules of unknown size is then measured, and the size of the molecules is calculated Using the mathematical relationship determined on the basis of molecules of known size.

EXAMPLE 6

Determining the Molecular Weight of One or More Molecules by Measuring Reorientation Rate in a Gel Polymers of any size, but particularly those that are too small to image (less than approximately 0.1 micron), are sized in a matrix such as agarose or polyacrylamide gel by measuring the reorientation rate as induced by an applied electrical field. Although a reorientation measurements could be done in free solution, a matrix is preferred because it prevents unnecessary polymer convection and movement. Additionally the presence of a matrix may enhance the size sensitivity, partly because the orientation mechanism is different. POE is particularly useful for measuring reorientation time because of its experimental versatility and very high size resolution of perhaps 15 to 20 megabases. Stiff polymers such as DNA molecules (sized less than 150 base pairs) exist in solution as rods and the rotational diffusion coefficient (the friction felt by the rod as you try to spin about its long axis) varies as M3. Using microscopy, molecules which are large enough to be imaged are visualized, and their reorientation time is determined from the images. For any size of molecules, particularly those which are too small to visualize, the reorientation time of each rod in the field of view is preferably measured by spectroscopic methods. Two such methods are described in detail below, namely fluorescence dichroism and birefringence:

1) A chromophore that binds in a sterically predictable way (ethidium bromide intercalates into DNA molecules) is attached to a polymer molecule. Polarized radiation is used to excite the chromophore. Measuring the total fluorescence intensity temporally provides orientation information of each molecule. The fluorescence radiation of each molecule in the microscope field is measured using a sensitive microchannel plate detector.

2) The orientational dynamics of a molecule is followed with birefringence measurements. Birefringence techniques measure the change of refractive index, which is easily correlated with the orientation of macromolecules in solution or in a matrix. Birefringence measurements are taken while the DNA molecules are undergoing gel electrophoresis. When an electrical field is applied, the DNA molecules stretch out and align with the field, thereby changing the refractive index. By measuring the change of birefringence with time, it is possible to understand details of DNA blob train motion as the molecule orients with the applied electrical field.

Figure 3B:
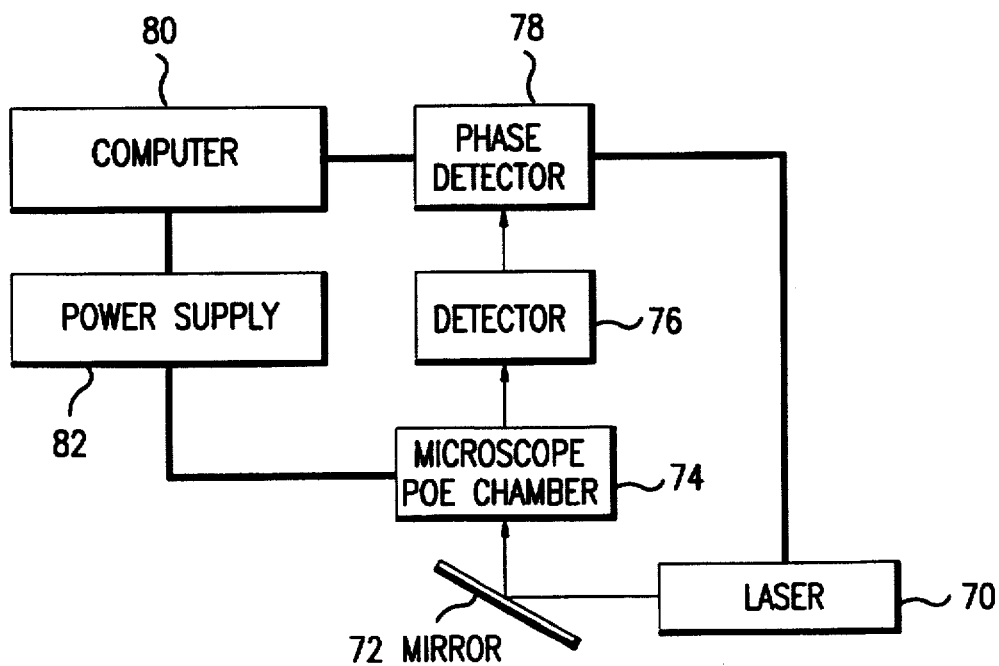
Figure 4A:
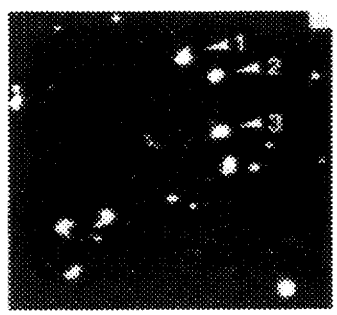
Figure 4B:
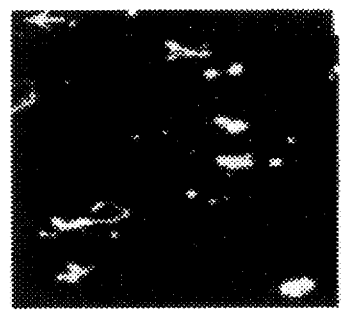
Figure 4C:
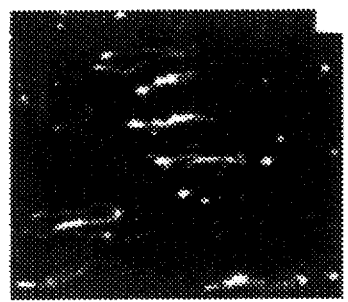
Figure 4D:
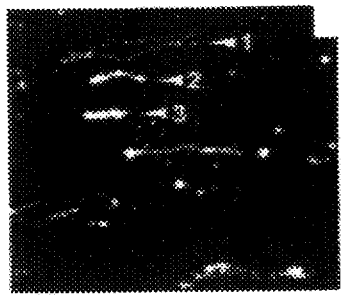
Figure 4E:
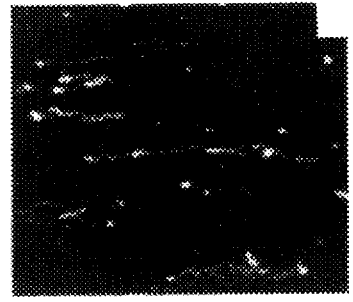
Figure 4F:
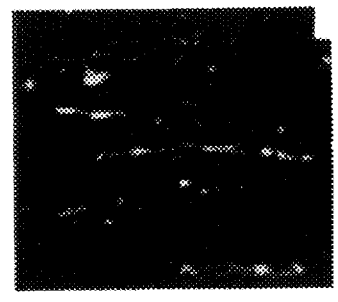
Figure 4G:
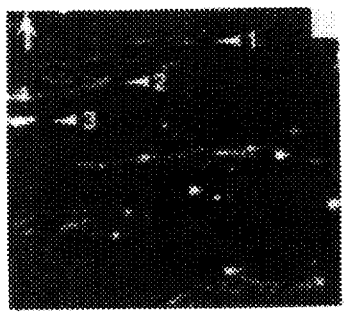
Figure 4H:
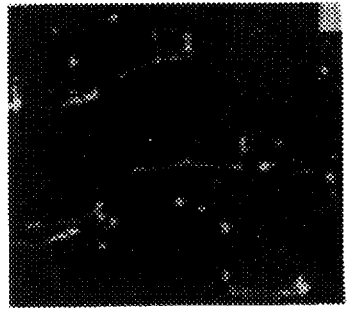
Figure 4I:
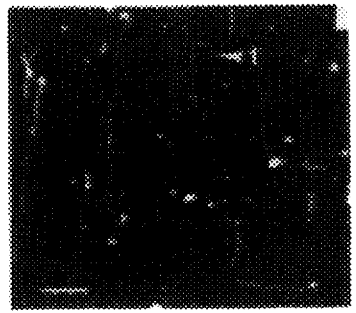
Figure 5A:
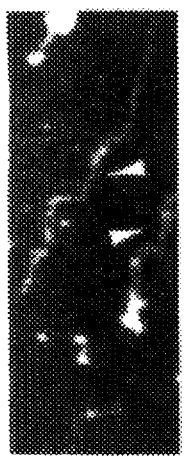
Figure 5B:
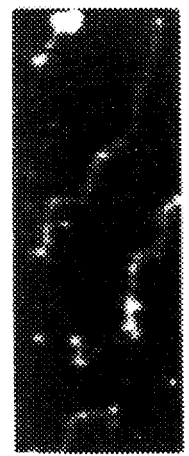
Figure 5C:
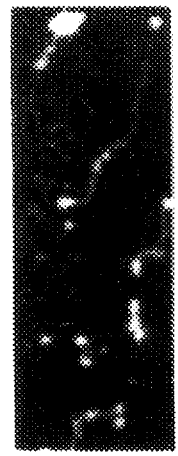
Figure 5D:
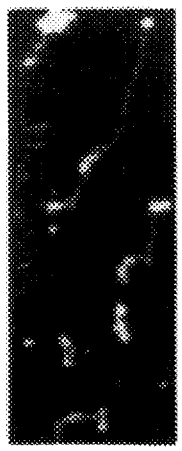
Figure 5E:
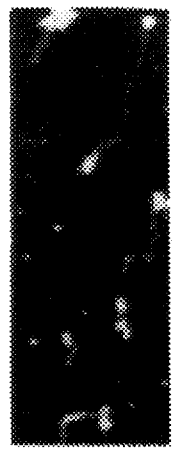
Figure 5F:
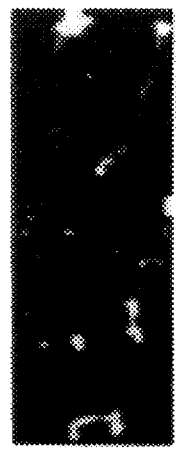
Figure 5G:
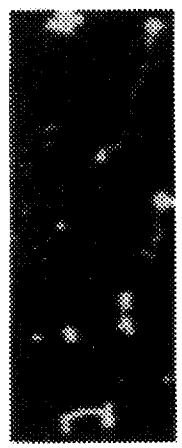
Figure 5H:
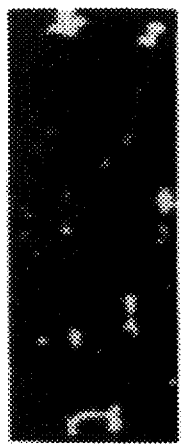
Figure 5I:
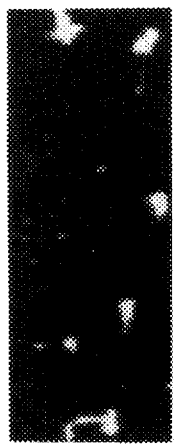
Figure 5J:
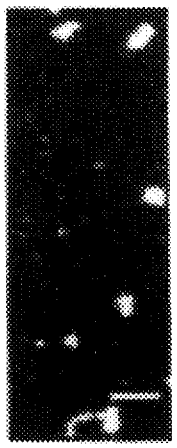

More specifically, birefringence measurements are made by determining the phase difference of two orthogonally polarized planes of laser radiation (red light) differing by a small frequency difference (supplied by the two frequency laser). As the molecules align with the applied electrical field (in the POE chamber), which is generated by pulse controller 82, the refractive index changes with molecular alignment. Light is detected by detector 76, and results in a phase difference in the transmitted radiation, which is measured by the phase detector 78 (FIG. 3B) by comparing the value to a standard, sourced at laser 70. The phase difference data obtained as a function of time (the period of field application) is digitized and stored on computer 80 for later retrieval and analysis.

The instrument depicted in FIGS. 1 and 2 applies the necessary fields to cause molecular reorientation. Many different rotational schemes can be described to optimally size molecules in the field. For example, the rotating field frequency can be swept to find resonant frequencies with the polymer sample.

EXAMPLE 7

Determining the Molecular Weight of One or More DNA Molecules by Measuring the Rotation Time of the Molecules in a Gel Molecules in the shape of rods or stiff coils are prepared and observed as in Examples 1–4, except that an acrylamide, rather than agarose gel optionally may be used.

The rate of rotation of a coil or a rod is measured with a microscope-based system using any one of the techniques described above in Example 6. Measurements are made of a sinusoidally varying signal as the molecule spins about its center. The sinusoidal signal is used to determine the polymer size or molecular weight by fitting the period of the sinusoidal signal to the rotational frictional coefficient, which varies as the cube power of the rod length. In other words, the measured angular velocity as measured from the sinusoidal signal (radians/sec.) varies as the rod length cubed in free solution (Boersma, S. (1960) J. Chem Phys. 32: 1626–1631, 1632–1635).

The conditions for a proposed series of experimental runs, with constant t, are shown below.

| M MolecularSize (base prs or kilo bases) | E ElectricField Strength (volt/cm) | Δt Duration of each Pulse (Sec) | $\theta_i$ Incremental angle (in clockwise direction (Deg.) |
|---|---|---|---|
| 50 bp  | 5 | $1 \times 10^{-4}$ | 10 |
| 150 bp | 5 | $1 \times 10^{-4}$ | 10 |
| 50 kb  | 5 | 1 | 10 |
| 500 kb | 5 | 5 | 10 |
| 500 kb | 5 | 900 | 10 |

Thus, in the first example, pairs, triplets or other sets of pulses of 5 volts/cm are successively applied for 0.1 millisecond in opposite directions, with the direction of the first of each successive set of pulses increasing by 10 degrees in a clockwise direction away from the starting point.

Molecules of known molecular weight are placed in a gel, and their rotation rate is determined when the above-described electric fields are applied. Rotation time data is collected and is used to calculate a mathematical relationship between molecular weight and rotation time of G bacteriophage DNA molecules in a particular gel. The rotation time of molecules of unknown size is then measured, preferably using a similar electric field, and the size of the molecules is calculated using the mathematical relationship determined on the basis of molecules of known size.

EXAMPLE 8

Determining the Molecular Weight of One or More Molecules by Measuring Curvilinear Length of DNA Molecules in a Gel The procedure of Examples 1–4 is followed for molecules of known molecular weight. Measurements of the curvilinear length of the molecules while they are in a perturbed state is collected by visualizing the molecules and is used to calculate a mathematical relationship between molecular weight and length. The curvilinear length of perturbed molecules of similar composition and unknown size is then measured using the procedures of Examples 1–4, and the size of the molecules is calculated using the mathematical relationship determined on the basis of molecules of known size. FIGS. 4 and 5 show perturbed molecules for which curvilinear length measurements can be made.

EXAMPLE 9

Determining the Molecular Weight of One or More Molecules by Measuring Diameter of DNA Molecules in a Gel The procedure of Examples 1–4 is followed for molecules of known molecular weight, except that measurements are made when the molecules are in a completely relaxed state. Measurements of the diameter or diameters of the substantially spherical or ellipsoidal G bacteriophage DNA molecules are collected and are used to calculate a mathematical relationship between molecular weight and diameter of G bacteriophage DNA molecules in the gel. The diameter of molecules of unknown size is then measured, and the size of the molecules is calculated using the mathematical relationship determined on the basis of molecules of known size. FIGS. 4A through 5J show relaxed molecules for which diameter measurements can be made.

EXAMPLE 10

Preparing Large DNA Molecules for Imaging

Chromosomal DNA molecules from *Saccharomyces cerevisiae* were prepared and isolated using the insert method and pulsed electrophoresis. Low gelling temperature agarose gel (FMC Corp. Rockland Me.) was used for preparation to permit relatively low temperature melting. Since UV radiation can break DNA molecules, desired bands were cut out of the gel, guided by ethidium stained flanking edge sections that were cut out of the gel, guided by ethidium stained flanking edge sections that were cut out of the gel, which were then photographed on a 301 nm transilluminator apparatus. The bands were then weighed and equilibrated with a 10-fold excess of 10 mM spermine in water for 3 hours at room temperature. Spermine requires a very low ionic strength environment to condense DNA and, fortunately, the buffers used in electrophoresis are low ionic strength, thus eliminating the need for an equilibration step. The equilibrated samples were then melted in an oven at 74° C. for two hours and after melting. DAPI (1 microgram/ml) and 2-mercaptoethanol (1%) were added. 3 microliters of the melted agarose/DNA mixture were carefully applied to a pre-heated microscope slide and a cover slip was placed on top before the mixture gelled. The slide was then viewed using a Zeiss Axioplan epifluorescence microscope fitted with a 100× Plan Neofluar objective and showed small intensely bright balls which could be decondensed by the addition of salt, through the edges of the coverslip sandwich.

As mentioned above, spermine is particularly useful in an environment of low ionic strength. On the other hand, if DNA molecules are placed in a highly ionic environment, the same type of condensation effect are accomplished with alcohol. Neither of these examples are to be construed as limiting the scope of the invention.

EXAMPLE 11

Restriction mapping *Schizosaccharomyces pombe* Chromosomal DNA Molecules

The DNA of *Schizosaccharomyces pombe*, a fungus with a genome size of about 17–19 megabases distributed on three chromosomes 3, 6 and 8–10 megabases in size, is prepared for microscopy by condensation and uncollapsing, according to the method of Example 10. The 3–5 microliter agarose mixture contains approximately 0.1 nanograms of DNA, 0.5% b-mercaptoethanol, 1 microgram/ml DAPI, 100 micrograms/ml bovine serum albumin (acetylated; Bethesda Research Laboratories, Gaithersburg, Md.) and 10–20 units of an appropriate restriction enzyme. This mixture is briefly held at 37° C. and carefully deposited on a microscope slide and then topped with a coverslip. Prior to digestion with restriction enzymes the DNA is stretched by one of two ways: (1) the liquid slide/agarose/coverslip sandwich is optionally sheared slightly by moving the coverslip or (2) an electrical field is applied using, for example, the POE instrument described in FIGS. 3A–3B. A 10 mM magnesium chloride solution is then diffused into the sandwich once the gel has set. When the magnesium ions reach the DNA/enzyme complex, the enzyme cleaves the DNA molecule.

The positions of the restriction cutting sites are determined by following the DNA strand from one end to the other using the microscope setup and noting cut sites. These sites appear as gaps in the strand, which is continuous before enzymatic digestion. The size of each of the fragments is then determined by the microscopic methods of this invention, including, (1) measuring the curvilinear length of each fragment, (2) allowing the fragments to relax and measuring their diameter, (3) perturbing the conformation of each fragment with an applied electrical field or flow field (as generated by moving solvent through a gel) and measuring the relaxation kinetics with direct visual detection of conformational and positional changes or microscopy combined with spectroscopy. Direct visual observation is preferred for larger molecules, while the other methods are well suited for fragments too small to image.

The resulting sample when viewed using a fluorescence microscope shows a number of bright balls of three different sizes, with diameters varying as M.33, which is based upon the formula for the volume of a sphere, 4/3R3. The gel also contains a restriction enzyme which is active only when magnesium ions are present.

EXAMPLE 12

In situ Hybridization of Nucleic Acid Probes to Single DNA Molecules

Nucleic acids are prepared for microscopy as described in Examples 1–4 above. The agarose medium containing the nucleic acid molecules also contains labelled probes and a recombinational enzyme, recA, which mediates strand displacement of the target molecule by the probe. Strand displacement and pairing occurs by D-looping (see Radding, C., Ann.Rev. Genet. 16:405–37 (1982)). ATP and magnesium ions are added to begin the reactions. These ingredients are diffused into the slide/gel/coverslip sandwich as described in Example 11. The reaction is incubated at 37° C. Many different target molecules are simultaneously analyzed, using probes with different labels.

Variations of the method of this invention other than those specifically described above are within the scope of the invention. For example, other parameters of the molecules can be measured, and various type of microscopes and spectroscopic equipment may be used. The pulsing routines for effecting molecule rotation can be varied. Combinations of the above-described techniques are also contemplated. For example, combinations of various types of external forces, mediums and spectroscopic techniques are within the scope of the invention. Furthermore, a measuring technique may be repeated several times, and the measurements from each trial may be averaged.

EXAMPLE 13

Figure 6:
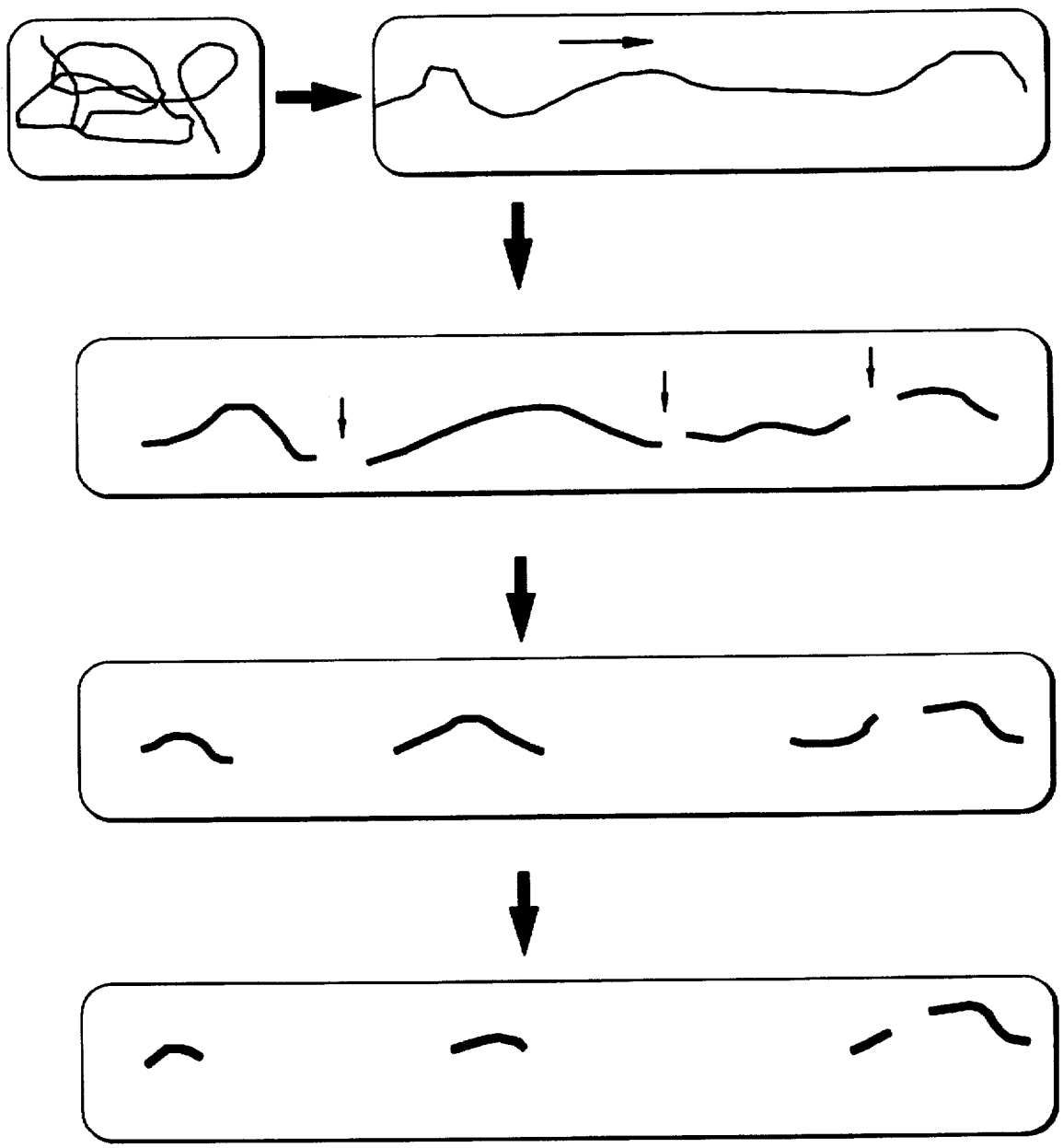

Ordered Restriction Maps of *Saccharomyces cerevisiae* Chromosomes Constructed by optical mapping Optical mapping (e.g. as shown in FIG. 6), images are made stained, single, deproteinized DNA molecules during restriction enzyme digestion, allowing direct, ordered mapping of restriction sites. In brief, a flow field (or in principle, or other kinds of electrical field) is used to elongate DNA molecules dissolved in molten agarose and fix them in place during gelation.

As a non-limiting example, yeast chromosomal DNA (yeast strain AB972) was resolved by pulsed electrophoresis (Schwartz et al., *Cell* 37:67 (1984)) using 1.00% Seakem low melting agarose (FMC), ½× TBE(42.5 mM Trizma base, 44.5 mM boric acid, 1.25 mM disodium EDTA). Cut gel bands were repeatedly equilibrated in TE (10 mM Tris-Cl, 1 mM EDTA, pH8.0). The gel embedded, purified chromosomes were then equilibrated overnight at 4° C. in magnesium-free restriction buffer containing 0.1 mg/ml acetylated bovine serum albumin, 1% β-mercaptoethanol, 0.1% Triton X-100 (Boshringer Manheim, membrane quality), and 0.2 ug/ml 4', 6-diamino-2 phenylindole dihydrochloride (DAPI) with slow shaking. Equilibrated samples ranging in volume from 50 to 100 ul were melted at 72° C. for 5 minutes, and then cooled to 37° C. Approximately 0.3–0.5 ul of enzyme (2 to 14 units/μl) was spread on a slide. Enzyme reaction temperatures were as recommended by manufacturers. β-mercaptoethanol was added to discourage photolysis M. Yanagida et al. in *Applications of Fluorescence in the Biomedical Sciences*, D. L. Taylor et al., Eds. (Alan R. Liss, New York, 1986), pp. 321–345. and was tested at this concentration for any deleterious effects on digestion using electrophoresis. A 7 μl volume of the melted sample was typically pipetted (slowly) using a wide bore pipette tip onto an 18×18 mm cover glass and rapidly deposited onto a slide. Timing and quenching of the gel is critical for controlling elongation. The reaction chamber was then sealed with mineral oil to avoid evaporation, and the agarose was allowed to gel for at least 30 minutes at 4° C., prior to diffusion of 50 mM MgCl2 through an open space. For chromosome I(240 kb) and III (345 kb), slides were in a cold desiccator (4°) prior to casting to hasten gelling avoiding premature molecular relaxation. For the larger chromosomes, which relax more slowly, slides were kept at room temperature. The slide was placed on a temperature controlled microscope stage at 37° C. (except CspI, 30° C.). The gelatin process restrains elongated molecules from appreciably relaxing to a random coil conformation during enzymatic cleavage. A restriction enzyme is added to the molten agarose-DNA mixture and cutting is triggered by magnesium ions diffused into the gelled mixture (mounted on a microscope slide). Cleavage sites are visualized as growing gaps in imaged molecules. DNA molecules were imaged using a Zeiss Axioplan or Axiovert 135 microscope equipped for epi-fluorescence (487901 filter pack for UV excitation and Blue emission) and a 100× or 63× Plan-Neofluar objective (Zeiss) coupled to Hammamatsu C2400 SIT cameras. Care was taken to adjust the camera controls to avoid saturating the digitizer at either end of the intensity range. Every 20 seconds, 32 video frames were digitized to 8 bits and integrated to give 13 bit precision by a Macintosh based Biovision image processor or a Pixel pipeline digitizer (Perceptics Corp.). A computer controlled shutter was used to limit illumination to 1.5 seconds per image giving a total of about 135 to 255 seconds for typical experiments. Neutral density filters were used to keep the illumination intensity below 100 μW measured at the objective. Control experiments showed no damage to DNA molecules under these conditions. Digitized images were recorded directly to disk and archived on tape. The resulting fragments are sized in two ways: by measuring the relative fluorescence intensities of the products, and by measuring the relative apparent DNA molecular lengths in the fixating gel. Maps are subsequently constructed by simply recording the order of the sized fragments. Length and relative fluorescence intensity were calculated to 16-bit precision using a modified version of NIH Image for Macintosh by Wayne Rasband, available upon request from the authors (e-mail huff@mcclb0.med.nyu.edu). Briefly, the original unprocessed image was displayed in an enlarged format and an overlay image was prepared by manually tracing the DNA. The length map was made directly from this overlay. For intensity calculations, the 13-bit raw data image was smoothed and the overlay image was dilated five times to cover all foreground pixels. For each pixel marked on the overlay, a synthetic background value was calculated as the weighted average of surrounding pixels, with a weight that decreased with distance, but was zero for all marked pixels. These values are intended to approximate those which would have been measured had the DNA been absent. The intensity of a particular DNA fragment was the sum of all pixels of the fragment minus the matching background pixels. The are of the fragment was the original overlay dilated twice. This process was repeated for each frame of raw data which had an overlay image, excluding those with poor focus. Intensity results were averaged for five images following a cut, and the relative sizes of the two fragments were calculated as $x/(x+y)$ and $y/(x+y)$. If fragment y later cuts into u and v, then $(y/(x+y))(u/(u+v))$ is used for the size of u. The resulting numbers constitute a single sample for the purposes of subsequent analysis. Averaging a small number of molecules rather than utilizing only one improves accuracy and permits rejection of unwanted molecules. The samples were averaged and the 90% confidence interval on the mean was calculated using the t distribution with n−1 d.f. and the sample standard deviation. This calculation is valid if the data represent random samples from a normal distribution. There is a 90% chance that the population mean falls within the confidence interval. For chromosome I, the reported confidence interval was found by taking the lower bound from the short fragments and upper bound from the long fragments. The 90% confidence interval for the population standard deviation was calculated using the sample standard deviation, the number of samples, and the chi-square distribution with n−1 d.f. The midpoint of this interval was used to estimate the population standard deviation. The coefficient of variation (CV) is the estimated population standard deviation divided by the sample mean. The pooled standard deviation is the square root of the average of the variances. The relative error is the differences between our value and the reported value divided by the reported value. Optical map production is very rapid because of the combination of restriction fragment ordering in real time with fast accurate sizing techniques. Optical mapping is a powerful new technology for rapidly creating ordered restriction maps of eucaryotic chromosomes or YACs, without the need for analytical electrophoresis, cloned libraries, probes, or PCR primers. Incremental technical improvements should enable the rapid high resolution mapping of mammalian chromosomes and ordering of YACs.

Gel fixation and mechanics of DNA relation under tension and cleavage. A single large DNA molecule 200 μm long (600 kb) is a random coil in solution which can be visualized as a loosely packed ball averaging 8 μm across (Roberts, 1975). Optical mapping begins with stretching out such a DNA molecule and fixing it in place to inhibit rapid relation, prior to imaging by light microscopy. The fixed molecule must lie within a shallow plane of focus for successful imaging. Elongated molecules in a gel behave mechanically like a stretched spring (Schwartz, Koval, 1989): fixed molecules are under tension which is released during coil relaxation to a random conformation. However, excess fixation is undesirable for optical mapping, since restriction cleavage sites must relax to be detected and imaged as growing gaps.

Zimm (Zimm, 1991) has modeled DNA molecules embedded in agarose gel, during electrophoresis, as a series of connected pools of coil segments under tension with each other, and calculates that the force (fi) associated with the free energy change of shuttling coil segments between pools is given by fi=3kT/(2nib)((a2/nib2)−1)+(kT/b)lnC, (Chumakov, Nature 359,380 1992) where k is the Boltzmann constant, a is the gel pore diameter, ni is the number of associated coil segments, b is the coil segment length, T is the temperature and C is a constant relating to coil segment structure. This result shows that the tension developed between pools is inversely related to the number of segments contained with a pore volume (Eq.1). It follows that a stretched our, elongated molecule is under more tension than a compact, relaxed one.

Large DNA molecules can be stretched out in molten agarose by flow forces and then rapidly fixed in place by agarose gelation, without application of electrical fields. Yeast chromosomal DNA (yeast strain AB972) was resolved by pulsed electrophoresis (D. C. Schwartz and C. R. Cantor, Cell 37,67 (1984)) using 1.00% Seakem low melting agarose (FMC), ½ TBE(42.5 mM Trizma base, 44.5 mM boric acid, 1.25 mM disodium EDTA). Cut gel bands were repeatedly equilibrated in TE (10 mM Tris-Cl, 1 mM EDTA, pH8.0). The gel embedded, purified chromosomes were then equilibrated overnight at 4° C. in magnesium-free restriction buffer containing 0.1 mg/ml acetylated bovine serum albumin, 1% β-mercaptoethanol, 0.1% Triton X-100 (Boehringer Manheim, membrane quality), and 0.2 ug/ml 4', 6-diamino-2 phenylindole dihydrochloride (DAPI) with slow shaking. Equilibrated samples ranging in volume from 50 to 100 ul were melted at 72° C. for 5 minutes, and then cooled to 37° C. Approximately 0.3–0.5 ul of enzyme (2 to 14 units/μl) was spread on a slide. Enzyme reaction temperatures were as recommended by manufacturers. β-mercaptoethanol was added to discourage photolysis M. Yanagida et al. in *Applications of Fluorescence in the Biomedical Sciences*, D. L. Taylor et al., Eds. (Alan R. Liss, New York, 1986), pp. 321–345, and was tested at this concentration for any deleterious effects on digestion using electrophoresis. A 7 μl volume of the melted sample was typically pipetted (slowly) using a wide bore pipette tip onto an 18×18 mm cover glass and rapidly deposited onto a slide. Timing and quenching of the gel is critical for controlling elongation. The reaction chamber was then sealed with mineral oil to avoid evaporation, and the agarose was allowed to gel for at least 30 minutes at 4° C., prior to diffusion of 50 mM MgCl2 through an open space. For chromosome I(240 kb) and III (345 kb), slides were in a cold desiccator (4°) prior to casting to hasten gelling avoiding premature molecular relaxation. For the larger chromosomes, which relax more slowly, slides were kept at room temperature. The slide was placed on a temperature controlled microscope stage at 37° C. (except CspI, 30° C.). Experimentally, the kinetics of gelation are controlled by temperature, and optimization of the annealing conditions. For our analysis, DNA coils must be critically stretched: too much and molecule becomes difficult to image; too little, and there is insufficient tension to reveal cut sites. Yeast chromosomal DNA (yeast strain AB972) was resolved by pulsed electrophoresis (D. C. Schwartz and C. R. Cantor, Cell 37,67 (1984)) using 1.00% Seakem low melting agarose (FMC), ½× TBE(42.5 mM Trizma base, 44.5 mM boric acid, 1.25 mM disodium EDTA). Cut gel bands were repeatedly equilibrated in TE (10 mM Tris-Cl, 1 mM EDTA, pH8.0). The gel embedded, purified chromosomes were then equilibrated overnight at 4° C. in magnesium-free restriction buffer containing 0.1 mg/ml acetylated bovine serum albumin, 1% β-mercaptoethanol, 0.1% Triton X-100 (Boehringer Manheim, membrane quality), and 0.2 ug/ml 4', 6-diamino-2 phenylindole dihydrochloride (DAPI) with slow shaking. Equilibrated samples ranging in volume from 50 to 100 ul were melted at 72° C. for 5 minutes, and then cooled to 37° C. Approximately 0.3–0.5 ul of enzyme (2 to 14 units/μl) was spread on a slide. Enzyme reaction temperatures were as recommended by manufacturers. β-mercaptoethanol was added to discourage photolysis M. Yanagida et al. in *Applications of Fluorescence in the Biomedical Sciences*, D. L. Taylor et al., Eds. (Alan R. Liss, New York, 1986), pp. 321–345, and was tested at this concentration for any deleterious effects on digestion using electrophoresis. A 7 μl volume of the melted sample was typically pipetted (slowly) using a wide bore pipette tip onto an 18×18 mm cover glass and rapidly deposited onto a slide. Timing and quenching of the gel is critical for controlling elongation. The reaction chamber was then sealed with mineral oil to avoid evaporation, and the agarose was allowed to gel for at least 30 minutes at 4° C., prior to diffusion of 50 mM MgCl2 through an open space. For chromosome I(240 kb) and III (345 kb), slides were in a cold desiccator (4°) prior to casting to hasten gelling avoiding premature molecular relaxation. For the larger chromosomes, which relax more slowly, slides were kept at room temperature. The slide was placed on a temperature controlled microscope stage at 37° C. (except CspI, 30° C.). Excessively stretched molecules present too little fluorochrome per imaging pixel, so that measured molecular intensities approach background values. Additionally, the fixation process has to be gentle enough to permit some coil slippage to reveal cut sites. Taking these and other considerations into account, our fixation conditions were optimized to produce molecules spanning approximately 20% of their curvilinear contour lengths.

How DNA molecules are entrapped by agarose gelation is not known. Imaged, stretched molecules show bright round pools of coil at their ends, evidence of chain relaxation (FIGS. 4A through 5J). The pool sizes range from 1–3 μm. Segmental pools are also observed to form internally, and then disappear, as local pockets of coil tension equilibrate with each other. As a DNA molecule relaxes within the train of contiguous gel pores it spans, the segmental density increases, and segments can even be seen to spill over into neighboring pore spaces. The detailed relaxation mechanism is a complex one (de Gennes, et al., Scaling Concepts in Polymer Physics, Cornell University Press, 1979). Gaps appear because a molecule experiences an effective tension since the configurational entropy of the elongated polymer is lower than that of the relaxed state. On a simple descriptive level, the process can be compared to watching the relaxation of a stretched-out thick rubber band encased in a tight tube, with holes in the sides. Cleavage accelerates relaxation by creating new ends within a molecule, and possibly also by causing a mechanical perturbation that releases trapped fragments from local energy minima.

A high numerical aperture microscope objective can produce bright, high contrast images of stained DNA molecules, but with a very shallow depth of focus. Experimentally, for a long molecules to be in focus, it must lie within a plane approximately 0.2 μm thick. Our method of gel fixation reproducibly allows visualization of molecules that are within this 0.2 micron tolerance as measured optically. This remarkable degree of optical flatness results from a laminar, parabolic fluid flow pattern generated between the glass surfaces, prior to gelation. Furthermore, dissolved agarose and DNA molecules may potentiate this effect by facilitating laminar flow, while preventing onset of turbulence (Atkins, 1992).

Finally, gel fixation of large DNA molecules is convenient enough to be broadly applicable to other systems, especially when biochemical reactions can be coupled to visualizable events.

Restriction Digestion of Single Molecules. Optical mapping detects restriction enzyme cleavage sites as gaps that appear in a fixed molecule as fragments relax to a more random conformation (FIGS. 13A–13E and 15A–15C). Since the rates of enzymatic cleavage by different restriction enzymes are variable (Wells, et al.,Genetics 127,681, 1981), careful adjustment of the timing is critical. Cleavage should occur only after molecular fixation is complete because premature reactions disrupt attempts to phase fragments. This timing problem was solved by premixing the agarose-DNA solution with restriction enzyme, at 37° C., and triggering the reaction by diffusing magnesium ions into the viewing field, without disturbing the gel. Yeast chromosomal DNA (yeast strain AB972) was resolved by pulsed electrophoresis (D. C. Schwartz and C. R. Cantor, Cell 37,67 (1984)) using 1.00% Seakem low melting agarose (FMC), ½× TBE(42.5 mM Trizma base, 44.5 mM boric acid, 1.25 mM disodium EDTA). Cut gel bands were repeatedly equilibrated in TE (10 mM Tris-Cl, 1 mM EDTA, pH8.0). The gel embedded, purified chromosomes were then equilibrated overnight at 4° C. in magnesium-free restriction buffer containing 0.1 mg/ml acetylated bovine serum albumin, 1% β-mercaptoethanol, 0.1% Triton X-100 (Boehringer Manheim, membrane quality), and 0.2 ug/ml 4', 6-diamino-2 phenylindole dihydrochloride (DAPI) with slow shaking. Equilibrated samples ranging in volume from 50 to 100 ul were melted at 72° C. for 5 minutes, and then cooled to 37° C. Approximately 0.3–0.5 ul of enzyme (2 to 14 units/µl) was spread on a slide. Enzyme reaction temperatures were as recommended by manufacturers. β-mercaptoethanol was added to discourage photolysis M. Yanagida et al. in *Applications of Fluorescence in the Biomedical Sciences*, D. L. Taylor et al., Eds. (Alan R. Liss, New York, 1986), pp. 321–345. and was tested at this concentration for any deleterious effects on digestion using electrophoresis. A 7 µl volume of the melted sample was typically pipetted (slowly) using a wide bore pipette tip onto an 18×18 mm cover glass and rapidly deposited onto a slide. Timing and quenching of the gel is critical for controlling elongation. The reaction chamber was then sealed with mineral oil to avoid evaporation, and the agarose was allowed to gel for at least 30 minutes at 4° C., prior to diffusion of 50 mM MgCl2 through an open space. For chromosome I(240 kb) and III (345 kb), slides were in a cold desiccator (4°) prior to casting to hasten gelling avoiding premature molecular relaxation. For the larger chromosomes, which relax more slowly, slides were kept at room temperature. The slide was placed on a temperature controlled microscope stage at 37° C. (except CspI, 30° C.). Aside from gaps, cleavage is also signaled by the appearance of bright condensed pools or "balls" of DNA on the fragment ends at the cut site. These balls form shortly after cleavage and result from coil relaxation which is favored at ends (FIGS. 13A–13F and 15A–15C). This pooling of segments is useful in map making because it helps to differentiate out-of-focus segments, that might appear as gaps, from actual cuts. Cleavage is scored more reliably by both the appearance of growing gaps and enlarging bright pools of segments at the cut site.

Map Construction—Fragment Number Determination. Large scale restriction maps have been constructed primarily from electrophoretically derived data. A new set of approaches has been developed to size and order fragments on samples that can consist of single DNA molecules, using microscope based techniques. The first step is to determine the number of cleavage sites within a molecule. The cut sites within a molecule tend to appear at irregular times after Mg2+ addition. All possible cleavage sites do not appear simultaneously; instead, cuts usually appear within 5 minutes of each other, under the conditions described here. The extent of digestion depends on a number of factors including both the fragment number and size. Digestion results obtained by optical mapping for a selected set of Not I digested yeast chromosomes are displayed in FIGS. 7A–7D. Fortunately, published Not I restriction enzyme maps are available for all *S. cerevisiae* chromosomes (Link, 1991), enabling reliable benchmarking of the optical mapping methodology.

A typical mounted sample contains approximately 3–5 molecules within a single viewing field and overall, roughly 50–95% of them show evidence of one or more cuts by the criteria described here. The histograms in FIGS. 7A–7D show that the overall number of cut sites exceeding published results is quite low. The cutting frequency results (FIG. 7B) for chromosome V digested with Not I show that the number of fully cut molecules is approximately half that of all singly cut molecules: the value corresponding to complete digestion is caculated by assuming that an equal distribution of identically sized chromosome V and VIII DNA molecules are present in the mounted sample. The Not I restriction maps for these chromosomes reveal that chromosome V has 3 cut sites, while VIII has only 2. Chromosome XI cutting frequency data (FIG. 7C) is different; 25% of all cut molecules are seen to be fully digested (two cutting sites). An explanation for the apparently lower frequency is that this chromosome produces a 30 kb sized Not I fragment that is more difficult to detect optically than larger fragments. This result is not surprising considering that tension across a cut is probably fragment size dependent, so that smaller, elongated fragments apply less tension. Furthermore, since coil tension across a cut site is required for its identification, additional cuts will produce fragments that ultimately relax to reduce the overall molecular tension and impede the observation of further cuts. Finally, very large, 1 megabase sized molecules have been spread, such as chromosome XIII and XVI, and these data (FIG. 7D) show that roughly half of the molecules are digested to completion (one cut) in mounts with observable cutting activity.

The maximum number of cuts determined by histogram analysis is the bin containing the largest number of cut sites whose molecules can be properly averaged by intensity and length measurements for size.

Figure 8A:
Figure 8B:
Figure 8C:
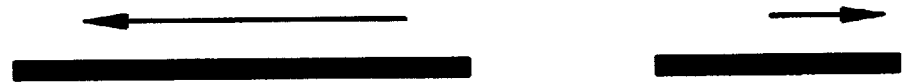
Figure 8D:
Figure 8E:
Figure 8F:
Figure 8G:
Figure 8H:

Influence of coil relaxation on detection of cuts. Aside from cases involving small fragments, incomplete digestion is seen in all the histograms in FIGS. 7A–7D. While potential cases range from photo irradiation artifacts to interactions imposed by the current design of the microscope chamber, partial digestion observed here is attributable mostly to incomplete coil relaxation at a given cut site, due to relaxation modes that fail to produce a gap or distinct ball. A variety of different relaxation modes are observed in actual practice, some of which are sketched in FIGS. 8A–8H. Relaxation modes can both facilitate (FIG. 8D) and hinder cut detection (FIG. 8D). Application of electric or flow fields might be used to trigger relaxation at such sites and permit their detection. Parallel electrophoresis experiments show essentially complete digestion under similar experimental conditions (Hernandez).

Interestingly, the data for chromosome I show almost complete digestion (95%; see FIG. 7A). Images of chromosome I under digestion (FIG. 13A) reveal that after the expected single cut is observed, only the cut site ends relax and bright pools of segments accumulate at the ends (20 molecules), as interpreted in FIGS. 8B, 8C and 8D, while the remaining ends appear to be fixed in place. Bright pools of relaxed coil segments accumulate at the ends of gel-fixed DNA molecules, as noted above.

Conceivably, the ends of chromosome I embedded in agarose are behaving as a sort of molecular rivet (FIG. 9), reacting to the tension developed between it and the intervening molecular segments to provide ideal mechanical conditions for cut detection. It seems likely that short-range interactions will predominate so that the amount of relaxed coil present at the ends of elongated molecules will not vary much with molecular mass above some threshold in size. Consequently, a relatively short molecule, such as chromosome I, will contain a greater proportion of relaxed coil segments at its end than longer ones, such as chromosomes XIII and XVI.

Fragment Sizing By Relative Intensity. The second step is to size the resulting restriction fragments. For this purpose two complementary approaches can be used, one based on relative fragment fluorescence intensity and the second on apparent relative length measurements. However, neither approach provides absolute values, but each can be standardized readily. Fortunately, the gel fixation technique described above produces a natural substrate for intensity measurements since an entire molecule can be brought into focus. Gel fixation is able to flatten molecules spanning as much as 250 µm. Segments of molecules that are out of focus cannot be used for intensity measurements because their intensities are not proportional to mass in any simple way. A relevant observation here is that when an elongated molecules substantially relaxes, most of its mass moves out of focus, as expected, since the hydrodynamic diameter of a fully relaxed 700 kb DNA molecule in fluid is 8 µm while the depth of focus used for imaging molecules under the microscope is approximately 0.2 µm.

Figure 10A:
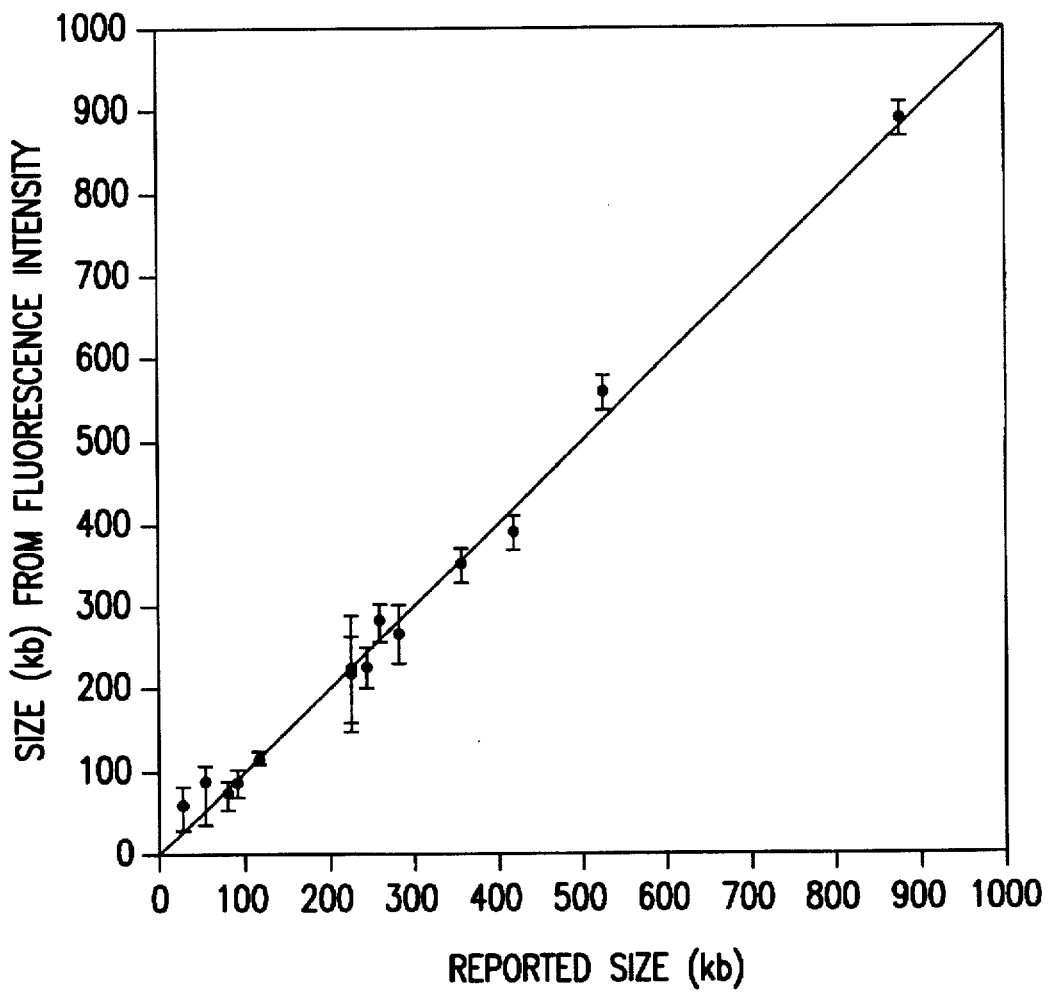
Figure 10B:
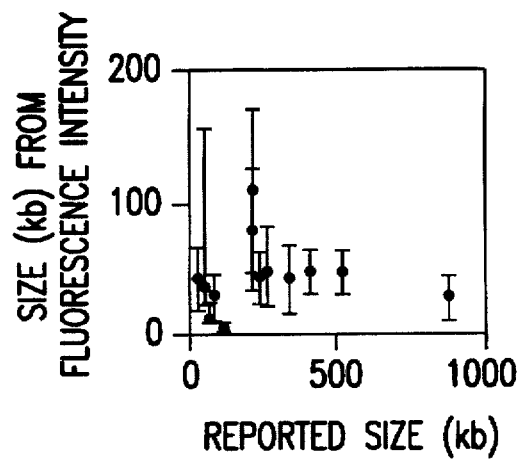
Figure 10C:
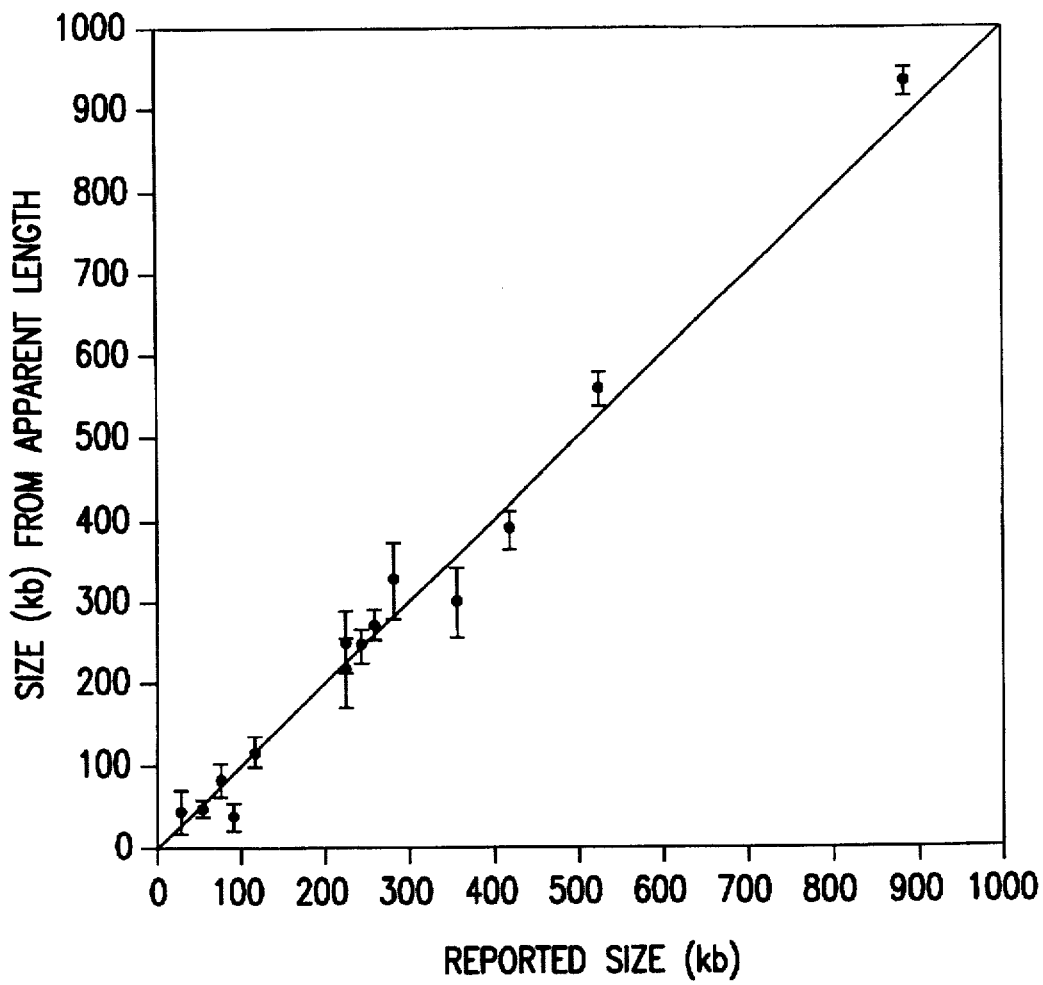
Figure 10D:
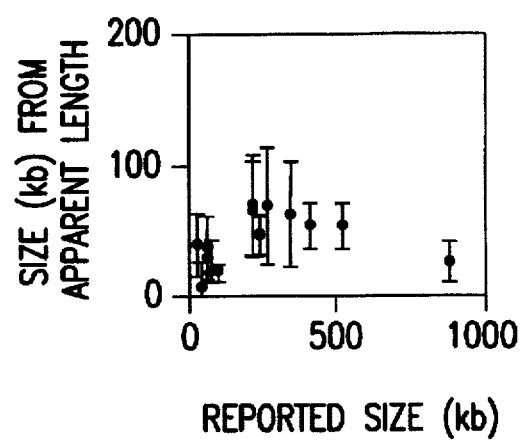

The absolute fluorescence intensity of a DNA fragment in the microscope is determined by many variables, such as the camera gain control and lamp brightness, and therefore is not a desirable quantity to measure. By calculating the relative intensity of two fragments (from the same parental molecule), one of the fragments can serve as an internal intensity reference for the other. Relative intensities are converted to kb by multiplying by the know or independently determined chromosome size. Length and relative fluorescence intensity were calculated to 16-bit precision using a modified version of NIH Image for Macintosh by Wayne Rasband, available upon request from the authors (e-mail huff @ mcclb0.med.nyu.edu). Further details are available (manuscript in preparation). Briefly, the original unprocessed image was displayed in an enlarged format and an overlay image was prepared by manually tracing the DNA. The length map was made directly from this overlay. For intensity calculations, the 13-bit raw data image was smoothed and the overlay image was dilated five times to cover all foreground pixels. For each pixel marked on the overlay, a synthetic background value was calculated as the weighted average of surrounding pixels, with a weight that decreased with distance, but was zero for all marked pixels. These values are intended to approximate those which would have been measured had the DNA been absent. The intensity of a particular DNA fragment was the sum of all pixels of the fragment minus the matching background pixels. The area of the fragment was the original overlay dilated twice. This process was repeated for each frame of raw data which had an overlay image, excluding those with poor focus. Intensity results Were averaged for five images following a cut, and the relative sizes of the two fragments were calculated as $x/(x+y)$ and $y/(x+y)$. If fragment y later cuts into u and v, then $(y/(x+y))(u/(u+v))$ is used for the size of u. The resulting numbers constitute a single sample for the purposes of subsequent analysis. The optical contour maximization technique can be used to size samples containing a small number of molecules (Guo, Nature 359,783, 1992). FIGS. 10A–10B show intensity values for a series of yeast chromosome Not I restriction fragments measured optically and plotted against published values derived from electrophoresis based measurements (Link, Genetics, 127, 681, 1991). Points close to the diagonal line are in good agreement. Disregarding the chromosome V and VIII results, which were based on low precision (8-bit) intensity data, and disregarding the two short fragments less than 60 kb, the pooled standard deviation is 36 kb (FIGS. 10B) and the average of the coefficients of variation is 16%, comparable to routine pulsed electrophoresis size determinations. The correlation with published results is excellent: the average of the relative errors is 5% whereas the published errors average 4% (Link, Genetics, 127, 681, 1991). The samples were averaged and the 90% confidence interval on the mean was calculated using the t distribution with n–1 d.f. and the sample standard deviation. This calculation is valid if the data represent random samples from a normal distribution. There is a 90% chance that the population mean falls within the confidence interval. For chromosome I, the reported confidence interval was found by taking the lower bound from the short fragments and the upper bound from the long fragments. The 90% confidence interval for the population standard deviation (FIGS. 10B and 10D) was calculated using the sample standard deviation, the number of samples, and the chi-square distribution with n–1 d.f. The midpoint of this interval was used to estimate the population standard deviation. The coefficient of variation (CV) is the estimated population standard deviation divided by the sample mean. The pooled standard deviation is the square root of the average of the variances. The relative error is the differences between our value and the reported value divided by the reported value. Due in part to the intensity normalization procedure, the precision becomes lower for very small fragments, and size agreement is poor for the 30 and 55 kb measurements. Fluorescence intensity measurements size these fragments at almost twice the established values as described below. Changes in the algorithm for correcting the backgrounds of these measurements and the data collection process should improve the precision significantly.

Figure 11A:
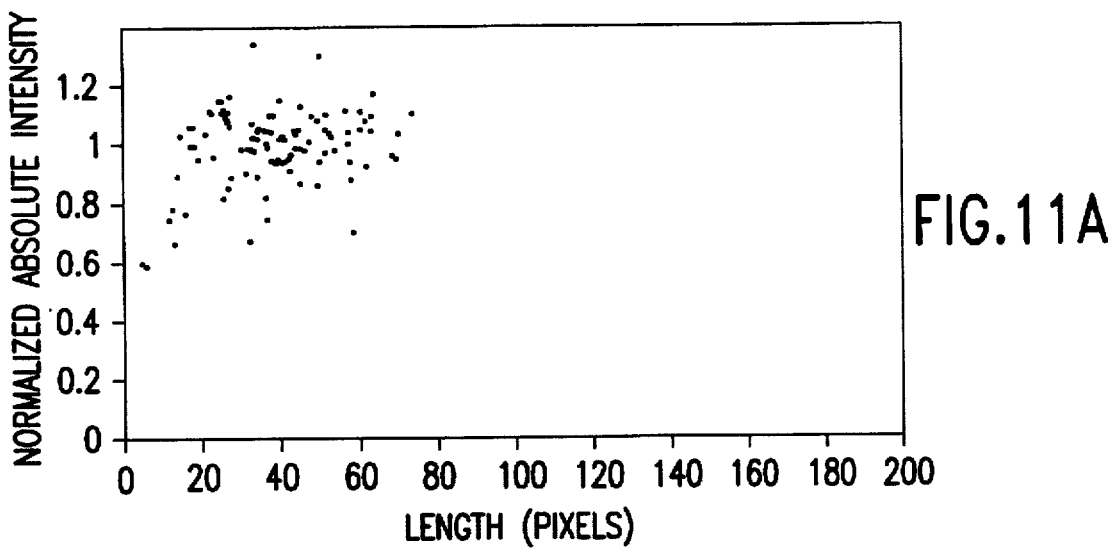
Figure 11B:
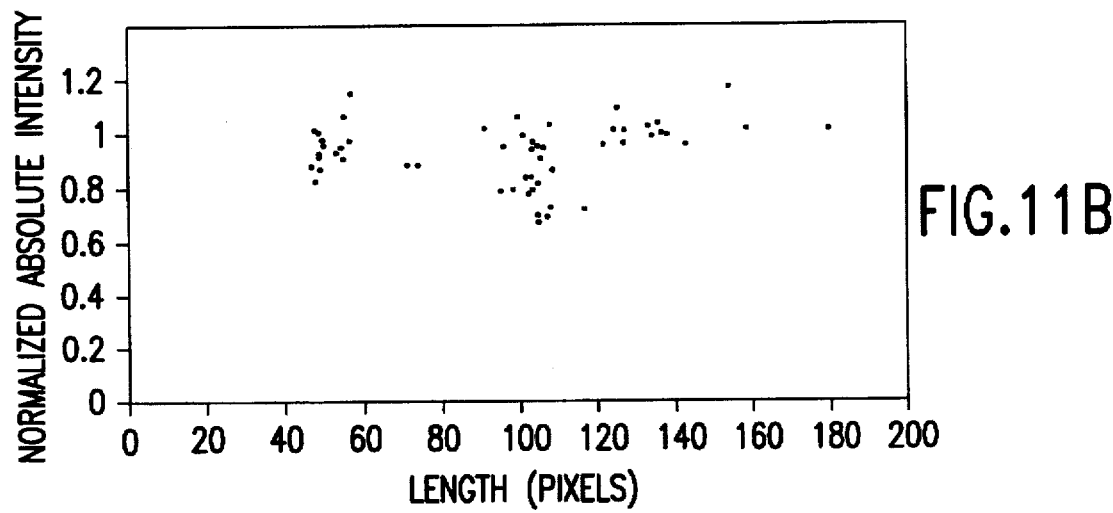
Figure 11C:
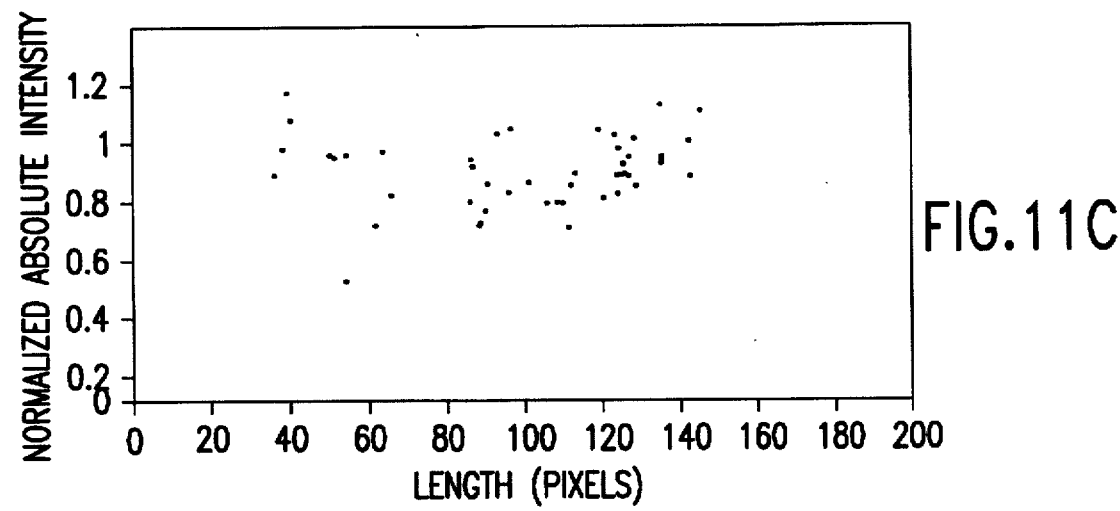
Figure 13A:
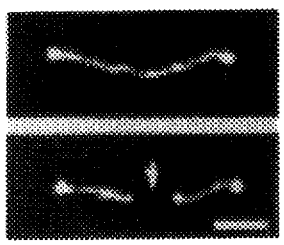
Figure 13B:
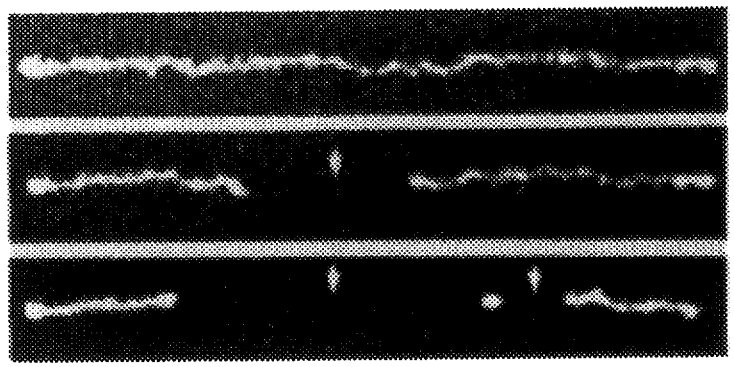
Figure 13C:
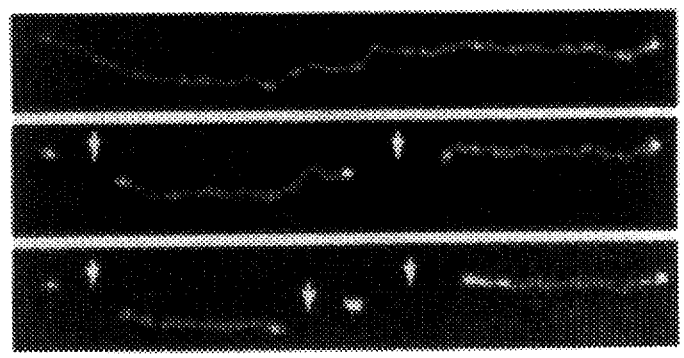
Figure 13D:
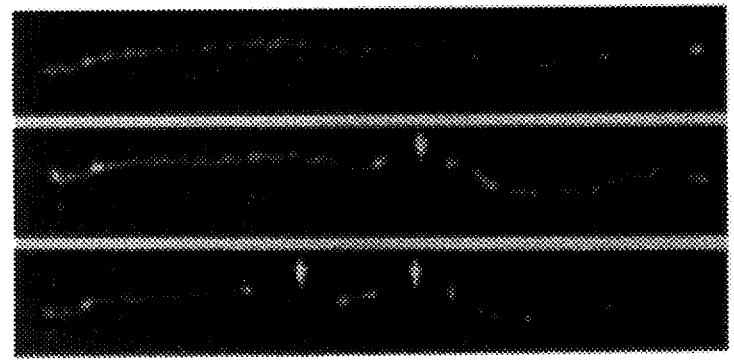
Figure 13E:
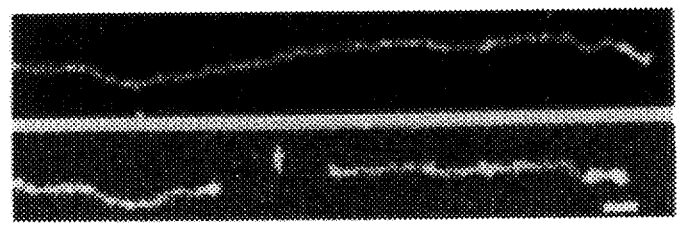
Figure 13F:
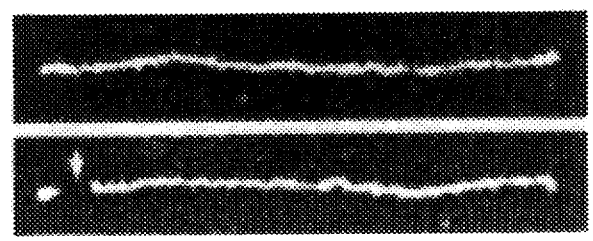

One test of the validity of relative fluorescence intensity measurements is to monitor the constancy of fragment intensities over a usable range of molecular relaxation conditions. This requirement is most critically tested when restriction fragments differ greatly in size. FIG. 11 shows the results of absolute intensities versus molecular length measurements for three typical sizes. These results show that intensities remain relatively constant over a wide size range despite a 3–4 fold change in measured molecular length. This beneficial effect is attributed in part to the mild fixation conditions, so that Brownian motion can dither the elongated coil along the z-axis; this motion is clearly observed on the live video monitor as digestion proceeds. By averaging frames over a 1 second interval most of the DNA is observed as it moves through the focal plane and within the gel pores.

Fragment Sizing by Relative Apparent Lengths. The physical basis of apparent length measurement is simple: each gel-embedded restriction fragment is assumed to have equal coil density, on the average. That is, each fragment has the same change to be stretched more or less, so a length average created over a number of mounts provides a good measure of relative size. Again, relative apparent lengths are converted to kb by multiplying by the chromosome size. Length and relative fluorescence intensity were calculated to 16-bit precision using a modified version of NIH Image for Macintosh by Wayne Rasband, available upon request from the authors (e-mail huff @ mcclb0.med.nyu.edu). Further details are available (manuscript in preparation). Briefly, the original unprocessed image was displayed in an enlarged format and an overlay image was prepared by manually tracing the DNA. The length map was made directly from this overlay. For intensity calculations, the 13-bit raw data image was smoothed and the overlay image was dilated five times to cover all foreground pixels. For each pixel marked on the overlay, a synthetic background value was calculated as the weighted average of surrounding pixels, with a weight that decreased with distance, but was zero for all marked pixels. These values are intended to approximate those which would have been measured had the DNA been absent. The intensity of a particular DNA fragment was the sum of all pixels of the fragment minus the matching background pixels. The area of the fragment was the original overlay dilated twice. This process was repeated for each frame of raw data which had an overlay image, excluding those with poor focus. Intensity results were averaged for five images following a cut, and the relative sizes of the two fragments were calculated as $x/(x+y)$ and $y/(x+y)$. If fragment y later cuts into u and v, then $(y/(x+y))(u/(u+v))$ is used for the size of u. The resulting numbers constitute a single sample for the purposes of subsequent analysis. Then, the apparent lengths of restriction fragments are converted, obtaining good accuracy from as few as 4 molecules. The samples were averaged and the 90% confidence interval on the mean was calculated using the t distribution with n−1 d.f. and the sample standard deviation. This calculation is valid if the data represent random samples from a normal distribution. There is a 90% chance that the population mean falls within the confidence interval. For chromosome I, the reported confidence interval was found by taking the lower bound from the short fragments and the upper bound from the long fragments. The 90% confidence interval for the population standard deviation (FIGS. 10B and 10D) was calculated using the sample standard deviation, the number of samples, and the chi-square distribution with n−1 d.f. The midpoint of this interval was used to estimate the population standard deviation. The coefficient of variation (CV) is the estimated population standard deviation divided by the sample mean. The pooled standard deviation is the square root of the average of the variances. The relative error is the differences between our value and the reported value divided by the reported value. Relative determinations of apparent length were verified against the same set of restriction fragments as in the fluorescence intensity measurements, and these results (FIG. 10C) show a similar average relative error of 16% (excluding the 30 and 90 kb fragments). The pooled standard deviation was 47 kb (FIG. 10D), the average of the coefficients of variation was 29%.

Apparent molecular length measurements are more robust than intensity measurements, but are less precise, and consequently require additional measurements to achieve an equivalent degree of accuracy. But good length measurements can be obtained from slightly out-of-focus fragments, whereas blurry, out of focus images will confound intensity based measurements. Size determination of small fragments by length were better than intensity. The 30 kb fragment was sized at 44 kb by length vs. 70 kb by intensity, and the 55 kb fragment was sized at 49 kb vs. 88 kb. Given the limited sample number inherent to optical mapping, having two sizing methods for cross-checking results is extremely important for successful map making.

Map Construction Based on Length and Intensity Measurements. FIG. 12 illustrates three types of ordered restriction maps produced by optical mapping compared with (Link, Genetics 127, 681, 1991). The bars shown correspond to sizing analysis results of the Not I restriction fragment as plotted in FIGS. 10A–10D. FIGS. 13A–13F shows selected processed fluorescence micrographs of different yeast chromosomal DNA molecules digested with Not I. Yeast chromosomal DNA (yeast strain AB972) was resolved by pulsed electrophoresis (D. C. Schwartz and C. R. Cantor, *Cell* 37:67 (1984)) using 1.00% Seakem low melting agarose (FMC), ½× TBE(42.5 mM Trizma base, 44.5 mM boric acid, 1.25 mM disodium EDTA). Cut gel bands were repeatedly equilibrated in TE (10 mM Tris-Cl, 1 mM EDTA, pH8.0). The gel embedded, purified chromosomes were then equilibrated overnight at 4° C. in magnesium-free restriction buffer containing 0.1 mg/ml acetylated bovine serum albumin, 1% β-mercaptoethanol, 0.1% Triton X-100 (Boehringer Manheim, membrane quality), and 0.2 ug/ml 4′, 6-diamino-2 phenylindole dihydrochloride (DAPI) with slow shaking. Equilibrated samples ranging in volume from 50 to 100 ul were melted at 72° C. for 5 minutes, and then cooled to 37° C. Approximately 0.3–0.5 ul of enzyme (2 to 14 units/μl) was spread on a slide. Enzyme reaction temperatures were as recommended by manufacturers. β-mercaptoethanol was added to discourage photolysis (M. Yanagida et al. in *Applications of Fluorescence in the Biomedical Sciences*, D. L. Taylor et al., Eds. (Alan R. Liss, New York, 1986), pp. 321–345.) and was tested at this concentration for any deleterious effects on digestion using electrophoresis. A 7 μl volume of the melted sample was typically pipetted (slowly) using a wide bore pipette tip onto an 18×18 mm cover glass and rapidly deposited onto a slide. Timing and quenching of the gel is critical for controlling elongation. The reaction chamber was then sealed with mineral oil to avoid evaporation, and the agarose was allowed to gel for at least 30 minutes at 4° C., prior to diffusion of 50 mM MgCl2 through an open space. For chromosome I(240 kb) and III (345 kb), slides were in a cold desiccator (4°) prior to casting to hasten gelling avoiding premature molecular relaxation. For the larger chromosomes, which relax more slowly, slides were kept at room temperature. The slide was placed on a temperature controlled microscope stage at 37° C. (except CspI, 30° C.). These images clearly show progressive digestion by the appearance of growing gaps in the fixed molecules. From such data fragment, order was determined from inspection of time-lapse images obtained every 20 seconds. DNA molecules were imaged using a Zeiss Axioplan or Axiovert 135 microscope equipped for epi-fluorescence (487901 filter pack for UV excitation and Blue emission) and a 100× or 63× Plan-Neofluar objective (Zeiss) coupled to Hammamatsu C2400 SIT cameras. Care was taken to adjust the camera controls to avoid saturating the digitizer at either end of the intensity range. Every 20 seconds, 32 video frames were digitized to 8 bits and integrated to give 13 bit precision by a Macintosh based Biovision image processor or a Pixel pipeline digitizer (Perceptics Corp.). A computer controlled shutter was used to limit illumination to 1.5 seconds per image giving a total of about 135 to 255 seconds for typical experiments. Neutral density filters were used to keep the illumination intensity below 100 μW measured at the objective. Control experiments showed no damage to DNA molecules under these conditions. Digitized images were recorded directly to disk and archived on tape. Since observed molecules tend to move and can sometimes be confused with other molecules, inspection of a "cutting sequence" or "cutting movie" simplifies deconvolution of molecule-molecule interactions. Agreement is excellent between the optical (length or intensity) and the electrophoresis based maps. The third type of restriction maps ("Com", FIGS. 7A–7D) results from combining length and intensity derived data: data from small restriction fragments (<60 kb) were sized by length, while intensity measurements provide the balance of fragment sizes needed to complete the maps.

Figure 14:
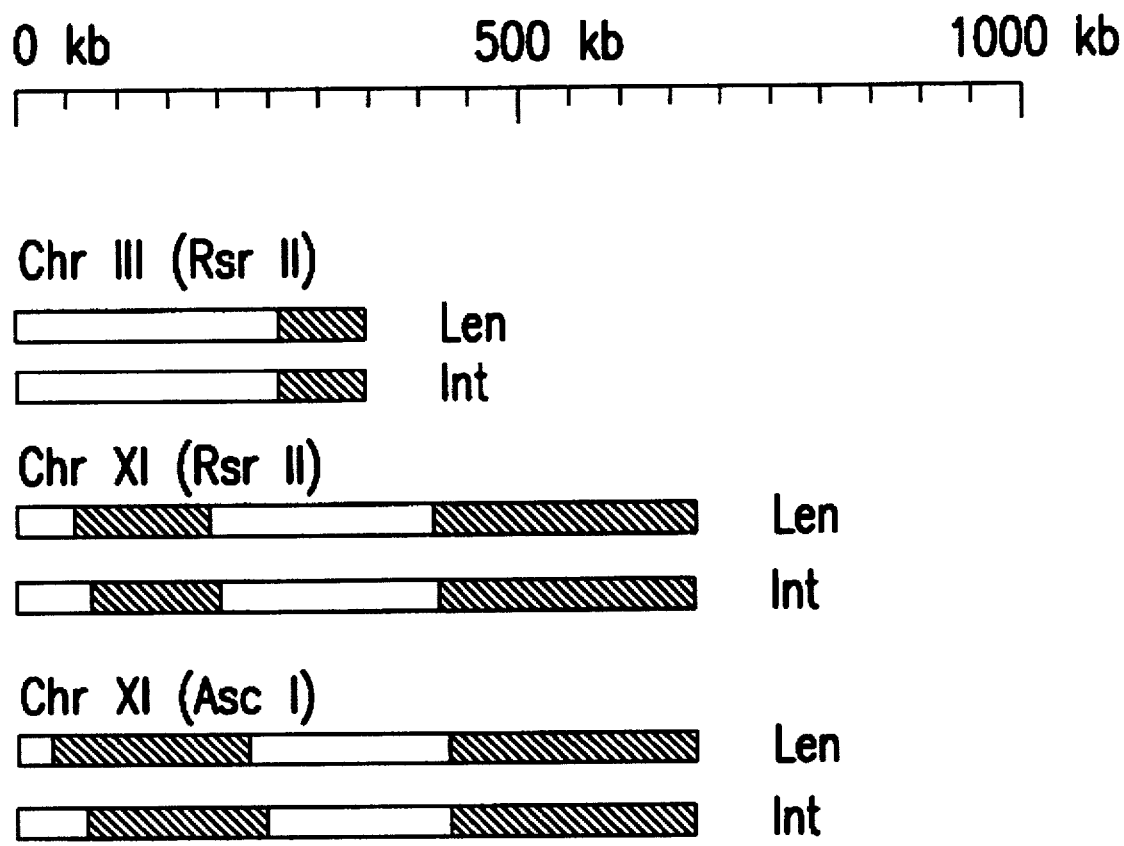
Figure 15A:
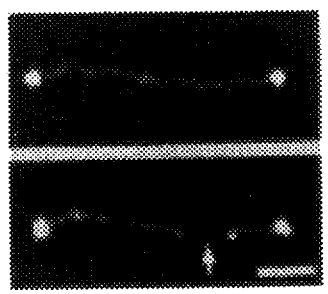
Figure 15B:
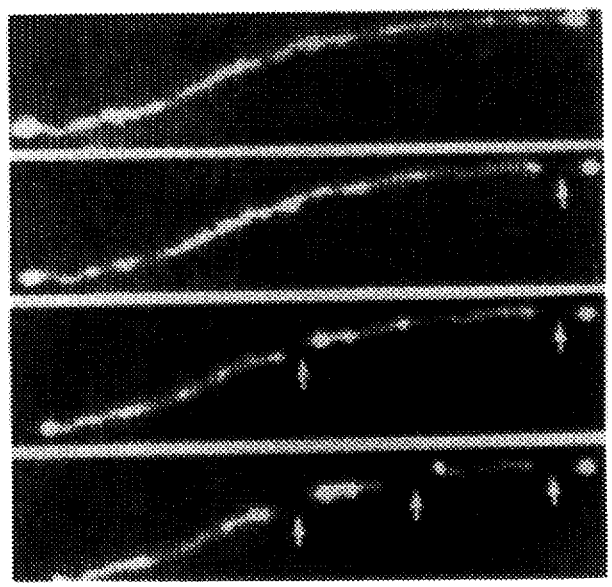
Figure 15C:
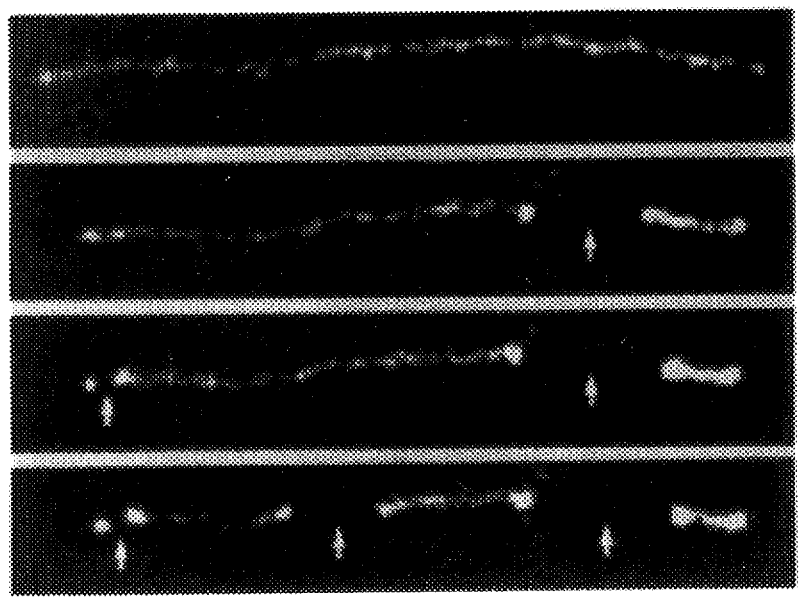

FIG. 14 shows the ordered restriction maps created from Rsr II digestion of chromosome III and XI and Asc I digestion of chromosome XI by optical mapping, while FIG. 15 shows the corresponding fluorescence micrographs of typical digests. Relative apparent length results, using the pooled population standard deviation of 47 kb to calculate confidence intervals. Chromosome, enzyme, mean +/–90% confidence kb (number of samples). Ch. III Rsr II 264 +/–27(8), 86 +/–27(8). Ch. XI Asc I 42 +/–55(2), 195 +/–55(2), 242 +/–55(2). Ch. XI Rsr II 67 +/–45(3), 127 +/–45(3), 221 +/–45(3), 260 +/–45(3). Relative fluorescence intensity results, using the pooled population standard deviation of 36 kb to calculate confidence intervals. Ch. III Rsr II 256 +/–21(8). Ch. XI Asc I 80 +/–42(2), 177 +/–42(2), 181 +/–42(2), 237 +/–42(2). Ch. XI Rsr II 84 +/–34(3), 125 +/–34(3), 226 +/–34(3), 240 +/–34(3). There are no published maps available for independent verification of these results. These maps are constructed by first determining the maximum number of cleavage sites from cutting frequency data (similar to FIGS. 7A–7D). Fragments from fully cut molecules are then sized by length and intensity and sorted into bins for averaging. Relative fluorescence intensity measurements are used to sort length measured fragments. Obviously, adjacent fragments must go into adjacent bins for averaging. Distinctive patterns in a digest, such as a very large fragment lying next to a very small one, facilitate accurate sorting. Data from partial digests was also used to confirm the maps. Data from partial digests was used to confirm the map constructed from fully cut molecules by calculating the expected partial fragment lengths and comparing these to the observed data.

A new set of analytical approaches to physical mapping of very long molecules, such as DNA molecules, is thus provided according to the present invention, that is simple and intrinsically very rapid. A nearly real time mapping procedure for chromosomes of yeast has been implemented, but this is far from the ultimate capability of the methodology. Since most traditional tools of genomic analysis are bypassed, including cloning, electrophoresis, Southern analysis and PCR, additional speed increases in optical mapping are not predicated on advances in robotics or automation (Chumakov, *Nature* 359:380, 1992). Simple engineering advances in chamber design, sample handling, image analysis and informatics should make available a high throughput methodology capable of rapidly mapping entire genomes and, more importantly, extending knowledge of sequence information to populations of individuals rather than prototypes of each organism (Cavalli-Sforza, *Am. J. Hum. Genet* 46:649, 1990).

EXAMPLE 14

Optical Mapping of Lambda Bacteriophage Clones Using Restriction Endonucleases In the Example presented herein, the size resolution of the optical mapping technique is greatly improved upon by the imaging individual DNA molecules elongated and fixed onto derivatized glass surfaces. Averaged fluorescence intensity and apparent length measurements accurately determined the mass of restriction fragments 800 base pairs long. Specifically, such a solid surface bsed optical mapping technique has been used to create ordered restriction maps for lambda clones derived from the mouse Pygmy locus.

14.1 MATERIALS AND METHODS

Preparation of polylysine coated glass surfaces. Cover glasses (182 mm, Fisher Scientific) were cleaned by boiling in 5M hydrochloric acid for 2–3 hours, rinsed thoroughly with high purity water, air dried and then incubated overnight in filtered, poly-D-lysine (MW=350, 500, Sigma) solutions (ranging from $1 \times 10^{-2}$ to $1 \times 10^{-8}$ g/ml water). Autoclaved water was used for all solutions.

Microscopy and image collection. DNA molecules were imaged by a Zeiss Axiovert 35 microscope equipped for epifluorescence and a 100× Plan-Neofluar objective (Zeiss). A Hammatsu C2400 SIT camera was used to focus a cooled digital CCD camera (1032×1316 pixels) controlled by standard, commercially available software running on a Quadra 900 computer.

DNA preparation and gel electrophoresis. Analyzed clones come from a lambda FIX II library Constructed from a YAC, mapped to the mouse Pygmy locus. Cells were grown and infected with plate grown phage using standard protocols and DNA was prepared using a commercially available kit (Qiagen, Germany) with small modifications. Restriction digests were performed as per manufacturers directions and analyzed using conventional and pulsed field gel electrophoresis. Gels were stained with ethidium bromide and documented with Polaroid film and a UV transilluminator.

DNA mounting and restriction digestion. 1 µl of diluted clone DNA (5 ng/µl) was added to 1× restriction buffer (as suggested by manufacturer but without magnesium ions), 3% β-mercaptoethanol and 0.2 ng/µl ethidium homodimer. 3 to 4 µl aliquots were pipetted and spread onto slides with drilled 3 mm holes. Polylysine coated cover glasses were dried by gently wiping with lens tissue paper (Ross Tissue, Rosmarin Corp.) and placed on top of slides and sealed with a mixture of Vaseline and mineral oil. Cover glass-slide sandwiches were mounted onto the microscope stage and 5 µl amounts of restriction endonuclease (5 to 10 units) diluted in 1× restriction buffer (as suggested by manufacturers) were diffused into samples through the drilled holes and then incubated for 15 minutes at room temperature.

Characterizations of polylysine coated glass surfaces. 1 µl of lambda DNA (New England Biolabs) (5 ng/µl) was mixed with 100 µl of 1× EcoRI restriction buffer (50 mM NaCl, 100 mM Tris-HCl and 0.025% Triton X-100, pH 7.5; without magnesium ions), ethidium homodimer (0.2 ng/µl) and 5% β-mercaptoethanol. 4 µl samples were pipetted onto cleaned microscope slides (no hole) and covered with cover glasses, incubated in different poly-D-lysine solution (MW=350,500) concentration for 16 hours. 20 to 30 different cover glass locations were imaged for each concentration. The length and number of DNA molecules from different locations were averaged. The number of molecules available on per image view were calculated from the DNA concentration, sample volume and the image area. The ratios of the average number of molecules to the available molecules, present in solution, were calculated and plotted against the polylysine concentration.

Map construction. Maps were constructed from optical data using techniques described in Example 13, above, with some modifications. Briefly, the image processing steps were flat field correction, background correction, segmentation, pixel value integration, and intensity ratio calculation. The relative intensities of the fragments were calculated and the size in kb was found by multiplying by the known total size. The empirical calibration function was applied to eliminate a systematic underestimate of small fragments sizes. Fragments less than 6.5 kb were divided by 0.665. Larger fragments are adjusted to preserve the known total size.

Relative apparent lengths were calculated by magnifying the image fourfold by pixel replication and using a mouse to place a segmented line along each fragment. Fragment ends are placed at the center of the gap between fragments. The length of each fragment was the sum of the lengths of the straight line segments. The size in kb was found by dividing by the sum of all fragments and multiplying by the known total size.

The image analysis process was repeated for a number of molecules from several images taken from one sample. Molecules which showed the proper number of cuts were analyzed. The orientation of each molecule was determined from the sizes of the cloning arm fragments. This permitted averaging of many measurements with little chance of including data from one fragment in the average of a different fragment.

14.2 RESULTS

Fixing DNA molecules onto polylysine coated glass surfaces
Polylysine has long been used to fix cells to glass surfaces (Williams, Proc. Natl. Acad. Sci. U.S.A. 74:2311–2315, 1977). Extensive measurements of polylysine coated mica surfaces by refractive index measurements (Luckham and Klein, Chem. Soc., Faraday Trans. I, 80:865–878, 1984) showed that polylysine coils can be compressed onto the surface and thus alter its properties. Given the extensive history of polylysine use in cell biology, it was reasoned that polylysine coated glass would be simple to control and be biochemically compatible. The molecular weight and concentration of polylysine used for surface deriviti-zation is critical: too much and the molecules are severely fixed and biochemically inert; too little, and the elongated DNA molecules relax quickly to a random coil conformation. These are precisely the concerns successfully dealt with in the previous agarose-based optical mapping methodology.

Figure 16:
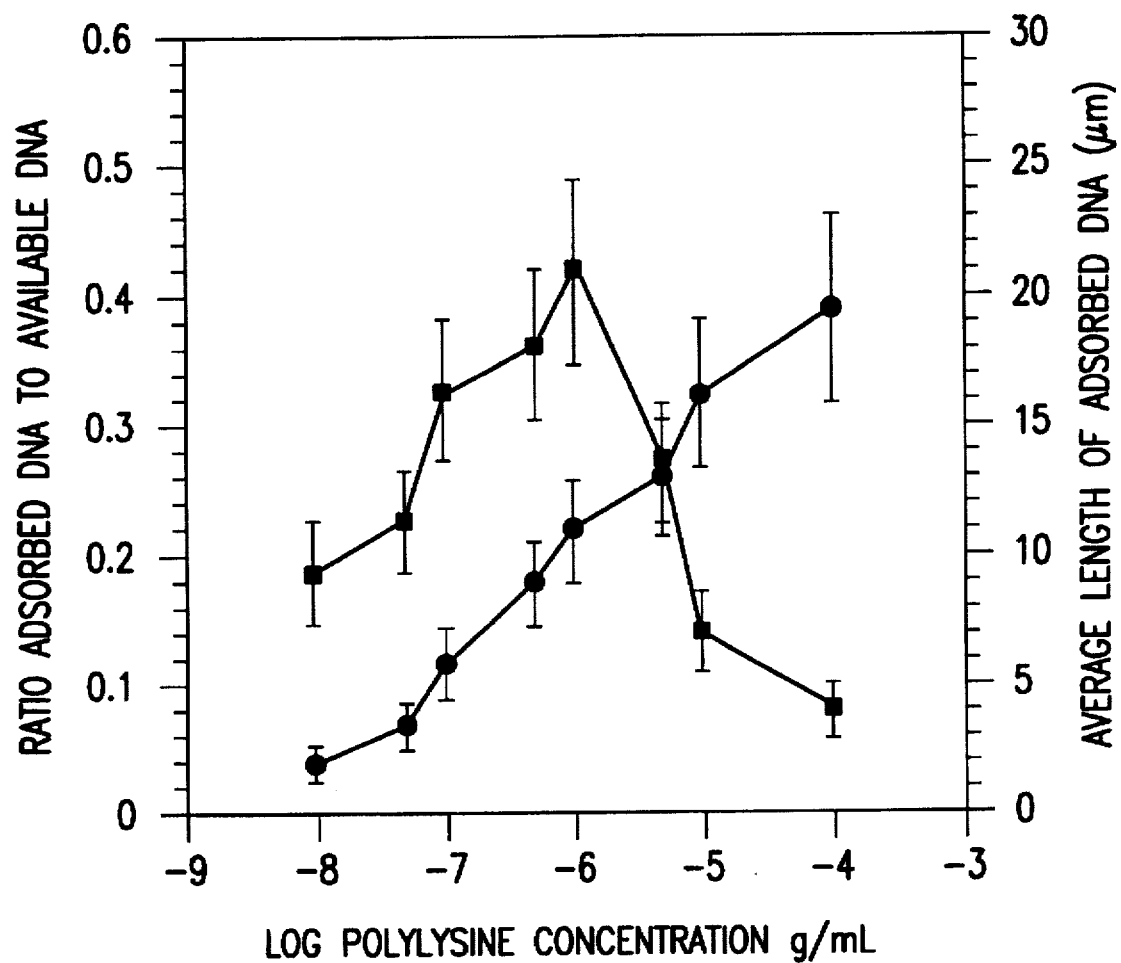

The polylysine concentration was optimized by plotting the average molecular extension and count found on the surface versus polylysine concentration. Fluorescence microscopy was used to image labeled molecules on the surface. FIG. 16 shows the results of varying polylysine concentration (MW=350,500) on the counts of lambda bacteriophage DNA molecules found on the surface, and the average molecular length. As expected, the average molecular length was small at low polylysine concentration as were the counts of molecules detected on the surface. The average molecular extension increased with polylysine concentration and peaked at $10^{-6}$ g/ml; further increase of polylysine concentration reduced the molecular extension. Predictably, the molecule count on the surface increased.

The exact mechanism of how extended DNA molecules interact with a polylysine coated surface is unknown. Since both DNA and polylysine are highly charged polymers, it is postulated that electrostatic interactions predominate. It is further speculate that the average molecular extension varies with polylysine concentration because molecular extension forces (due to the mounting procedure) balance against electrostatic forces, which are generated at the surface. The molecule may be thought to flow laterally onto the surface and the attachment of its individual binding sites in not necessarily a synchronous process. At low polylysine concentration, the density of polylysine on the surface is minimal so there may not be enough binding sites to hold an extended molecule with stability. Thus any lambda DNA molecule bound to the surface will appear as a random coil. At high polylysine concentration, abundant binding sites overwhelm any flow forces and the molecule immediately forms electrostatic bonds on a small area, quenching molecular translation and further extension. Efficient binding of molecules is expected. At moderate concentration, flow and electrostatic forces are probably balanced, to some extent, so that maximum extension can occur.

For optical mapping the conditions chosen were reflected in polylysine concentrations between $10^{-6}$ and $10^{-7}$ g/ml. producing molecules extended from 100 to 140% (see FIG. 16) of the polymer contour length. It is speculated that polymer contour length over-extension is due to helix unwinding by the ethidium homodimer (Guo et al., Nature 359:783–784, 1992; Guo et al., J. Biomol. Structure & Dynamics 11:1–10, 1993) and fluid flow forces.

Imaging restriction endonuclease digestion

Molecules were first fixed onto the polylysine coated surface by sandwiching a sample between a treated coverslip and a slide. The DNA sample consisted of DNA, restriction buffer minus magnesium ions, β-mercaptoethanol and a fluorochrome. It was found that ethidium homodimer (Glazer et al., Proc. Natk. Acad. Sci. U.S.A. 87:3851–3855, 1990) was compatible with most restriction endonucleases. Coverslips were sealed and a small hole in the slide was used as an inlet for restriction enzyme and magnesium ions.

Restriction digests were originally imaged using a SIT camera and a 512×512 pixel digitizing system housed in a Macintosh computer3. A cooled CCD was later obtained having higher spatial resolution (1032×1316 pixel), which produced images with less noise, less spatial distortion, and better linearity. It is the preferred instrument for imaging small DNA molecules (below 20 kb). Starting with high contrast, noise-free images simplifies image processing procedures and streamlines data extraction techniques.

Figure 17A:
Figure 17B:
Figure 17C:
Figure 17D:
Figure 17E:
Figure 17F:
Figure 17G:
Figure 17H:
Figure 17I:
Figure 17J:
Figure 17K:
Figure 17L:
Figure 17M:
Figure 17N:
Figure 17O:
Figure 17P:
Figure 17Q:
Figure 17R:
Figure 17S:
Figure 17T:
Figure 17U:
Figure 17V:
Figure 17W:

Our previous optical mapping protocol required time lapse imaging of the restriction endonuclease activity. Using surface fixed molecules, final results are simply imaged. Since molecules were imaged only once, long exposure times of 20–60 seconds and an elevated illumination level were used. Optimum exposure times vary with magnification and the desired number of gray levels. FIGS. 17A–17W shows typical images of lambda clone DNA molecules. 800 bp DNA fragments were easily imaged (FIG. 17w). Generally 20–80×62 micron microscope fields were imaged, containing approximately 100 suitable molecules.

The fixation conditions chosen optimized molecular extension and provided a reasonable number of surface-bound molecules. Fixation conditions, however, are not perfect so that not all molecules were optimally extended, as indicated by the data shown in FIG. 16, and some molecules intersected. Imperfectly fixed molecules were not selected for map-making. FIG. 17 shows typical molecules selected for map-making.

Mass determination by fluorescence intensity and apparent length measurements.

The size resolution of fluorescence microscopy is approximately 0.1 microns which translates into approximately 300 bp of B-DNA. Theoretically, smaller molecules can be detected, but with no spatial resolution. The usable size range of the system described here extends from 28 kb to 800 bp (see FIGS. 17A–17W and FIGS. 18A–18D) and is based on measuring relative apparent lengths and relative fluorescence intensities of restriction endonuclease fragments from the same parental molecule. This is similar to the technique used in Example 13, above, to construct restriction maps of *Saccharomyces cerevisiae*.

Use of surface mounted rather than gel mounted1 DNA molecules has reduced the sizing limit from 60 kb to 800 bp. Another notable difference is the greatly improved pooled SD: 3.1 kb vs. 36 kb for intensity and 1.9 kb vs. 47 kb for length. The pooled SD for fragments under 7 kb was 1.3 kb by intensity and 0.74 kb by length. Excluding samples with many adjacent short fragments, the surface fluorescence intensity and length data is very reproducible down to 800 bp, whereas previous results gave poor results below 60 kb. The overall relative error (which was the same for length and intensity) of 5% for large fragments is comparable to errors in sizing by agarose gel electrophoresis. It rises to 10% when small fragments (5 kb to 800 bp) are included. Note that 10% of 800 bp is 80 bp which contains about 30 fluorochromes. The gel sizing error was 5 to 8%.

Figure 18A:
Figure 18B:
Figure 18C:
Figure 18D:

Restriction fragments from 800 bp to 5.1 kb were consistently under-sized by fluorescence intensity measurements, and consequently, neighboring long fragments were overestimated. However, the pooled standard deviation for small fragments was only 1.3 kb. This suggests that the measurements are precise, that the deviation is caused by some unknown systematic effect, and that it should be subject to calibration to correct for a systematic error. FIG. 18b shows a separate plot of fluorescence intensity determined masses versus gel electrophoresis data. The best fit line through the origin was used as a calibration curve to correct small fragments. Large fragments were adjusted to maintain the total size. FIG. 18c shows the results after correction. FIG. 18d shows the relative apparent length results.

Because the digest is imaged after the fact, images of many molecules can be collected from a single sample in a short time. This makes averaging results to reduce noise very feasible. Obviously, averaging cannot improve the situation if the initial measurements are so noisy that different fragments cannot be distinguished. For lambda clones, the 11 kb size difference between the cloning arms (20 and 9 kb) makes distinguishing one end of the molecule from the other trivial even when the noise approaches two standard deviations.

Optical Maps of Lambda Clones.

Figure 19:
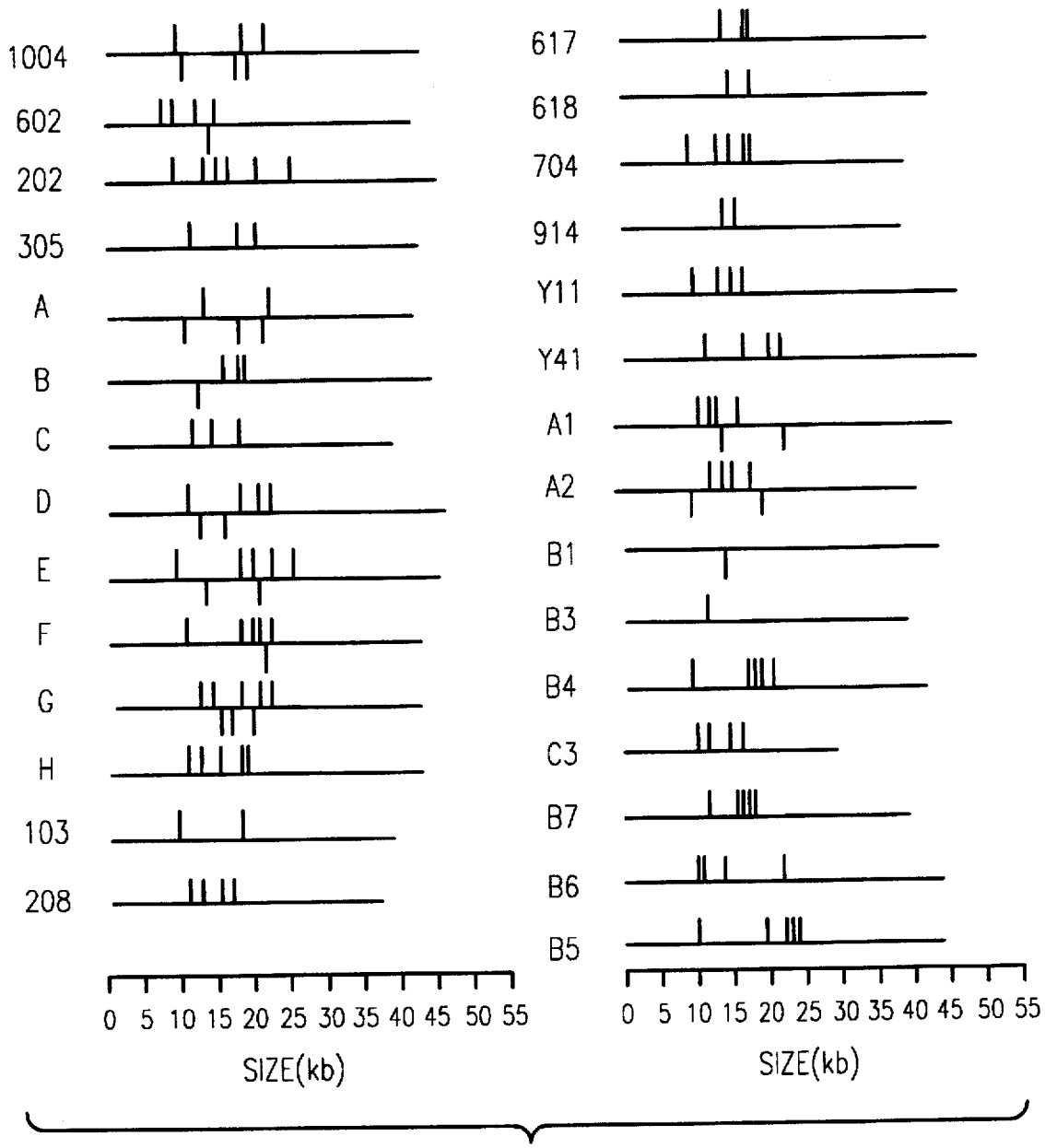
Figure 20A:
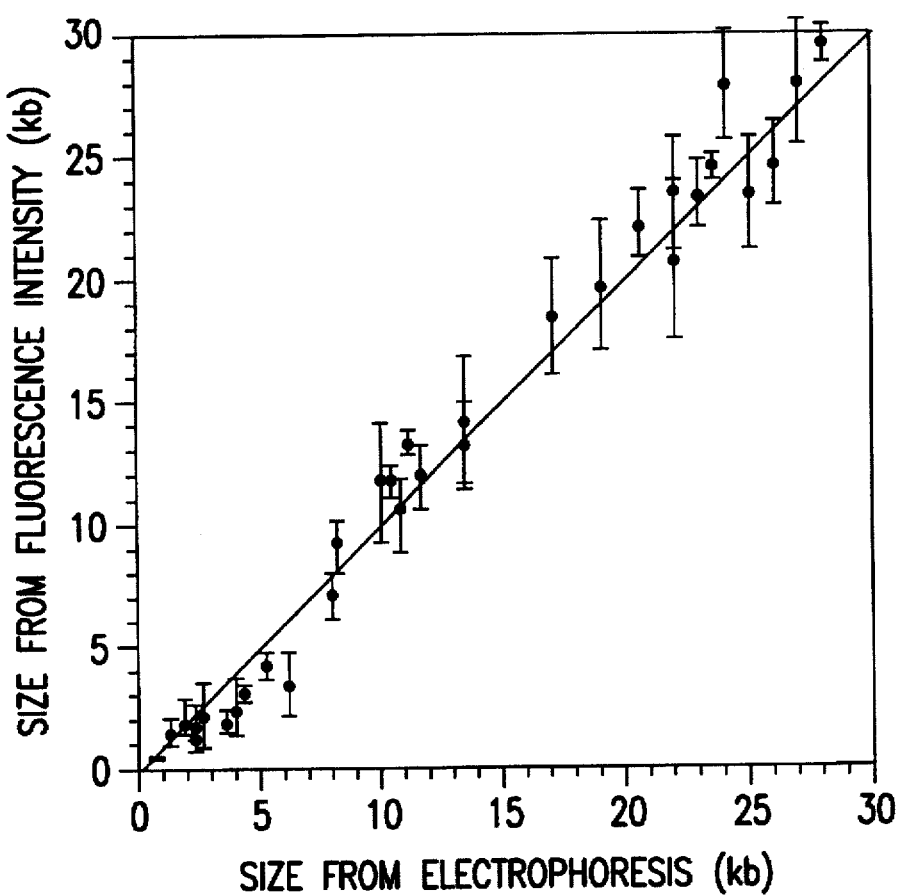
Figure 20B:
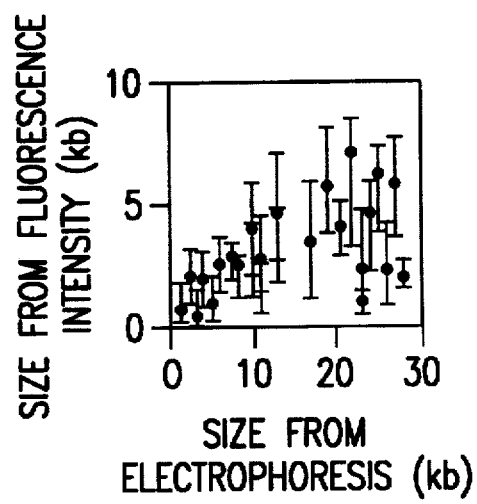
Figure 20C:
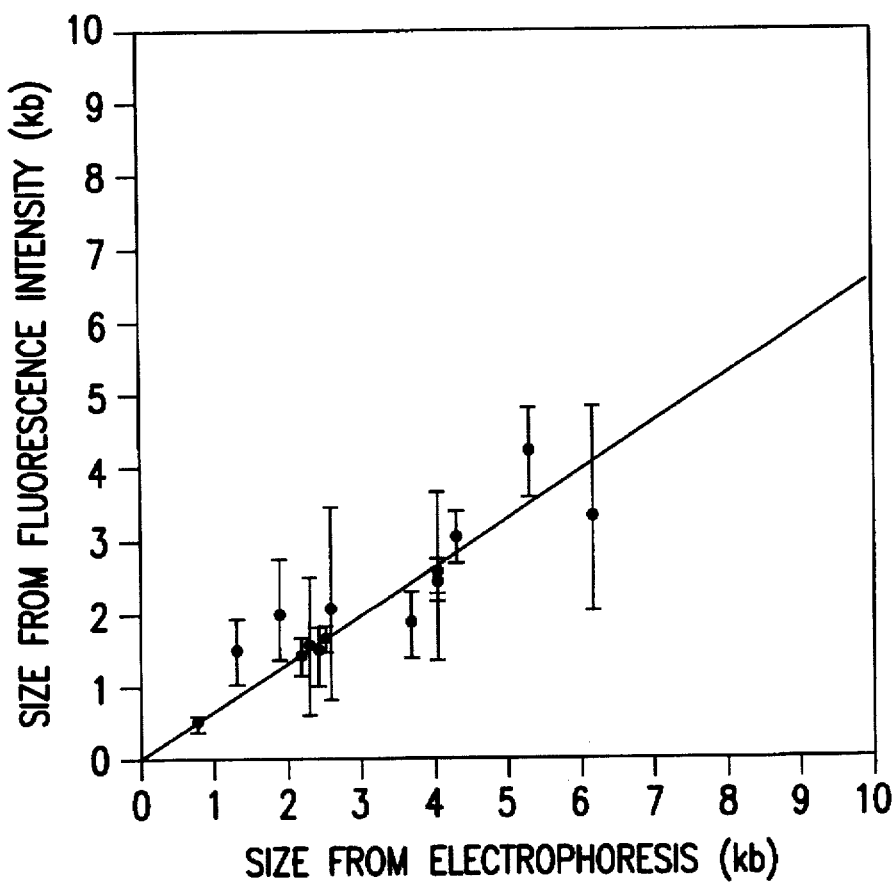
Figure 20D:
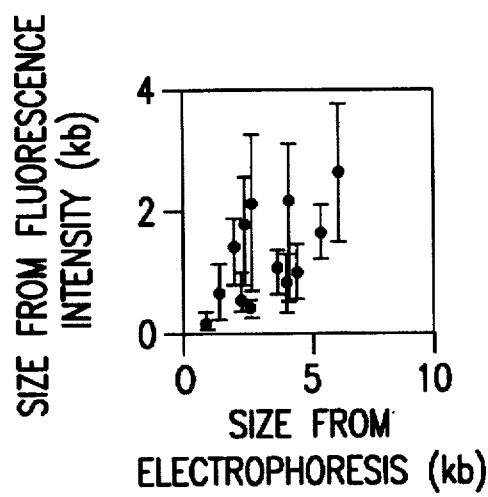
Figure 20E:
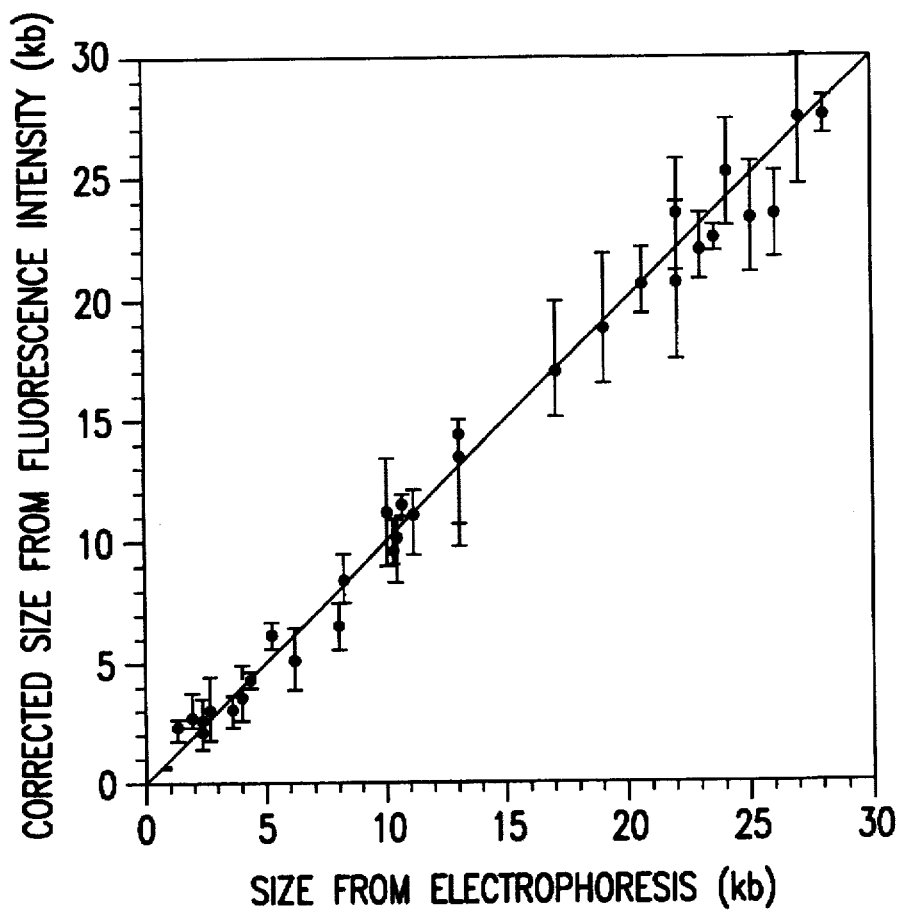
Figure 20F:
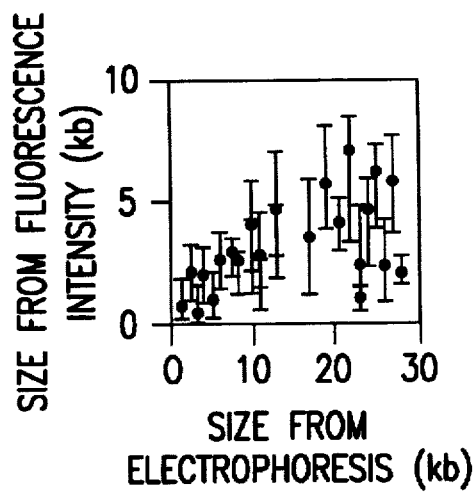
Figure 20G:
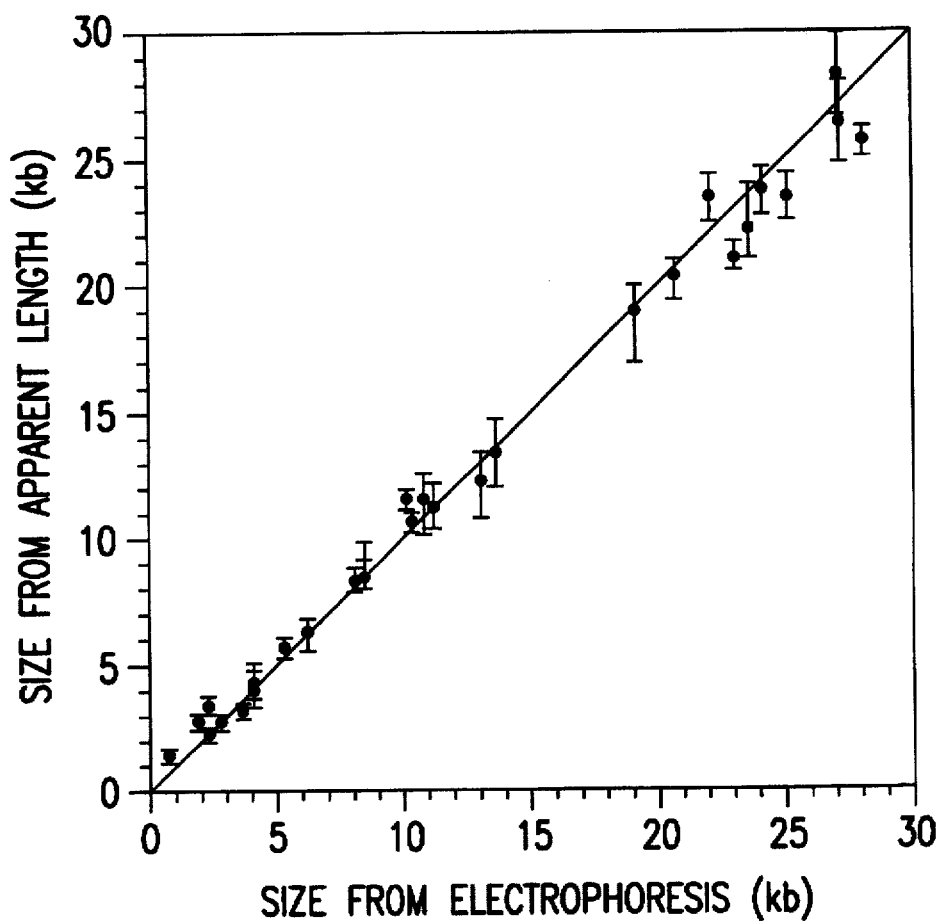
Figure 20H:
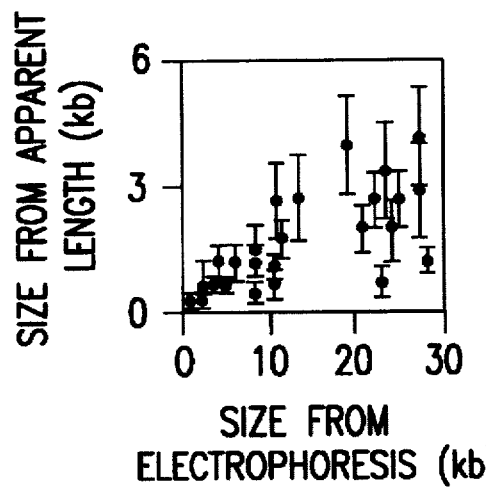

FIG. 19 shows the EcoRI and BamH I maps constructed by Optical Mapping, of Lambda FIX II clones derived from the mouse Pygmy locus19. Table 1 shows the fragment sizes. FIG. 20 shows typical cleavage patterns by enzymes which cut at the polylinker site and therefore permit absolute size calculations based on the known size of the vector arms rather than on PFGE measurements of uncut clones. Table 2 shows results from PFGE, fluorescence intensity, and apparent length measurements of digests with enzymes (Sal I, NotI or SstI) which cut at the polylinker site. Optical mapping with these enzymes permits calculation of the total size of the clone. This value can then be used to calculate sizes for Optical Mapping with enzymes that do not cut the polylinker.

Ordered restriction endonuclease maps were constructed using procedures developed in Example 13, above. Briefly, the correct number of fragments by constructing a histogram for each clone consisting of the number of imaged restriction fragments per parental molecule, and its frequency. Generally 100 molecules of each clone were analyzed, and 5–10 molecules were selected for map construction based fragment number and map content. Usually these molecules originated from histogram bins containing the maximum number of restriction fragments. Studying molecule images after digestion provided fragment order, and relative fragment masses were assigned by relative fluorescence intensity and relative apparent length measurements. Fragment lengths were measured starting at the midpoint of the gap between fragments. The final map is reported as an average of restriction fragment sizes derived from similar molecules. Molecules were considered similar if the fragment number agreed and homologous fragment sizes were within the stated measurement precision.

The histogram analysis of the numbers of cut sites for each molecule was necessary because small numbers of molecules were analyzed and digestion efficiencies were not entirely quantitative. Typically it was found that 5–30% of imaged molecules were fully digested. The efficiency varied with fragment number, size and pattern. Contiguous restriction fragments below 1.5 kb were sometimes indistinguishable. Fragments less than 1 kb sometimes broke free from the surface and were not observed. It is expected that these problems would be obviated by imaging sufficient numbers of molecules. Additionally, data from partially digested clones were used to confirm maps created from fully digested molecules.

Data from partially cut molecules or from fully cut molecules with defective images was sometimes useful. When some but not all fragments could be measured, or when a fragment could be unambiguously interpreted as a particular partial digestion product, the ratios of the known fragments to all combinations of sums of fragments were calculated and averaged for all available data. These ratios were also calculated from fully cut perfectly imaged molecules. Some fully cut molecules could not be used directly for intensity calculations because one of the vector arm fragments was contaminated with intensity that clearly did not belong to the fragment or because the fragment extended over the edge of the image. Similarly, some fragments-could not be used for length calculations. In those cases, a full set of fragment sizes was calculated for the molecule by using ratios of unknown fragments to known fragments.

The maps were first constructed by optical mapping and then confirmed by gel electrophoresis data generated in this laboratory and compared to the previously constructed contig maps. Optical lapping requires an internal size standard: the uncut clone or clearly identifiable fragments such as the vector arms. For enzymes which do not cut the polylinker, gel data was used to size the uncut clone. These sizes were also obtained by Optical Mapping using enzymes (Not I, Sal I, and Sst I) which cut the polylinker (Table 2, FIG. 20). Overall, the agreement between electrophoresis based maps and optical maps was excellent in terms of fragment size and order. Frequently it was found that the optical maps more accurately reported fragment sizes than agarose gel electrophoresis based measurements, particularly when data from 10 molecules were averaged. Given our level of sizing precision, we did not reliably detect fragments below 800 bp.

TABLE 1

Ordered restriction maps for 28 lambda clones

| Clone | EcoRI restriction fragment lengths | | | | | | BamHI restriction fragment lengths | | | |
|---|---|---|---|---|---|---|---|---|---|---|
| 1004 | 9.5 | 10.2 | 4.3 | 22.0 | | | 10.7 | 6.2 | 1.7 | 27.4 |
| 602 | 11.1 | 4.7 | 4.2 | 26.6 | | | 16.6 | 30.4 | | |
| 202 | 9.5 | 4.5 | 2.0 | 4.0 | 21.5 | | | | | |
| 305 | 11.9 | 7.3 | 2.9 | 23.5 | | | | | | |
| A | 12.8 | 11.4 | 20.8 | | | | 10.9 | 7.4 | 6.1 | 20.6 |
| B | 17.7 | 2.3 | 3.3 | 23.6 | | | 23.5 | 23.5 | | |
| C | 12.2 | 2.8 | 4.2 | 22.8 | | | | | | |
| D | 11.4 | 8.3 | 3.7 | 1.9 | 24.4 | | 18.8 | 3.0 | 27.9 | |
| E | 10.5 | 9.5 | 1.8 | 2.5 | 2.5 | 22.1 | 13.5 | 9.0 | 26.4 | |
| F | 10.2 | 8.7 | 2.2 | 1.0 | 2.9 | 21.7 | 22.4 | 24.3 | | |
| G | 11.0 | 1.9 | 4.2 | 3.2 | 2.5 | 21.2 | 14.2 | 2.0 | 3.8 | 24.0 |
| H | 11.5 | 1.8 | 4.1 | 3.8 | 1.8 | 22.7 | | | | |
| 103 | 10.0 | 8.2 | 23.8 | | | | | | | |
| 208 | 10.5 | 1.6 | 4.2 | 2.3 | 21.0 | | | | | |
| 617 | 15.3 | 2.5 | 1.0 | 27.6 | | | | | | |
| 618 | 15.7 | 2.5 | 27.6 | | | | | | | |
| 704 | 10.5 | 2.0 | 4.4 | 0.7 | 1.7 | 22.5 | | | | |
| 914 | 16.1 | 2.2 | 27.8 | | | | | | | |
| Y11 | 11.6 | 4.2 | 2.5 | 2.4 | 23.6 | | | | | |
| Y41 | 12.4 | 5.6 | 4.1 | 2.6 | 24.6 | | | | | |
| A1 | 15.1 | 1.7 | 1.2 | 2.8 | 25.2 | | 16.3 | 9.2 | 20.5 | |
| A2 | 13.7 | 2.8 | 1.8 | 1.3 | 24.7 | | 10.5 | 11.3 | 22.5 | |
| B1 | | | | | | | 14.5 | 22.5 | | |
| B3 | 12.0 | 30.0 | | | | | | | | |
| B4 | 9.5 | 8.0 | 1.6 | 1.5 | 2.1 | 22.1 | | | | |
| B6 | 11.2 | 1.6 | 9.7 | 1.8 | 3.0 | 22.5 | | | | |
| B7 | 12.7 | 4.4 | 1.6 | 1.5 | 1.0 | 21.9 | | | | |
| C3 | 11.6 | 2.6 | 3.8 | 2.3 | 22.6 | | | | | |

TABLE 2

Sizes of insert DNA of lambda clones by PFGE and Optical Mapping

| Clone (Enzyme*) | PFGE (kb)† | Optical Mapping (kb)§ | |
|---|---|---|---|
| | | Intensity | Length |
| 1004 (N) | 17.0 ± 0.9 | 16.2 ± 0.9 | 16.0 ± 1.0 |
| 602 (N) | 17.6 ± 0.9 | 16.5 ± 1.0 | 16.6 ± 1.0 |
| 202 (N) | 12.5 ± 0.6 | 13.2 ± 0.8 | 13.0 ± 0.8 |
| 305 (S) | 16.6 ± 0.8 | 17.4 ± 1.0 | 17.2 ± 1.1 |
| A (S) | 16.0 ± 0.8 | 15.2 ± 0.9 | 15.0 ± 1.0 |
| B (N) | 17.9 ± 0.9 | 17.5 ± 0.9 | 17.8 ± 1.0 |
| C (S) | 13.0 ± 0.7 | 12.5 ± 0.8 | 12.2 ± 0.9 |
| D (S) | 20.7 ± 1.0 | 20.0 ± 1.1 | 20.2 ± 1.2 |
| E (S) | 19.9 ± 1.0 | 20.6 ± 1.2 | 20.8 ± 1.2 |
| F (S) | 17.7 ± 0.9 | 17.0 ± 0.9 | 16.8 ± 0.9 |
| G (S) | 15.0 ± 0.8 | 17.0 ± 0.9 | 17.2 ± 0.9 |
| H (S) | 16.7 ± 0.8 | 17.6 ± 0.8 | 17.7 ± 0.8 |
| 103 (S) | 13.0 ± 0.7 | 14.0 ± 0.8 | 13.6 ± 0.9 |
| 208 (S) | 10.6 ± 0.5 | 9.7 ± 0.7 | 9.4 ± 0.8 |
| 617 (S) | 17.4 ± 0.9 | 18.2 ± 0.9 | 18.6 ± 1.0 |
| 618 (S) | 16.8 ± 0.8 | 16.0 ± 0.8 | 15.5 ± 0.8 |
| 704 (S) | 12.8 ± 0.6 | 14.0 ± 0.8 | 13.6 ± 0.7 |
| 914 (S) | 17.1 ± 0.9 | 18.0 ± 0.7 | 18.4 ± 0.9 |
| Y11 (S) | 15.3 ± 0.8 | 16.2 ± 0.8 | 16.5 ± 0.8 |
| Y41 (S) | 20.3 ± 1.0 | 19.1 ± 0.9 | 19.5 ± 1.0 |
| A1 (T) | 17.0 ± 0.9 | 16.4 ± 0.9 | 16.2 ± 0.9 |
| A2 (T) | 15.3 ± 0.8 | 16.0 ± 0.9 | 16.4 ± 0.9 |
| B1 (T) | 8.0 ± 0.4 | 8.6 ± 0.5 | 9.3 ± 0.5 |
| B3 (T) | 13.0 ± 0.7 | 13.8 ± 0.9 | 13.7 ± 0.9 |
| B4 (N) | 15.8 ± 0.8 | 15.0 ± 0.9 | 15.2 ± 0.9 |
| B6 (N) | 20.8 ± 1.0 | 20.1 ± 1.3 | 20.0 ± 1.5 |
| B7 (N) | 14.1 ± 0.7 | 14.7 ± 0.9 | 15.0 ± 0.8 |
| C3 (N) | 13.9 ± 0.7 | 13.1 ± 0.7 | 13.3 ± 0.7 |

*Enzymes N: Not I, S: Sal I, T: Sst I.
†PFGE size ± assumed 5% sizing error
§Fluorescence intensity and apparent length ±90% confidence interval on mean

EXAMPLE 15

Ordered Restriction Endonuclease Maps of Yeast Artifical Chromosome Created by Optical Mapping on Surfaces In this Example, a new surface mounting technology for the rapid construction of ordered restriction maps from individual DNA molecules is described. Specifically, such technology involves the utilization of polylysine-coated derivatized glass surfaces The successful use of this technology is demonstrated by the accurate optical restriction maps constructed from yeast artificial chromosome DNA molecules mounted on the derivatized glass surfaces.

15.1. MATERIALS AND METHODS

YACs, DNA preparation and PFGE restriction mapping. Gel inserts were prepared from five YAC clones (Murray and Szostak, Nature 305:189–93, 1983; Burke et al., Science 236:806–812, 1987) named 7H6, 314, 3H5, 5L5 and 6H3 and yeast strain AB972 following the standard protocol (Schwartz and Cantor, Cell 37: 67–75, 1984; Ausubel et al., eds., in Current Protocols in Molecular Biology, Vol. 1, 6.10.1–5, John Wiley & Sons, New York, N.Y., 1994). Pulsed field gel electrophoresis (PFGE) was performed on an ED apparatus (Schwartz et al., Nature 342:575–576, 1989). YAC sizes were measured by comparing relative electrophoretic mobilities to lambda DNA concatamers and yeast chromosomes. PFGE maps of 7H6 and 314 were constructed by Southern blotting YAC DNAs cut with different restriction enzymes. Blots were hybridized (Church and Gilbert, Proc. Natl. Acad. Sci. U.S.A. 81:1991, 1984) with radiolabelled human Alu repeat probe. Ordered maps of 3H5, 5L5 and 6H3 were constructed by partial digestion (Smith and Birnstiel, Nucleic Acids Res. 3:2387–2399, 1976) using probes derived from the right and left cloning arms.

Surface preparation, DNA mounting, and digestion. Glass coverslips were cleaned in excess 3M HCl at 95° C. for 2 hours and then thoroughly washed with high purity water. Cleaned glass coverslips were derivatized by immersion for varying lengths of time in freshly prepared 0.10M 3-aminopropyltriethoxysilane (APTES; Sigma), pH 3.5, at 65° C. After APTES treatment, coverslips were washed thoroughly with high purity water and air dried. In order to create a chamber for DNA mounting glass microscope slides were drilled to create a 1 cm diameter hole which was then sandwiched between two coverslips. First the APTES treated coverslip was attached with silicone vacuum grease. Then 20 µl of DNA in molten agarose gel were slowly spread onto the APTES derivatized surface with a pipetman. The top of the chamber was then quickly sealed with an untreated coverslip using vacuum grease. Chambers were incubated on a 45° C. heating block for 10–30 minutes to allow DNA in the molten agarose to transfer to the derivatized glass surface. Slightly tilting the chambers generated a mild fluid flow and helped to stretch out the DNA during transfer. After transfer, chambers were chilled at 4° C. for 5 minutes to set the gel. Then the chambers were opened and 3–5 units of restriction endonuclease, diluted in appropriate buffer, was added to the gel surface. Chambers were resealed and incubated 1–2 hours at 37° C. After digestion, samples were stained either with ethidium homodimer (Molecular Probes, 0.1 ng/ml ethidium homodimer, 15 mM EDTA (pH 7.5) and 10% 2-mercaptoethanol) or oxazole yellow homodimer (YOYO-1) (Molecular Probes, 0.1 ng/ml YOYO-1, 15 mM EDTA, pH 7.5, and 20% 2-mercaptoethanol). Dilution of high molecular weight DNA. It is important to control DNA concentration when mounting DNA molecules for optical mapping. DNA molecules excised as bands from low melting temperature PFGE gels (Seaplaque, FMC) often must be diluted before mounting, as follows: Incubate gel band for 2 hours in 0.01 mM spermine tetrachloride (Sigma) in TE buffer (10 mM Tris, pH 7.6; 1 mM EDTA). This step condenses the gel-embedded DNA molecules into shear resistant particles, protecting them during dilution. Next melt gel bands at 72° C. for 7 minutes and mix with additional molten low melt agarose containing 0.01 mM spermine. Vortexing at this step causes little apparent breakage. Diluted samples are made into gel inserts (Schwartz and Cantor, Cell 37:67–75, 1984) which are then washed 5 times, 30 minutes each with shaking, with TE buffer to remove the spermine and thereby decondense the DNA particles. The first wash is in TE supplemented with 100 mM NaCl. Gel inserts were stored in 10 mM Tris, 0.5 mM EDTA, pH 7.6.

Microscopy, image analysis and map construction. DNA molecules were imaged using a Zeiss Axioplan or Axiovert 135 microscope equipped for epi-fluorescence (filter pack for green excitation and red emission) and a 100× Plan-Neofluar objective (Zeiss) coupled to a Hamamatsu C2400 SIT camera (Example 13). A typical 100 micron microscopic field contained three to five molecules suitable for analysis. Efficiency of restriction endonuclease digestion was scored by counting gaps in molecules with known restriction maps. Digestion efficiencies did not differ among the enzymes used in this study. Restriction maps were constructed as described in Example 13.

15.2 RESULTS

Optimizing mounting conditions for large DNA molecules on derivatized glass surfaces. Large DNA molecules are easily broken during transfer (Albertsen et al., Proc. Natl. Acad. Sci. U.S.A. 87:4256–60, 1990) and maintaining their integrity during surface mounting operations required special effort. Molten agarose has been used to mount, with high efficiency, DNA molecules greater than i megabase in size (Example 13), but it is sometimes difficult to bring an entire molecule into sharp focus and the agarose gel scatters light. To eliminate these problems with agarose fixation, the fluid turbulence damping properties of molten agarose were combined with the stability of surface mounting by fixing large DNA molecules dissolved in molten agarose onto APTES derivatized glass surfaces (Lyubchenko et al., J. of Biomolecular Struct. and Dynamics 10:589–606, 1992; Weetal, Methods Enzymol. 44:19, 1976). It was reasoned that this combined technique would enable high contrast imaging, since it would minimize the amount of agarose gel between DNA molecules and the microscope objective. This approach was evaluated by testing whether DNA in an agarose matrix could interact with an APTES modified glass surface to produce optimally elongated and stabilized molecules in an environment conducive to restriction endonuclease activity.

Figure 21:
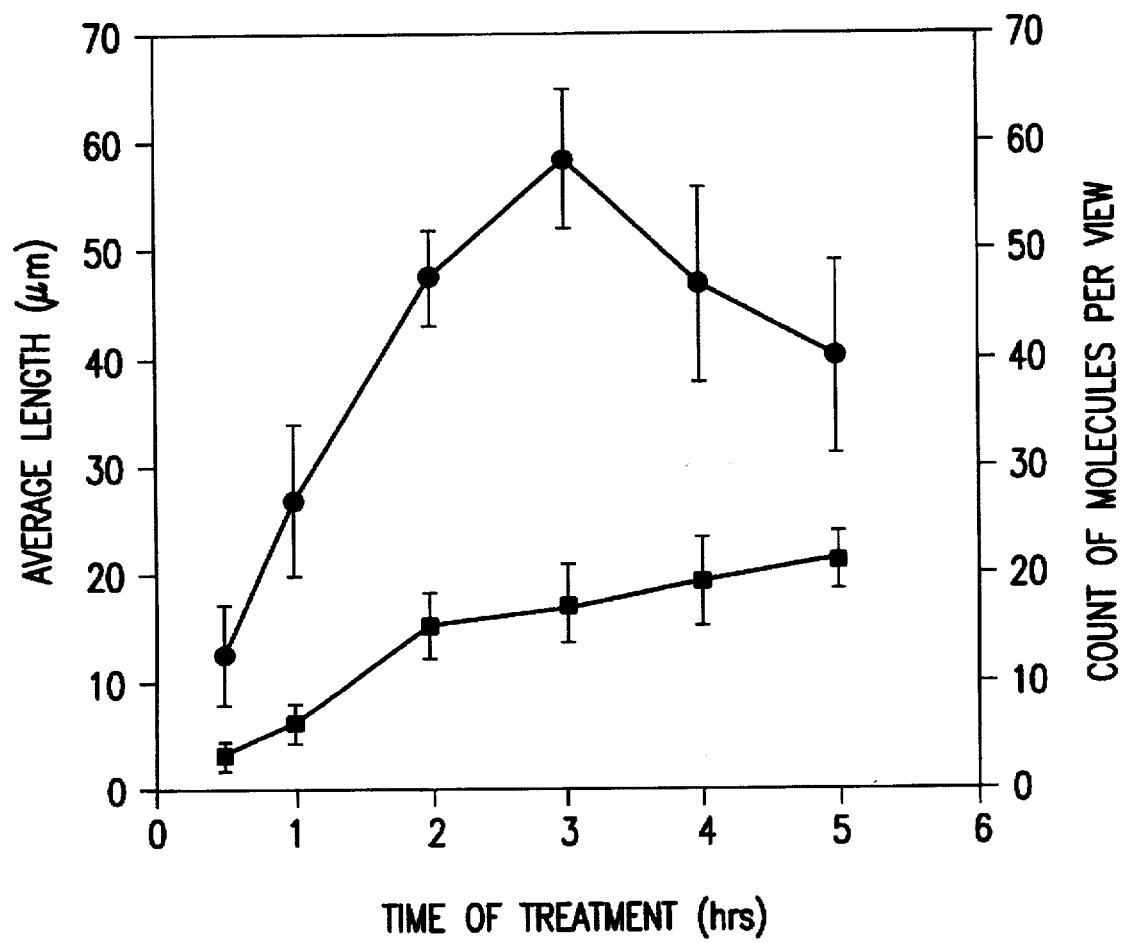
Figure 22A:
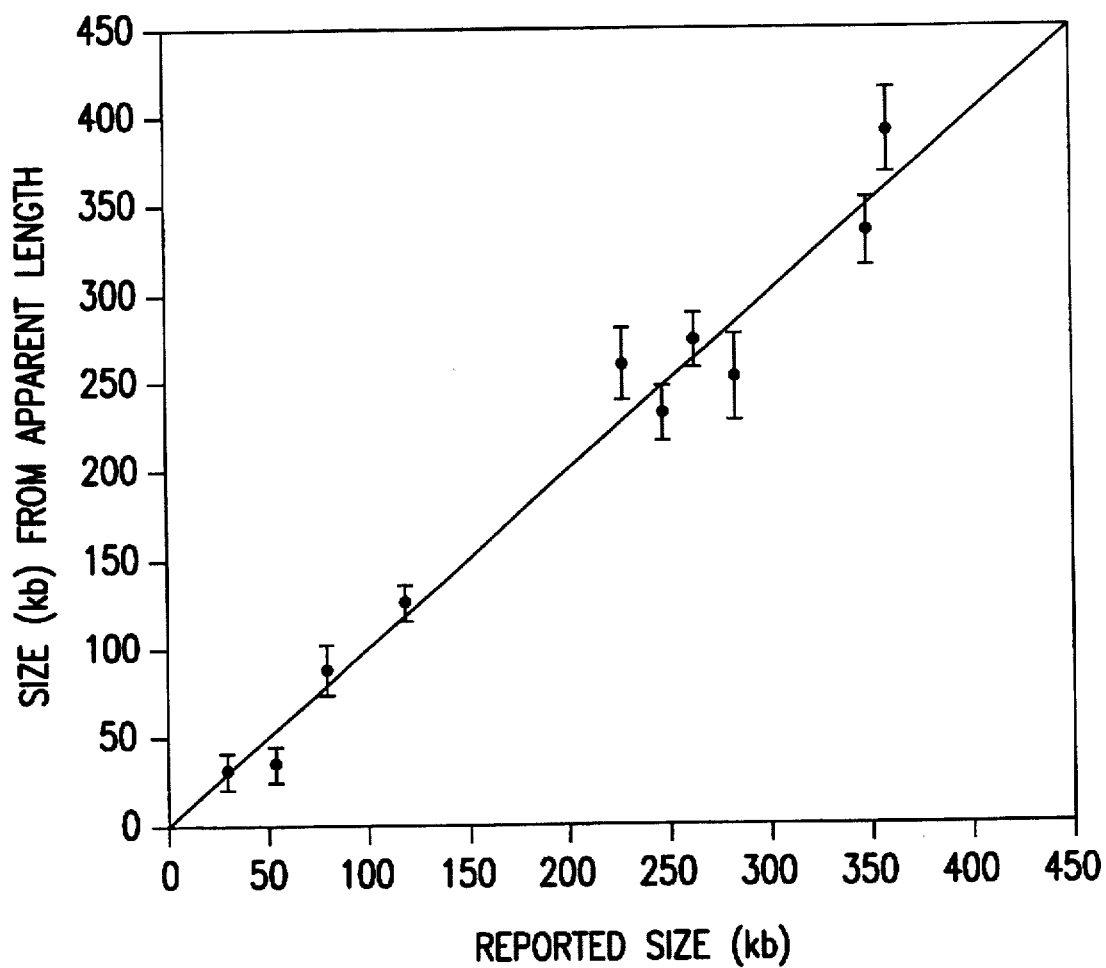
Figure 22B:
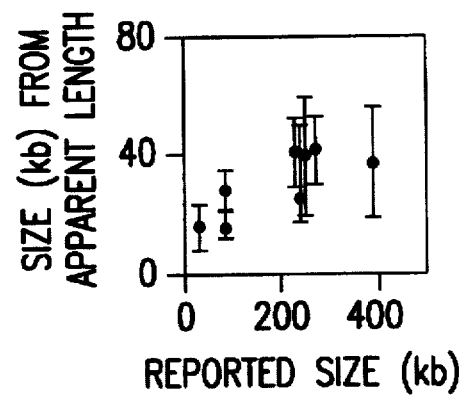
Figure 22C:
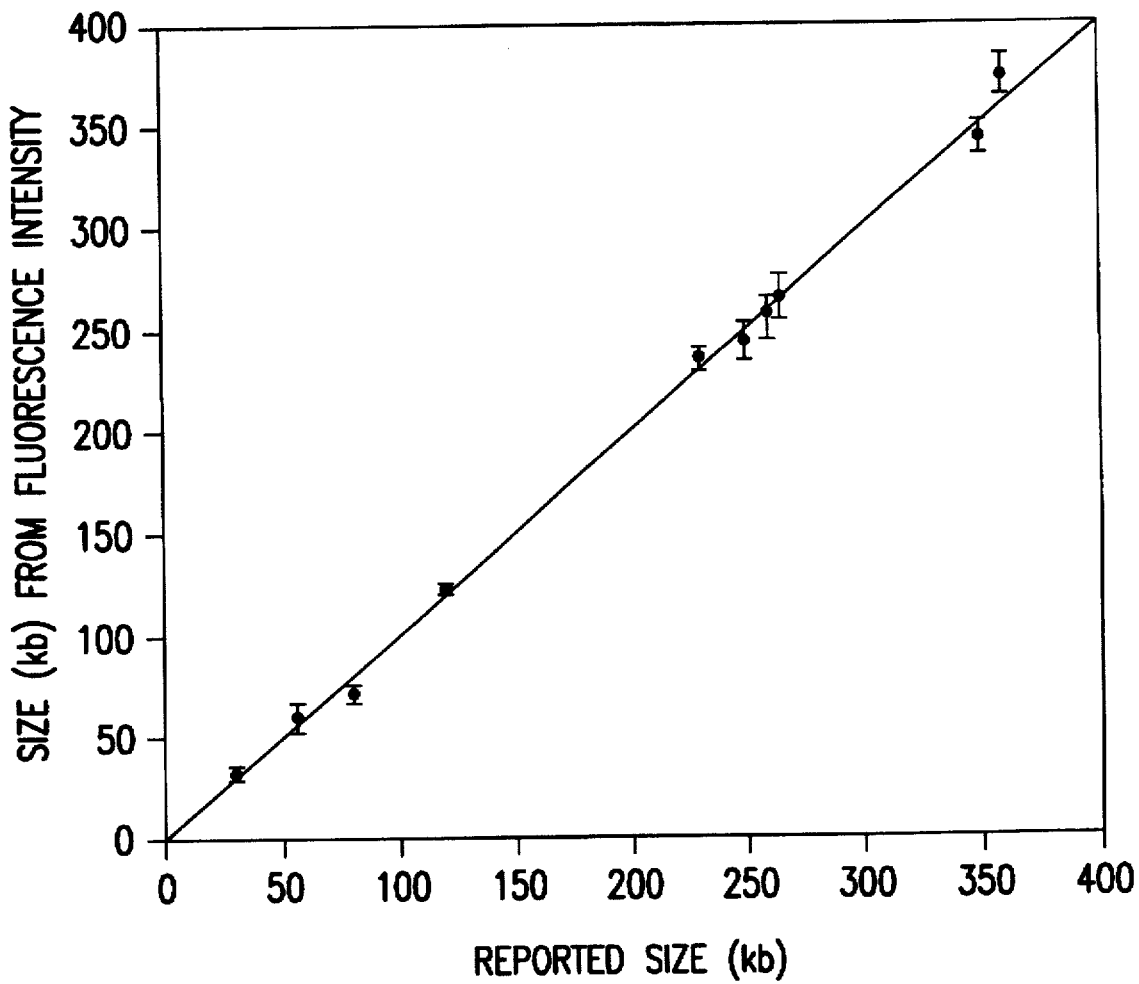
Figure 22D:
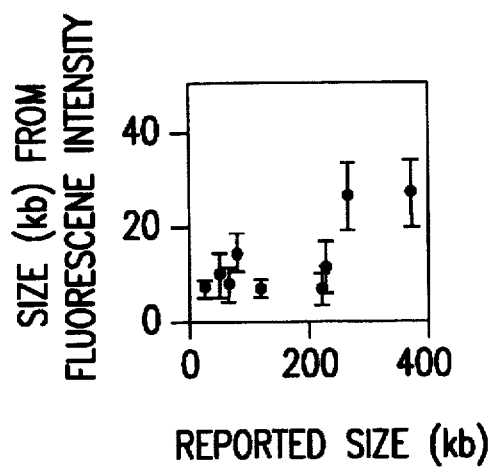

Surface derivitization conditions affect two important aspects of DNA fixation: molecular adhesion and elongation. Ideally molecules should be tightly attached and well stretched out. In fact these two conditions are antagonistic— too much adhesion will prevent elongation, whereas too little may allow optimal elongation but will not fix sufficient numbers of molecules to the surface. To achieve a suitable balance, the amount of APTES was titrated on the surface against the measured average molecular length of deposited molecules. Fluorescence microscopy was used to image stained molecules on APTES modified glass coverslips. The incubation time of cleaned glass coverslips in a 0.10M APTES solution was varied from 0.5 to 5 hours, deposited undiluted $Saccharomyces\ cerevisiae$ (AB972) chromosome I (240 kb) in molten agarose, and measured molecular lengths from fluorescence micrographs. The number of molecules attached to the surface was also counted. The goal was to maximize molecular extension while maintaining a usable number of molecules on the surface. FIG. 21 shows a plot of APTES concentration versus average molecular extension and number of molecules per 100 $m^2$ field. At low APTES concentration, the average molecular extension as well as the number of molecules detected on the surface was minimal. The average molecular extension increased with APTES concentration and peaked at 3 hours; further increase in APTES concentration reduced molecular extension and, predictably, increased the number of molecules on the surface. It is not known exactly how large DNA molecules interact with an APTES modified surface. One may speculate that attractive electrostatic forces between DNA and the charged surface are balanced, to some extent, by the molecular flow forces generated during the mounting procedure. The surface charge density increases as more APTES is deposited, while flow forces remain constant. Thus, minimum molecular extension should be measured at high and low APTES surface densities. Based on the data shown in FIG. 21, it was initially decided to use glass surfaces incubated in APTES for 3 hours. This incubation time was found to produce a uniform extended length distribution; however, the molecules relaxed excessively during a 2 hour digestion. The APTES incubation time was then extended to 5 hours. At 5 hours, the mean length is roughly 55% that of the polymer contour length. A high degree of elongation facilitates the detection of small restriction fragments, but may inhibit restriction endonuclease activity. The next step was to assay restriction endonuclease activity (Example 13). Digestion of Mounted DNA Molecules. In previous optical mapping studies DNA molecules were typically elongated to roughly 30% of their polymer contour length. This degree of elongation was chosen to optimize image contrast: more condensed molecules have a higher fluorochrome density. Recently, longer image integration times were used to collect adequate information from lower density images. In this Example, surface mounted molecules were typically extended to 50–60% of their polymer contour length. It was found that such molecules were more effectively cleaved by restriction endonucleases than more condensed molecules mounted in agarose: 85% versus 50%. Efficiency was measured as the probability of cleavage at a given cognate site (Example 13). The overall image quality was greatly improved as well.

Mounting DNA molecules on a surface has a drawback—not only does most of the DNA in the molten agarose stick to the surface, fluorescent debris sticks as well. Thus, the DNA concentration had to be lowered since observation was limited to a single optical plane. A shear-free dilution protocol was developed based on spermine condensation (Gosule and Schellman, J. Mol. Biol. 121:311–326, 1978). The protocol successfully collapses DNA coils embedded within agarose so that molten agarose can even be vortexed without significant DNA breakage. The spermine DNA condensation/sample dilution step was used for all YAC samples. After dilution, spermine was removed by washing gel inserts in excess TE buffer.

Figure 23A:
Figure 23B:
Figure 23C:
Figure 23D:
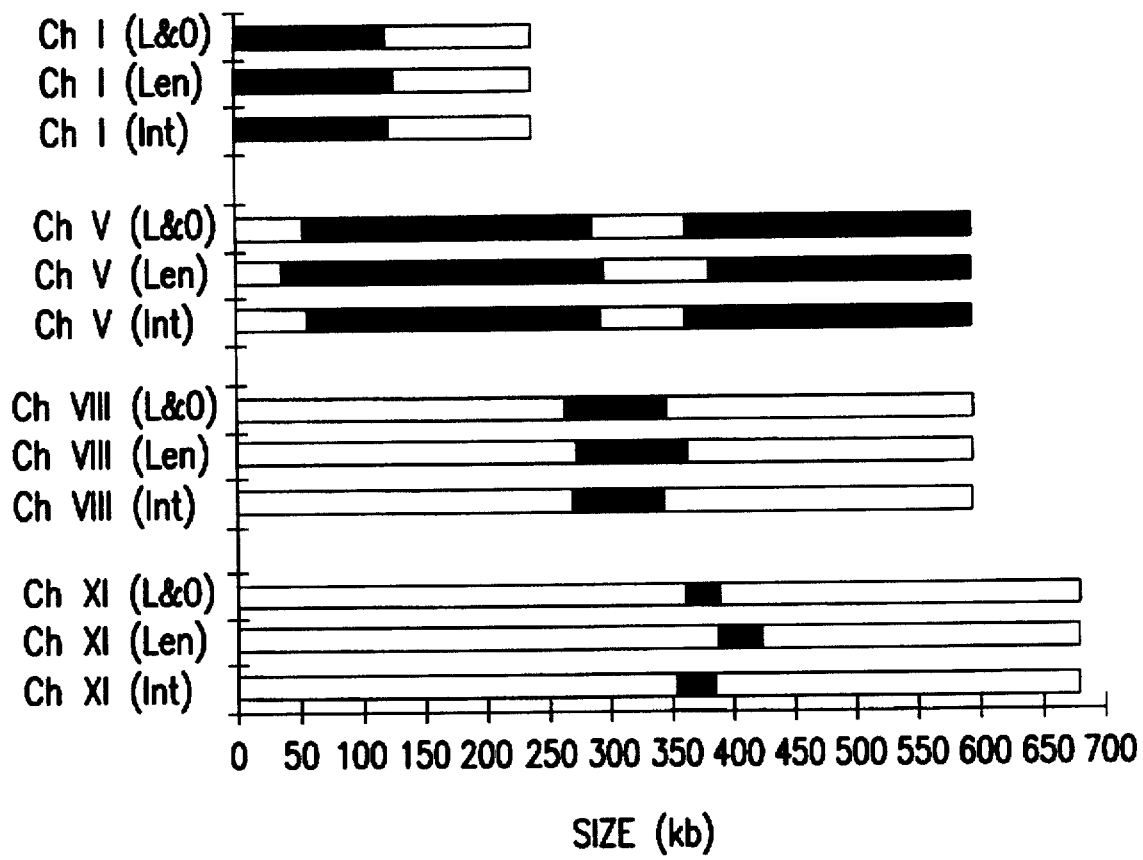
Figure 24A:
Figure 24B:
Figure 24C:
Figure 24D:
Figure 24E:
Figure 24F:
Figure 24G:
Figure 24H:
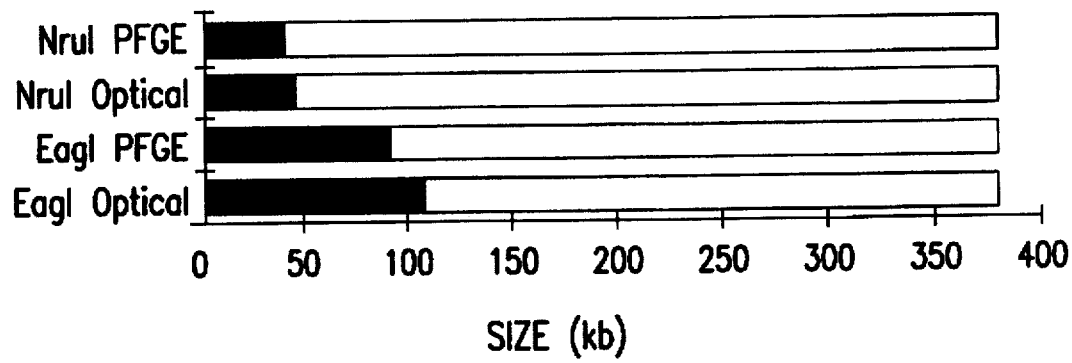
Figure 24I:
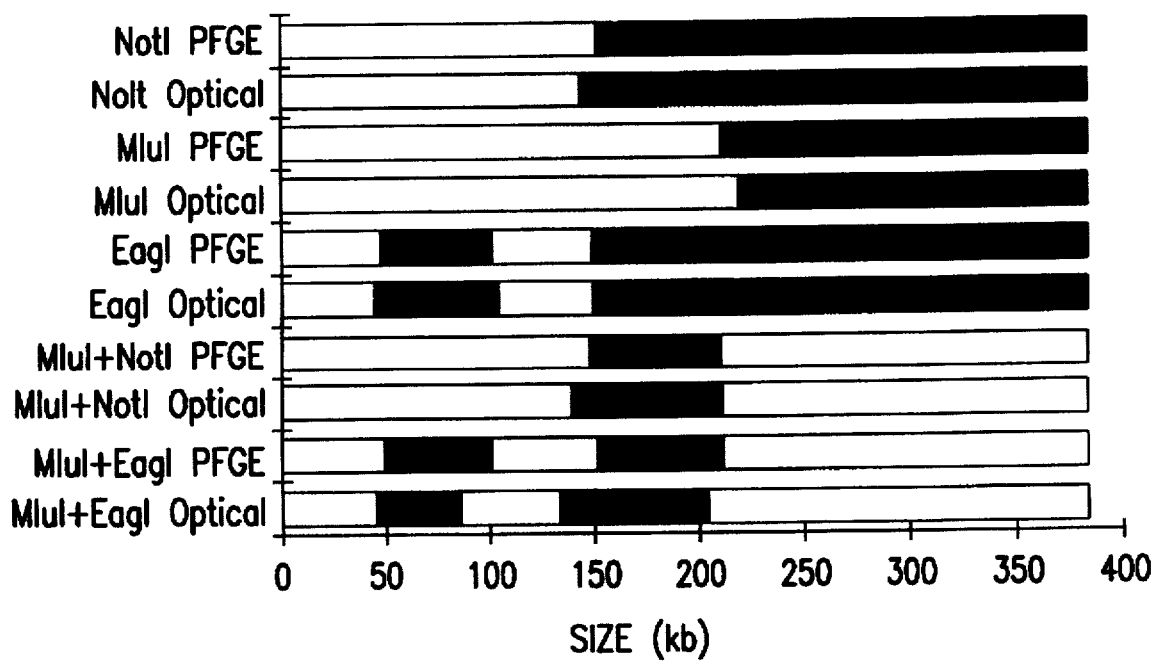

Mass Determination. A quantitative relationship between mass and the measured fluorescence intensity of a labeled DNA molecule, as imaged by fluorescence microscopy was previously demonstrated (Example 13). Additionally, a reliable relationship between microscopically imaged restriction fragment length and mass was established (Example 13). These studies were performed using DNA molecules fixed in agarose gel. Since the surface mounting conditions described in this example are different, the methods for mass determination had to be reevaluated. Surface mounted *S. cerevisiae* chromosomal DNA molecules were digested with NotI, and restriction fragment fluorescence intensity and length was measured. These measurements were plotted against the well established NotI fragment sizes of *S. cerevisiae* chromosomes (Example 13; Link and Olson, Genetics 127:681, 1991) (see FIGS. 22A–22D and 23A–23D). Fluorescence micrographs of typical molecules are shown in FIGS. 23A–23C. The most notable difference between fluorescence intensities measured for surface mounted molecules vs. gel mounted molecules (Example 13) is improved reproducibility: pooled standard deviation (SD) is 17 kb vs. 36 kb previously shown (in Example 13). Also, the fluorescence intensity data on surface mounted molecules is accurate down to 30 kb, whereas our previous gel mounting protocol gave poor results below 60 kb. The overall relative error with surface mounted molecules was 4%, identical to results obtained by standard methods (Link and Olson, Genetics 127:681, 1991) and the average of the coefficients of variation was 12%, indicating precision comparable to routine PFGE analysis. Mass determination by measuring length of surface mounted molecules is also superior to previous results with gel mounted molecules. The length measurements showed a pooled SD of 32 kb vs. 47 kb and the average of the coefficients of variation was 29%. The relative error was 7%, which was not as accurate as the fluorescence intensity data. These fragment sizing studies show that fluorescence intensity is more accurately and reliably correlated to mass than length. Overall, the images of surface mounted molecules were consistently in one focal plane. Good focus is essential for accurate fluorescence intensity measurements, whereas length measurements are less subject to error due to blurry images. Apparently, restriction fragments produced by digestion of surface mounted molecules vary in length more than fluorescence intensity values. Errors caused by length variation could be reduced by selecting only uniformly elongated DNA molecules.

Improved images with YOYO-1. New fluorochromes with improved DNA binding efficiencies and quantum yields have been developed recently. Oxazole yellow homodimer (YOYO-1) vs. ethidium homodimer were tested to optically map YAC clones 3H5, 5L5 and 6H3. The YOYO-1 images were brighter and of higher contrast than those made with ethidium homodimer. Also, while high salt conditions diminish the fluorescence emission of ethidium stained molecules, YOYO-1 stained molecules retain luminosity in high salt and under severe fixation conditions. Interestingly, serious photodamage to DNA was observed in solution with YOYO-1, manifested as double strand breaks, even in the presence of 2-mercaptoethanol. Fortunately, surface mounted YOYO-1 stained DNA molecules had no measurable photodamage (double-strand breaks) in the presence of 20% (v/v) 2-mercaptoethanol. Additional 2-mercaptoethanol was found to quench YOYO-1 fluorescence. The qualitatively superior image contrast attainable with YOYO-1 improved restriction fragment sizing results: the pooled standard deviation on the means calculated for YOYO-1 stained restriction fragments dropped to 11 kb from 17 kb and the average coefficient of variation decreased to 7% from 12%.

Restriction Digestion and Map Construction. Five YACs were optically mapped with restriction endonucleases MluI, EagI, NruI and NotI using the optimized APTES fixation and YOYO-1 staining conditions described above. In general, images were clear and high contrast. Maps were constructed using previously described procedures (Example 13), with minor modifications to exploit the potential of high contrast imaging. The analysis necessary for map construction was simplified, in comparison to the previous approach, since molecules were imaged after digestion. Long image integration times were used, and only one image was collected per microscope field. Previous procedures (Example 13) required the examination of a series of time lapse images and the analysis of 4–5 contiguous (temporal) images. The cleavage sites of surface mounted molecules were flagged by the appearance of gaps, and fragment ends occasionally displayed bright regions of condensed DNA. To orient these maps, the YACs were further characterized by double digests. Some of the resulting maps include as many as 6 fragments ranging in size from 40–180 kb. The overall agreement between optical and PFGE maps was excellent, in terms of both fragment sizing and ordering.

15.3. DISCUSSION

Optical restriction mapping of DNA molecules is a new alternative to conventional gel and hybridization based methods for producing restriction maps of large DNA molecules. Optical mapping is an attractive technology based on the following considerations: i) it is rapid and safe, not requiring time consuming procedures such as gel electrophoresis, preparation and radiolabelling of probes, nucleic acid hybridization and autoradiography. Further, it is an easy and inexpensive technique to perform, requiring—apart from the microscope and camera—very small quantities of very simple materials. ii) The technique yields consistent results, the accuracy of which has been proven by direct comparison with standard methods. iii) The technique, because it analyzes individual DNA molecules, holds enormous potential for miniaturization and automation and consequent order of magnitude increases in throughput and decreases in cost.

This example describes several important improvements to optical mapping that derive from the ability to analyze DNA molecules adhered to APTES derivatized glass surfaces. First, with surface mounting it is easier to find large molecules in one focal plane. This simplifies the analysis necessary for map construction since, in contrast to the previous approach, molecules are imaged after digestion. Second, the longer imaging times possible with surface mounting allow DNA molecules to be extended up to 60% of their polymer contour length (vs. 30% previously). The more extended molecules are more efficiently cleaved by restriction endonucleases: 85% of sites are cut (vs. 50% previously). Thus the basic mechanics of the technique are more robust. A valuable consequence is that fluorescence intensity-based length data are more reproducible and accurate. A third benefit of surface mounting compared to agarose gel fixation is that small DNA fragments are more readily detected because surface mounting restrains their tendency to relax back into the gel matrix and disappear from view. Reliable measurements are now possible for molecules as small as 30 kb (vs. 60 kb previously). A fourth improvement results from the superior performance of the fluorochrome YOYO-1 compared to ethidium homodimer. YOYO-1 produces clearer images of higher contrast and, unlike ethidium homodimer, is unimpeded by high salt. The improved images contribute to more reliable DNA fragment sizing as measured by lower standard deviations on mean restriction fragment sizes.

Presently, a large fraction of the human genome is covered by YAC contigs (Cohen and Weissenbach, Nature 366:698–701, 1993). The information content of most contigs consists of a list of sequence tagged sites or other markers, the YACs associated with each marker and in some cases the sizes of the YACs. In general there is little detailed YAC characterization and as a result it is difficult to assess the true physical distance spanned by most contigs. Further, as physical landmarks become more closely spaced it becomes more difficult to correctly order them using YAC libraries because nearby markers will often be contained in identical sets of YACs, or YAC rearrangements may give contradictory data. Restriction mapping is unique among the techniques available for YAC characterization in providing a truly linear, sequence based representation of DNA content. Restriction maps of overlapping YACs are also useful for sorting out YAC overlap, DNA rearrangement and chimerism. Finally, an ordered restriction map (or maps, using several enzymes) can be treated as a complex fingerprint and used as a tool in map construction, similar to the use of cosmid fingerprinting (Stallings et al., Proc. Natl. Acad. Sci. U.S.A. 87:6218–22, 1990). Such a fingerprint is considerably more complex and reproducible than fingerprints generated by hybridizing digested YAC DNA with repeat sequences. It is evident from relatively advanced sequencing projects in lower organisms that an ordered restriction map is an essential prelude to more detailed studies of DNA sequence. Perhaps because of the extensive labor required, human YAC restriction maps based on PFGE have not been produced on a large scale. The dramatic simplification and increase in speed offered by optical mapping makes the prospect of detailed restriction maps covering large continuous segments of a complex genome an attainable goal. Optical mapping makes it possible to address directly some of the artifacts of YAC cloning. Yeast strains with two or more co-cloned YACs can be effectively analyzed by optical mapping. Yeast strains with unstable YACs in which only a fraction of the yeast contain full length molecules can also be effectively mapped optically. The analysis of genomic regions prone to rearrangement will also be facilitated by optical mapping because of the ease of analyzing multiple YACs with multiple enzymes. Optical mapping is likely to be equally useful in analyzing other large insert clones such as P1, P1 artificial chromosome (PAC) and bacterial artificial chromosome (BAC) clones and ultimately in generating accurate detailed restriction maps for large portioins of the human genome.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by reference.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

REFERENCES

1. Mullis, K. B. and Faloona, F. A. (1987), Specific synthesis of DNS in vitro via a polymerase-catalyzed chain reaction. Methods in Enzymol 155:335–350.
2. Schwartz, D. C., Saffran, W., Welsh, J., Hass, R., Goldenberg, M. and Cantor, C. R. (1983). New technique for purifying large DNAs and studying their properties and packaging. Cold Spring Harbor Symp. Quant. Biol. 47:189–195.
3. Schwartz, D. C. and Cantor, C. R. (1984), Separation of yeast chromosome-sized DNAs by pulsed-field grandient electrophoresis. Cell 37:67–75.
4. Carle, G. F. and Olson, M. V. (1984). Separation of chromosomal DNA molecules from yeast by orthogonal-field. Nucleic Acids Res. 12: 5647–5664.
5. Chu, G., Vollrath, D., and Davis, R. W. (1986), Separation of large DNA molecules by contour clampled homogeneous electric. fields. Science 234: 1582–1585.
6. Clark, S. M., Lai, E., Birren, B. W. and Hood, L. (1988). A novel instrument for separating large DNA molecules with pulsed homogeneous electric fields. Science 241:1203-1205.

7. Barlow, D. P. and Lehrach, H. (1987). genetics by gel electrophoresis: the impact of pulsed field gel electrophoresis on mammalian genetics. Trends in Genetics 3:167-177.

8. Chandrasekharappa, S. C., Marchuk, D. A. and Collins, F. S. (1992). Analysis of yeast artificial chromosome clones. In Methods in Molecular Biology: Pulsed-field gel Electrophoresis, vol. 12 (Eds, M. Burmeister and L. Ulanovsky), The Humana Press, pp. 235-257.

9. Burke, D. T., Carle, G. F., and Olson, M. B. (1987). Cloning of large segments of exogenous DNA into yeast by means of artificial chromosome vectors. Science 236:806-812.

10. Murray, A. W. and Szostak, J. W. (1983). Construction of artificial chromosomes in yeast Nature 305:189-193.

11. Bellanne-Chantelot, C. Lacroix, B., Ougen, P., Billault, A., Beaufils, S., Bertrand, S., Georges, L., Glibbert, F., Gros, T., Lucotte, G., Susini L., Copdani, J., Gesnouin, P., Pookk, S., Vaysseix, G., LuKuo, J., Ried, T., Ward, D., Chumakov, I., LePaslier, D., Barillot, CC. and Cohen, D. (1992). mapping the whole human genome by fingerprinting yeast artificial chromosomes. Cell 70:L 1059-1068.

12. Brownstein, M., Silverman, G. A., Little, R. D., Burke, D. T., Korsmeyer, S. J., Schlessinger, D., and Olson, M. V. (1989). Isolation of single-copy human genes from a library of yeast artificial chromosome clones. Science 244:1348-1351.

13. Schlessinger, D. and Kere, J. (1992), YAC-based mapping of Genome Structure, Function and Evolution. In Genome Analysis, Vol. 4, Strategies for Physical mapping (Eds. K. E. Davies and S. M. Tilghman), Cold Spring Harbor Laboratory Press, pp. 131-159.

14. Campbell, C., Gulati, R., Nandi, A.<., Floy, K. and Hieter, P. (1991). Generation of a nested series of interstitial deletions in yeast artificial chromosomes carrying human DNA. Proc. Natl. Acad. Sci. U.S.A. 88 5744-5748.

15. Zimm, G. H. and Levene, S. D. (1992), Problems and propsects in the theory of gel electrophoresis of DNA Quarterly Reviews of Biophysice. 25: 171-204.

16. Calladine, C. R., Collis, C. M., Drew, H. R., and Mott M. R. (1991). A study of electrophoretic mobility of DNA in agarose and polyacrylamide. journal of Molecular Biology. 221: 981-1005.

17. Louise D. and Serwer, P. (1989). A hybrid mode of rotating gel electrophoresis for separating linear and circular duplex DNA. Applied and Theoretical Electrophoresis I:169-173.

18. Noolandi, J., Slater, G. W., Lim, H. A., and Viovy J. L. (1989). Generalized tube model of biased reptation for gel electrophoresis of DNA. Science 243:1456-1458.

19. Deutsch, J. M. (1988). Theoretical studies of DNA during gel elecctrophoresis Science 240:992-924

20. Glazer, A. N. and Rye, H. S. (1992). Stable dye-DNA intercalation complexes as reagents for high sensitivity fluorescence detection. Nature 359: 859-861.

21. Quesada, M., Rye, H. S. Gingrich, J. C., Glazer, A. N. and Mathies, R. A. (1991). High-sensitivity DNA detection with a laser-excited confocal fluorescence gel scanner. BioTechniques 10:616-625.

22. Mathies, R. A. and Hung, X. C. (1992), Capillary array electrophoresis: an approach to high-speed, high-throughput DNA sequencing. Nature 359:167-169.

23. Glazer, A. N., Peck, K. and Mathies, R. A. (1990). A stable double-stranded DNA-ethidiuum homodimer complex: Application to picogran fluorescence detection of DNA in agarose gels. Proc. Natl. Acad. Sci. U.S.A. 87:3851-3855.

24. Mathies, R. A., Peck, K. and Stryer, L. (1990). Optimization of high-sensitivity fluorescence detection. Anal. Chem 62:1786-1791.

25. Ried, T., Baldini, A., Timothy, C. R., Ward, D. C. (1992). Simultaneous visualization of seven different DNA probes by in situ hybridization using combinatorial fluorescence and digital imaging microscopy. Proc. Natl. Acad. Sci. U.S.A. 89: 1388-1392.

26. Murakami, A., Tada, J., Yamagata, K. and takano, J. (1989). Highly sensitive detection of DNA using enzyme-linked DNA-probe. 1. Colorimetric and fluorometric detection. Nucleic Acids Res. 17:5587-5595.

27. Beck, S., O'Keeffe, T., M. Coull, J. and Koster, H. (1989). Chemiluminescent detection of DNA: application for DNA sequencing and hybridization. Nucleic Acids Res. 17: 5115-5123.

28. Lehrach, H., Drmanac, R., Hoheisel, J., Larin, Zl, Lennon, G., Monaco, A. P., Nizetic, D., Zehetner, G., Poustka, A. (1989). Hybridization fingerprinting in genome mapping and sequencing in Genetic and Physical mapping. (Eds., Davies, K. E., and Tilghman, S. M.) Cold Spring Harbor Laboratory Press, cold Spring Harbor, N.Y., pp 39-81.

29. Larin, Z., Monaco, A/P/ and Lehrach, H. (1991). Yeast artificial chromosome libraries containing large inserts from mouse and human DNA, Proc. Natl. Acad. Sci., 88:4123-4127.

30. Anderson, C. (1993). Genome shortcut leads to problems. Science 259:1684-1687.

31. Chumakov, I. et al. (1992). Continuum of overlapping clones spanning the entire human chromosome 21q. Nature 359:380-387.

32. Vollrath, D., Foote, S. Hilton, A., Brown, L. G., Beer-Romero, P., bogan, J., and Page, D. C. (1992). The Human Y chromosome: A 43-Interval map Based on Naturally Occurring Deletions. Science 258:52-59.

33. Foote, S., Vollrath, D., Hilton, A. and Page, D. C. (1992) The Human Y Chromosome: Overlapping DNA Clones Spanning the Euchromatic Regioin. Science 258: 60-66.

34. Donis-Keller, H., green, P., Helms, C., Cartinhour, S., Weiffenbach, B., Stephens, K., Keith, T. P., Bowden, D. W., Smith, D. R., Lander, E. S., Botstein, D., et al. (1987). A genetic linkage map of the human genome. Cell 51:319-337.

35. Olson, M. V., Dutchik, J. E., Graham, M. Y., Brodeur, G. M., Helms, C., Frank, M., MacCollin, M., Scheinman, R. and Frank, T. (1986). Random-clone strategy for genomic restriction mapping in yeast. Proc. Natl. Acad. Sci. U.S.A. 83: 7826-7830.

36. NIH-CEPH Collaborative mapping Group, (1992). A Comprehensive Genetic Linkage Map of the Human Genome. Science 258: 67-86.

37. Mandel, J-L., Monaco, A. P., Nelson, D. L., Schlessinger, D.l, Willard, Huntington (1992). Genome Analysis and the Human X Chromosome. Science 258: 103-109.

38. Stallings, R. L., Torney, D. C., Hildebrand, C. E., Longmire, J. L., Deaven, L. L., Jett, J. H., Doggett, N. A. and Moysis, R. K. (1990). Physical mapping of human chromosomes by repetitive sequence fingerpringing proc. Natl. Acad. Sci. U.S.A. 87:6218–6222.

39. Craig, G., Nizetic, D., Hoheisel, J. D., Zehetner, G. and lehrach, H. (1990). Ordering of cosmid clones covering the Herpes simplex virus type I (HSV I) genome: a test case for fingerprinting by hybridization. Nucl. Acids.Res. 18:2653–2660.

40. Coulson, A., Sulston, J., Brenner, S., and Kam, J. (1986). Towards a physical map of the nematode C. elegans. proc. Natl. Acad. Sci. U.S.A. 83:7821–7825.

41. Ross, M. T., Hoheisel, J. D., Monaco, A. P., Larin, Z., Zehetner, G. and Lehrach, H. (1992). High-density gridded YAC filters: their potential as genome mapping tools In Techniques for the analysis of complex genomes (Anand, R.). Academic Press Inc., San Diego, Calif.

42. Church, C. and Kiefer-higgins, S. (1988). Multiplex DNA sequencing. Science 240: 185–188.

43. Smith, H. O and Bernstiel, M. L. (1976). A simple method for DNA restriction site mapping. Nucleic Acids Res. 3:2387.

44. Yanagida, M., Hiraoka, Y., and Katsura, I. (1983) Cold Spr. Harb. Symp. on Quant. Biol. XLVII: 177–187.

45. Schwartz, D. C., Hernandez, L. I., Wang, Yu-Ker Wang, Ramnarain, S. P., Huff, E., and Li, X. (1993). Ordered Restriction Maps of Saccharomyces cerevisiae Chromosomes Constructed by optical mapping, Submitted to Science.

46. Guo, X. H., Huff, E. J. and Schwartz, D. C. (1992). Sizing single DNA molecules. Nature 359: 783.

47. Guo, X. and Schwartz, D. C. Molecular Sizes As Determined by Imaging Coil Dynamics in Agarose Gel. Manuscript to be submitted.

48. Mickel, S., Arena, V., and Bauer, W. (1977). Physical properties and gel electrophoresis behavior of R12-derived plasmid DNAs. Nucleic Acids Res. 4:1465–1482.

49. Ashburner, M. (1989). Drosophila, A Laboratory Handbook. Cold Spring Harbor Laboratory Press, Cold Spring Harbor, N.Y.

50. Osheroff, N., Shelton E. R., Brutlag, D. L. (1983). DNA topoisomerase II from Drosophila melanogaster. Relaxation of supercoiled DNA. J. Biol. Chem 258: 9536–9543.

51. Fan, J. B., Chikashige, Y., Smith, C. L., Niwa, O., yanagida, M. and cantor, C. R. (1989). Construction of a Not I restriction map of the fission yeast Schizosaccharomyces pombe genome. Nucleic Acids Res. 17:2801–2818.

52. Ruvolo, P., Hsu, M., and Schwartz, D. Separating the Smallest Drosophila Chromosome by Pulsed Oriented Electrophoresis. Manuscript in preparation.

53. Schwartxz, D. C., Koval, M. (1989). Conformational dynamics of individual DNA molecules during gel electrophoresis. nature 338:520–522.

54. Holm, C., Goto, T., Wang, J. C., Botstein, D. (1985). DNA topoisomerase II is required at the time of mitosis in yeast. cell 41:553–563.

55. Schwartz, D. C. (1985)> Giga-dalton DNA molecules, Ph.D. Thesis, Columbia Universiity, New York, N.Y.

56. Turmel, C., Brassard, e., Forsyth, R., Hook, K., Slater, G. W. and Noolandi, J. (1990). High resolution zero integrated field electrophoresis (ZIFE) of DNA. In Current communications in cell and molecular biology: Electrophoresis of large DNA molecules: Theory and applications, Cold Spring Harbor Laboratory, Cold Spring Harbor, N.Y., pp 101–131.

57. Viovy, J-L, Miomandre, F., Miquel, M-C., Caron, F., and Sor. F. (1992). Irreversible trapping of DNA during crossed-field gel electrophoresis. Electrophoresis 13:1–6.

58. Gemmill, R. M. (1991). Pulsed-field gel electrophoresis. In Adv. Electrophoresis 4":1–48.

59. Smith, S. B. and Bendich, A. J. (1990). Electrophoreticc charge density persistence length of DNA as measured by fluorescence microscopy. Biopolymer 29:1167–1173.

60. Cai, W. and Schwartz, D. C. Why Large DNA Molecules Don't Enter Gels: The Mechanism of Trapping. To Be Subnitted.

61. Roberts, T. M., Lauer, G. D., Klotz, L. C. (1975). Physical techniques for genome analysis. CRC Crit. Rev. Biochem. 3:349.

62. Smith, S. B., Aidridge, P. K., and Callis, J. B. (1989). Observation of individual DNA molecules undergoing gel electrophoresis. Science 243:203–206.

63. Zimm, B. H. (1991). "Lakes-straits" model of field-inversioin electrophoresis of DNA. J. Chem Phys. 94: 2187–2206.

64. Wells, R. D., Klein R. D. and Singleton, C. K. (1981). Type II restriction enzyme. In the Enzymes (P. D. Boyer, Ed.), Academic Press, New York, N.Y., Ed. 3, vol. 14, part A, pp. 167–169.

65. Link, A. J. and Olson, M. V. (1991). Physical map of the Saccharomyces cerevisiae genome at 110-kilobase resolution. Genetics 127:681–698.

66. Koob, M. and Szybalski, W. (1990). Cleaving yeast and Escherichia coli genomes at single site. Science 250:271–273.

67. Koob, M., Burkiewicz, A., Kur, J. and Szybalski, W. (1992). RecA-AC: single-site cleavage of plasmids and chromosomes at any predetermined restriction site. Nucleic Acids Res. 20:5831–5836.

68. Ferrin, L. J. & Camerini-Otero, R. D. (1991). Selective cleavage of human DNA: RecA-assisted restriction endonuclease (RARE) cleavage. Science 254:L 1494–1497.

69. Lai, M. H., Kirsch, D. R. (1989). Nucleotide sequence of cytochrome P450 L1A1 from Candida albicans. Nucleic Acids Res. 17:804.

70. Ranmpino, N. J. and Chrambach, A. (1991). Conformational correlatives of DNA band compression and bidirectional migration during field inversion gel electrophoresis, detected by quantitative video epifluorescence micreoscopy. Biopolymers 31:1297–1307

71. Noolandi, J., Slater, G. W., Lim, H. A., and Viovy, J. L. (1989). Generalized tube model of biased reptation for gel electrophoresis of DNA. Science 243:1456–1458.

72. Zimm, B. H. (1956). Dynamics of polymer molecules in dilute solution: viscoelasticity, flow birefringence and dielectic loss. J. Chem. Phys. 24:269–278.

73. Rouse, P. E. (1953). A theory of the linear viscoelastic properties of dilute solutions of coiling polymers. J. Chem. Phys 21:1272–1280.

74. De Gennes, P-G. (1979). Scaling concepts in polymer physics. Cornell University Press, ithaca, N.Y.

75. Doi, M. and Edwards, S. F. (1986). The Theory of Polymer Dynamics. Oxford University Press.

76. Smith, S. B. and Bendich, A. j> (1990). Electrophoretic charge density and persistence length of DNA as measured by fluorescence microscopy. Biopolymer 29:1167–1173.

77. Smith, S. B., Finzi, I. and Bustamante, C. (1992). Direct mechanical measurements of the elasticity of single DNA molecules by using magnetic beads Science 258:1122–1126.

78. Holzwarth, G., Platt, K. f., mckee, C. B., Whitcomb, R. W. and crater, G. D. (1989). the acceleration of linear DNA during pulsed-field gel electrophoresis. Biopolymers 28: 1043–1058.

79. Borejdo, J. and Defea, K. (1988). The orientation of DNA fragments in the agarose gel. Anal. Biochem. 174:393–398.

80. Borejdo, J. (1989). Orientation of DNA in agarose gels. Biophys. J. 55: 1183–1190.

81. Matsumoto S. Morikawa K. Yanagida M. (1981). Light microscopic structure of DNA in solution studied by the 4'6-diamidino-2-phenylinddole staining method. Journal of Mol. Biol. 132:501–516.

82. Olivera, B. M., Baine, P. and Davidson, D. (1964). Electrophoresis of the nucleic acids. Biopolymers 2: 245–257.

83. Klotz, L. C. and Zimm, B. H. (1972). Retardation times of deoxyribonucleic acid solution, II: Improvements in appratus and theory. Macromolecules 5:471–481.

84. Rau, D. c. and Bloomfield, V. A. (1979). Transient electric birefringencce of T7 viral DNA. Biopolymers 18:L2783–2805.

85. Callis, P. R. and Davidson, N. (1969). Hydrodynamic relaxation times of DNA for decay of flow dichroism measurements. Biopolymers 8:379–390.

86. Taylor, D. L., Wang, Y-L, eds. (1989). Fluorescence Microscopy of Living Cells in Culture. Part B Academic press, Inc., New York, N.Y.

87. Arndt-Jovin, D. J., latt, S. A., Striker, G. and Jovin, T. M. (1979). Fluorescnece decay analysis in solution and in a microscope of DNA and chromosomes stained with quinacrine. J. Histochem. Cytochem. 27:87–95.

88. Cherry, R. J., ed. (1991). New Techniques of Optical microscopy and Microspectroscopy, CRC Press, Inc., Boca Raton, Fla.

89. Herman B. Jacobson, K. (1990). Optical Microscopy for Biology. A John Wiley & Sons, Inc. New York, N.Y.

90. Arndt-Jovin, D. J., Robert-Nicoud, M., Kaufman, S. J. and Jovin, T. M. (1985). Fluorescence digital imaging microscopy in cell biology. Science 230:247–256.

91. Hiraoka, Y., Sedat, J. W. and Agard, D. A. (1987). The use of a charge-coupled device for Quantitative optical microscopy of biological structures. Science 238:36–41.

92. Aikens, R. S., Agard, D. A. and Sedat, J. W. (1989). Solid-state imagers for microscopy. In Fluorescence microscopy of living cells in culture, Vol 29 (Eds. Wang, YL, Taylor, D. L.) Academic Press, Inc. pp. 291–313.

93. Brun, A. M., Harriman, A. (1992). Dynamics of electron transfer between intercalated polycyclic milesules: effect of interspersed bases. J. Am. chem. Soc. 114:3656–3660.

94. Volkmuth, W. D., Austin, R. H. (1992). DNA electrophoresis in microlithographic arrays.; nature 358:L600–602.

95. Cantor, R. C. and Schimmel, P. R. (1980). Biophysical chemistry, Part II: The conformation of biological macromolecules. W.H. Freeman and Co., San Francisco, Calif.

96. Manuelidis, L., Langer-Safer, P. R. and Ward, D. C. (1982). High-resolution mapping of satellite DNA using biotin-labeled DNA probels. J. cell Biol. 95:L619–625.

97. Lawrence, J. B., Villnave, C. A. and Singer, R. H. (1988). Sensitive, high-resolution chromatin and chromosome mapping in situ: Presence and orientation of two closely integrated copies of EBV in a lymphoma cell line. Cell 52:51–61.

98. Heng, H. H. Q., Squire, J. and Tsui, L-C. (1992). High-resolution mapping of mammalian genes by in situ hybridization to free chromatin. Proc. Natl. Acad. Sci., U.S.A. 89:9509–9513.

99. van den Engh, G., Sachs, R., Trask, B. J. (1992). Estimating genomic distance from DNA sequence location in cell nuclei by a random walk model. Science 257:1410–1412.

100. Wang, Y-K and Schwartz, D. C. (1993). Chopped inserts are a convenient alternative to beads. Submitted to Nucleic Acids Res.

101. Serwer, P. and Griess, G. A. (1990). Gel electrophoresis of micron-sized molecules: A problem and a solution. Biopolymers 29:1863–1866.

102. Rigas, B., Welcher, A. A., Ward, D. C. and Weissman, S. M. (1986). Rapid plasmid library screening using RecA-coated biotinylated probes. Proc. Natl. Acad. Sci., U.S.A. 83:9591–9595.

103. Landschulz, W-H, Johnson, P. F. and Mcknight, S. C. (1988). The Leucine zipper: A hypothetical structure common to a new Class of DNA binding proteins. Science 240:1759–1764.

104. Hsieh, P., Camerini-Otero, C. S. and Camerini-Otero, R. D. (1992). The synapsis event in the homologous pairing of DNAs: RecA recognizes and pairs less than onehelical repeat of DNA. Proc. Natl. Acad. Sci. U.S.A. 89:6492–6496.

105. Beck, S. (1992), Nonradioactive detection of DNA Using Dioxetane Chemiluminescence. Methods in Enzymol. 216:143–153.

106. Murakami, A., Tada, J., Yamagata, K. and Takano, J. (1989). Highly sensitive detection of DNA using enzyme-linked DNA-probe. 1. Colorimetric and fluorometric detection. Nucleic Acids Res. 17:5587–5595.

107. Hyman, A. A., Middleton, K., Centola, M., Mitchison, T. J. and Carbon, J. (1992). Microtubulemotor activity of a yeast centromer-binding protein complex. Nature 359:L533–536.

108. Herman, B. (1989). Resonance energy transfer microscopy. Methods in Cell Biol. 30:219–243.

109. Uster, P. S. and Pagano, R. E. (1986) J. Cell Biol. 103:1221–1234.

110. Yanagida, M., Morikawa, K., Hiraoka, Yl, matsumoto, S., Uemura, T., and Okada, S. (1986). In Applications of Fluorescence in the Biomedical Sciences (eds D. L. Taylor, A. S. Waggoner, R. F. Murphy, F. Lanni, and R. R. Birge), Alan R. Liss, Inc., New York, N.Y., pp. 321–345.

111. Kohara, Y., Akiyama, K. and Isono, K. (1987). The physical map of the whole *E. coli* chromosome: application of a new strategy for rapid analysis and sorting of a large genomic library. Cell 50:495–508.

112. Evans, G. A. and Lewis, K. A. (1989). Physical mapping of complex genomies by cosmid multiplex analysis. Proc., Natl. Acad. Sci. U.S.A. 86:5030–5034.

113. Smith, A. M., Birnstiel, M. L. (1976). A simple method for DNA restriction site mapping. Nucleic Acids Res. 3:2387–2399.

114. Barlow, D., Lehrach, H., Poustka, A., and Bates, G. (1989). Long range mapping and cloning of mammalian chromosomes. EMBO practical course. Heidelberg, FRG.

115. Rommens, J. M., Iannuzzi, M. C., Kerem, B-S, Drumm, M. L., Melmer, G., Dean, M., Rozmahel, R., Cole, J. L., Kennedy, D., Hidaka, N., Zsiga, M., BuChwald, M., Riordan, J. R., Tsui, L-C and Collins, F. S. (1989). Identificaiton of the cystic fibrosis gene: Chromosome walking and jumping. Science 245:1059–1065.

116. Riordan, J. R., Rommens, J. M., Kerem, B-S, Alon, N., Rozmahel, R., Grzelczak, Z., Zielenski, J., Lok, S., Plavsic, N., Chou, J-L., Drumm, M. L. Iannuzzi, M. C., Collins, F. S., Tsui, L-C (1989), Identification of the cystic fibrosis gene: cloning and characterization of complementary DNA. Science 245: 1066–1072.

117. Zielenski, J. Rozmahel, R., Bozon, D., Kerem, B., Grzelczak, Z., Riordan, j. R. Rommens, J. M. and Tsui, L-C (1991). Genomic DNA sequence of the cystic fibrosis transmembrande conductance regulator (CFTR) gene. Genomics 10:214–220.

118. Olson, M., Hood, L., Cantor, C. and Botstein, D. (1989). A common language for physical mapping of the human geome. Science 245:1434–1435.

119. Pinkel, D., Lake, S., Gledhill, B. L., Van Dilla, M. A., Stephenson, D. and Watchmaker, G. (1982). High resolution DNA contene measurements of mammalian sperm. Cytometry 3:119.

120. Steen, H. B. and Lindmo, T. (1979). Flow cytometry: A high-resolution instrument for everyone. Science 204:403–404.

121. Dill, K. and Zimm, B. H. (1980). Dynamics of polymer solutions. 2. The determination of molecular weight distribution by viscoelasticity. Macromolecules 13:432–436.

122. Kavenoff, Rlk and Zimm, B. H. (1973). Chromosoma 41:1–27.

123. Sulston, J., Du, Z., Thomas, K., Wilson, R., Hillier, L., Staden, R., Halloran, N., Green, P., thierry-Mieg, J., Qiu, L, Dear, S., Couison, A., Craxton, M., Durgbin, R., Berks, M., Metzstein, M., Hawkins, T., Ainscough, R. and Waterston, R. (1992). The C elegans genome sequencing project: a beginning. Nature 356:37–41.

124. Balding, D. J., Torney, D. C. (1991). Statistical analysis of DNA fingerprint data for ordered clone physical mapping of human chromosomes. Bulleting of Mathematical Biology 53:853–879.

125. Kuspa, A., Vollrath, D., Cheng, Y and Kaiser K. (1989). Physical mapping of the *Myxococcus xanthus* genome by random cloning in yeast artifical chromosomes. Proc. Natl. Acad. Sci. U.S.A. 86:8917–8920.

126. Shafit-Zagardo, B., Maio, J. J. and Brown, F. L. (1982). L1 families of long, interspersed repetitive sequences in human and other primate genomes. Nucleic Acids Res. 10:3175–3193.

127. Botstein, D., White, R. L., Skolnick, M. and Davis, R. W. (1980). Construction of a genetic linkage map in man using restriction fragment length polymorphisms. Am. J. Hum. Genet. 32:314–331.

What is claimed is:

1. A system for characterizing a nucleic acid molecule, comprising:
   (a) the nucleic acid molecule elongated and fixed onto a planar surface so that the nucleic acid molecule remains accessible for enzymatic reactions and/or hybridization reactions;
   (b) an enzyme fixed onto the planar surface;
   (c) a divalent cation cofactor included on the planar surface, wherein the cofactor is required for activity of the fixed enzyme and is reversibly chelated with a divalent cation chelator to protect the fixed enzyme from being activated; and
   (b) a device for imaging the elongated and fixed nucleic acid molecule to obtain its physical characteristics.

2. The system of claim 1 in which the enzyme is a restriction endonuclease, an exonuclease, a polymerase, a ligase or a helicase.

3. The system of claim 1 in which the cofactor is released upon exposure to a specific wavelength of light, and the fixed enzyme is activated in the location of the exposure.

* * * * *